(12) United States Patent
Takenaka

(10) Patent No.: US 7,871,803 B2
(45) Date of Patent: Jan. 18, 2011

(54) GENE ENCODING NOVEL LUCIFERASE

(75) Inventor: Hiromi Takenaka, Tokyo (JP)

(73) Assignee: NEC Soft, Ltd., Tokyo (JP)

( * ) Notice: Subject to any disclaimer, the term of this patent is extended or adjusted under 35 U.S.C. 154(b) by 649 days.

(21) Appl. No.: 11/721,032

(22) PCT Filed: Dec. 9, 2004

(86) PCT No.: PCT/JP2004/018401

§ 371 (c)(1),
(2), (4) Date: Jun. 6, 2007

(87) PCT Pub. No.: WO2006/061906

PCT Pub. Date: Jun. 15, 2006

(65) Prior Publication Data

US 2009/0233320 A1    Sep. 17, 2009

(51) Int. Cl.
*C12N 15/53* (2006.01)
*C12N 9/02* (2006.01)
*C12Q 1/68* (2006.01)
*C12Q 1/66* (2006.01)

(52) U.S. Cl. .................. 435/189; 435/6; 435/8; 435/320.1; 435/325; 536/23.2

(58) Field of Classification Search ............ None
See application file for complete search history.

(56) References Cited

U.S. PATENT DOCUMENTS 5,292,658 A  *  3/1994   Cormier et al.  ........  435/252.33

FOREIGN PATENT DOCUMENTS

| JP | 2002-507410 A | 3/2002 |
| JP | 2002-320482 A | 11/2002 |
| WO | WO 99/49019 A2 | 9/1999 |

OTHER PUBLICATIONS

Y. Nakajima et al. "cDNA Cloning and Characterization of a Secreted Luciferase from the Luminous Japanese Ostracod, *Cypridina noctiluca*", Biosci. Biotechnol. Biochem. 68(3): 565-570 (Mar. 2004).*
Markova SV. Et al., Cloning and Expression of cDNA for a Luciferase from the Marine Copepod *Metridia longa*. J. Biol. Chem., 2004.1, vol. 279, No. 5, pp. 3212 to 3217.
Yasuo Kakunami et al., "Toyamawan ni Okeru Kaiashirui *Metridia pacifica* (Calanoida) No Biomass Model", Bulletin of the Japanese Society of Scientific Fisheries, 2000 Nen, pp. 1014 to 1019.

* cited by examiner

*Primary Examiner*—Rebecca Prouty
(74) *Attorney, Agent, or Firm*—Sughrue Mion, PLLC

(57) ABSTRACT

The present invention provides genes encoding novel luciferases having at least the properties of: being capable of using coelenterazine as their luminescent substrates; and being capable of being recombinantly expressed in a mammal cell as a host and produced to be secreted to the outside of the host cell. Specifically, the gene encoding novel luciferases according to the present invention is a DNA molecule comprising a nucleotide sequence encoding any of the full-length amino acid sequences of two types of luciferase proteins, luciferase 1 and luciferase 2, from *M. pacifica*, and is, for example, a gene encoding the following full-length amino acid sequence of the luciferase 1.

```
MMEIQVLFAL ICFALVQANP TENKDDIDIV GVEGKFGTTD         60
LETDLFTIVE DMNVISRDTN
LANSDADRGK MPGKKLPLEV LIEMEANARK AGCTRGCLIC        120
LSKIKCTAKM KVYIPGRCHD
YGGDKKTGQA GIVGAIVDIP EISGFKELGP MEQFIAQVDL        180
CADCTTGCLK GLANVKCSAL
LKKWLPDRCA SFADKIQSEV DNIKGLAGDR                   210
```

13 Claims, 6 Drawing Sheets

Fig. 1
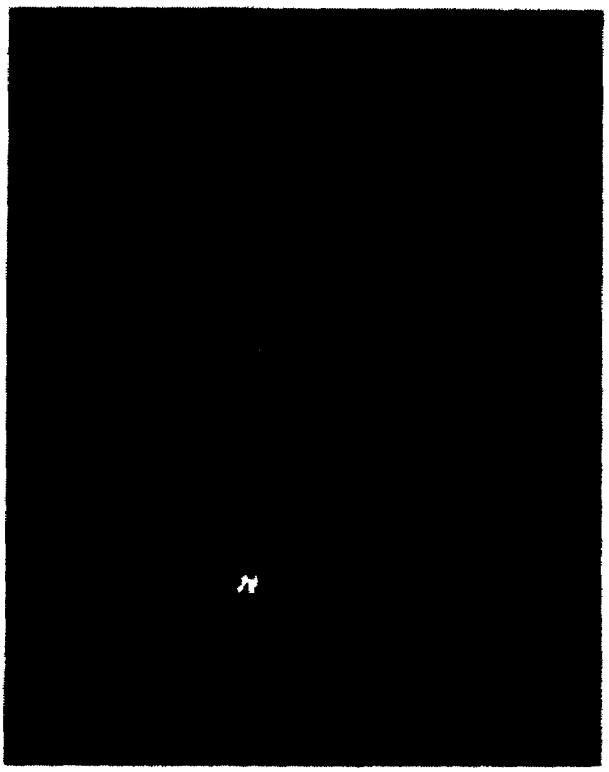
On UV
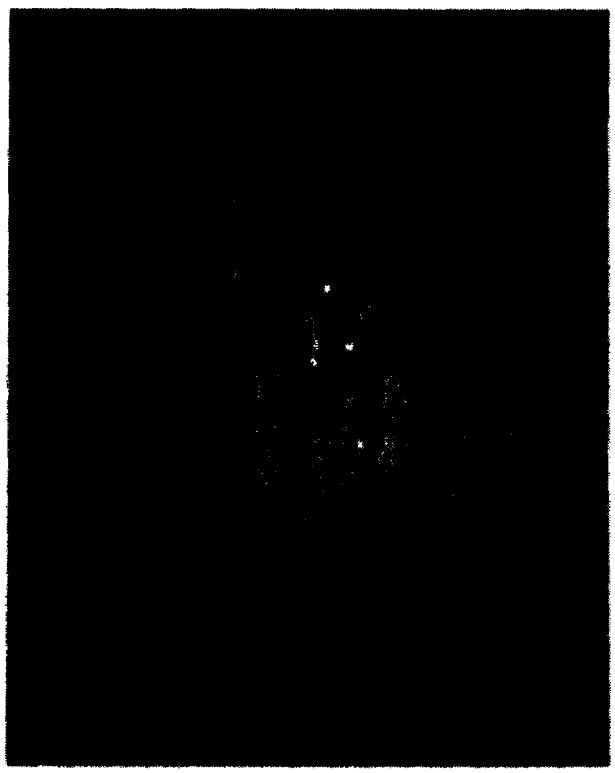
Brightfield
*Metridia pacifica*

Luciferase 1&2 pH dependency

Effect of metal ions

Fig. 4
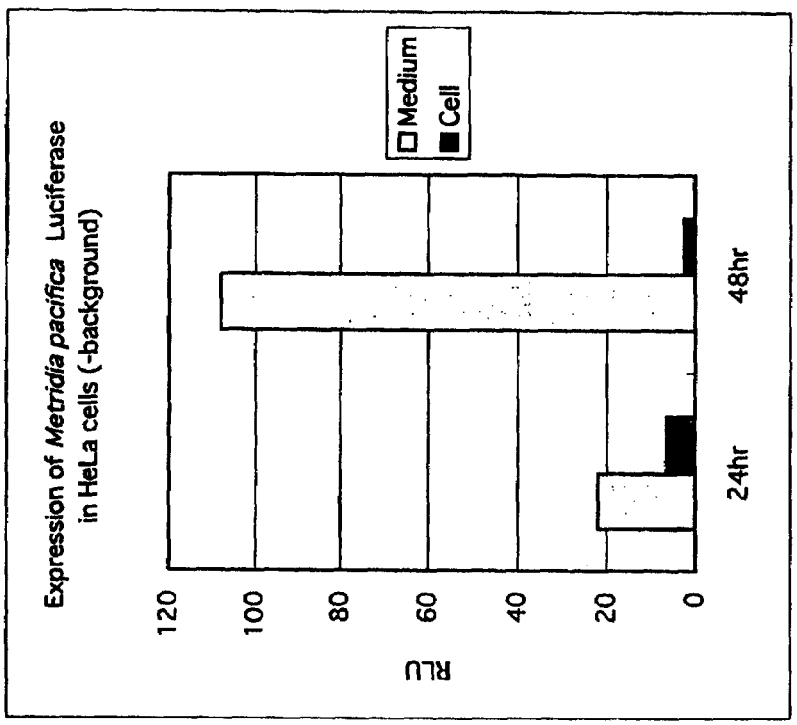
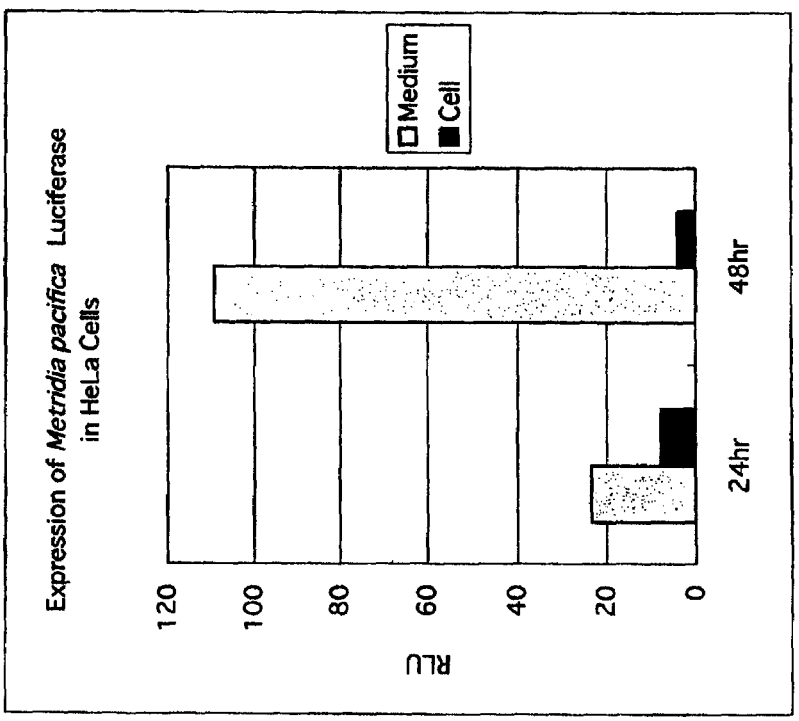

Fig. 5

*M. pacifica* luciferase 1 (210AA)

```
luc1-10     MKIILSVILAYCVTDNCQD
M.longa     MMEIQVLFALICFALVQANPTENKDDIDIVGEGKFGTDLETDLFTIVEDMNVISRDTNLANS------DADRGKMPGKKLPLE
            -MDIKVVFTLVFSALVQAKSTEFDPNIDIVGLEGKFGITNLETDLFTIWETMEVMIKADIADTDRASNFVATETDANRGKMPGKKLPLA
            *:*:*:*:. *****:..*. .:***:.** *:**:..:::  ::.*:. ********* luc1-10     VLIEMEANARKAGCTRGCLICLSKIKCTAKMKVYIPGRCHDYGGDKKTGQAGIVGAIVDIPEISGFKELGPMEQFIAQVDLCADCTTGC
M.longa     VIMEMEANAFKAGCTRGCLICLSLIKCTAKMKVYIPGRCHDYGGDKKTGQAGIVGAIVDIPEISGFKEMAPMEQFIAQVDRCASCTTGC
            *::******.******* ************************************** .***   ***** luc1-10     LKGLANVKCSALLKKWLPDRCASFADKIQSEVDNIKGLAGDR
M.longa     LKGLANVKCSELLKKWLPDRCASFADKIQKEVHNIKGMAGDR
            ********** ****************** **:***:****
```

*M. pacifica* luciferase 2 (189AA)

```
luc2-7      MKTIILSVILAYCVTDNCQD
G.princeps  MGVKLLIFAVVCVAAAQAATINENFEDIDLVAIGGSFALDVDANRGGHGGHPGKKMPKEVLVEMEANAKRAGCHRGCLICLSHIKCTKK
            MGVKVLFALICIAVAEAKPTENNEDFNIVAVASNFATTDLDADR---GKLPGKKLPLEVLKEMEANARKAGCTRGCLICLSHIKCTPK
            ****:::*:*  :* .. ..: : *.*: :  :.. :*:**     ** *. *.: ******.*.* luc2-7      MKKFIPGRCHSYEGDKDSAQGGIGEEIVDMPEIPGFKDKEPMDQFIAQVDLCVDCTTGCLKGLANVHCSDLLKKWLPSRCKTFASKIQ
G.princeps  MKKFIPGRCHTYEGDKESAQGGIGEATVDIPEIPGFKDLEPMEQFIAQVDLCVDCTTGCLKGLANVQCSDLLKKWLPQRCATFASKIQ
            ******** * **** :****** *:****************** ***** .******* luc2-7      SQVDTIKGLAGDR
G.princeps  GQVDKIKGAGGD-
             *** *** .*
```

Fig. 6

GENE ENCODING NOVEL LUCIFERASE

TECHNICAL FIELD

The present invention relates to genes encoding novel luciferases. In particular, the present invention relates to coding genes available in the recombinant expression of novel luciferases from marine plankton.

BACKGROUND ART

Luciferase, which is an enzyme protein capable of emitting bioluminescence through the enzymatic oxidation of luminescent substrates (luciferins), has conventionally been utilized as a reporter protein in a variety of bioassay systems. That is, genes encoding several luciferases have been collected for the purpose of being recombinantly expressed in the host cell in in-vitro cell culture systems, and recombinant expression systems thereof have also been established. Particularly, in the recombinant expression systems of luciferase, a gene encoding luciferase is transcribed under the control of a heterologous promoter in a host cell, and the transcribed mRNA is translated into a peptide chain to produce luciferase protein of interest.

The use of secreted luciferase, which is a luciferase protein recombinantly expressed in a host cell and secreted to the outside of the cell, enables the convenient monitoring of reporter protein yields by sampling a medium containing the secreted reporter protein without sampling the cultured host cell. For example, when time-dependent changes in reporter protein yield are observed in in-vitro cell culture systems, the use of the secreted luciferase enables the use of an approach comprising sampling a predetermined amount of a medium at each point in time and monitoring the concentration of secreted luciferase contained in the medium. There were previously reported secreted luciferases capable of being recombinantly expressed that can be employed in such application, such as luciferases from *Cypridina* (*Vargula*) *hilgendorfii* belonging to Ostracoda (Thompson, E. M., et al., Proc. Natl. Acad. Sci. USA, 86, 6567-6571 (1989)) and from *Oplophorus gracilirostris* belonging to Decapoda (Inouye, S., et al., FEBS Lett., 481, 19-25 (2000); JP 2002-320482 A). It have also been reported that these two types of secreted luciferases were produced by recombinant expression using animal cells as hosts to be secreted therefrom.

Furthermore, there were previously reported, as for secreted luciferases found in other origins, luciferases from *Gaussia princeps* (GenBank™/EBI accession number AY015993) and *Metridia longa* (GenBank™/EBI accession number AY364164; J. Biol. Chem. Vol. 279, No. 5 pp. 3212-3217 (2004)) both belonging to Metridinidae.

These secreted luciferases cause luminescence through the actions on their respective luminescent substrates (luciferins) specific to the organisms. For constructing a variety of bioassay systems, the luciferases are desired to be capable of acting on more versatile luminescent substrates (luciferins). For example, when the following coelenterazine is utilized as a more versatile luminescent substrate (luciferin),

[Formula 1]

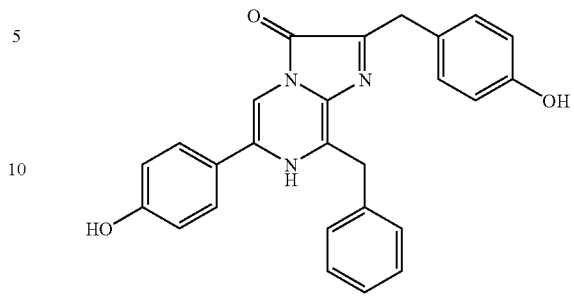

Such secreted luciferase capable of causing desired luminescence is preferable for constructing a variety of bioassay systems. For example, there have been reported luciferases from *Cypridina* (*Vargula*) *hilgendorfii* belonging to Ostracoda, from *Oplophorus gracilirostris* belonging to Decapoda, from *Gaussia princeps*, and from *Metridia longa*, which are all capable of using the coelenterazine as their luminescent substrates (luciferins).

DISCLOSURE OF THE INVENTION

Some of previously reported luciferases have such properties of:

being capable of using coelenterazine as their luminescent substrates (luciferins); and being capable of being produced by recombinant expression, for example, using a mammal cell as a host as to be secreted to the outside of the host cell, which properties are desired for constructing a variety of bioassay systems. However, the types of the luciferases reported are very limited, and options of available secreted luciferases have been desired to be further increased for constructing diverse bioassay systems. That is to say, it has further been desired to search novel secreted luciferases that satisfy the properties described above and to provide genes encoding the secreted luciferases, which are used in the recombinant expression of such novel secreted luciferases.

The present invention solves such problems. That is to say, an object of the present invention is to provide genes encoding novel luciferases having at least the properties of:

being capable of using coelenterazine as their luminescent substrates (luciferins); and being capable of being produced by recombinant expression, for example, using a mammal cell as a host as to be secreted to the outside of the host cell.

The present inventors pursued the search of novel luciferases in order to solve said problems in questions. As a result, the present inventors found that *Metridia pacifica*, one species of marine plankton belonging to Metridinidae, produces secreted luciferases capable of using coelenterazine as their luminescent substrates (luciferins). The present inventors pursued the cloning of genes encoding the secreted luciferases from *Metridia pacifica* and consequently found out that *Metridia pacifica* actually produces two types of secreted luciferases. The present inventors separately cloned genes encoding these two types of secreted luciferases, *Metridia pacifica* luciferase 1 and *Metridia pacifica* luciferase 2, from *Metridia pacifica*, and recombinantly expressed them in human-derived established cell lines, demonstrating that the two types of luciferases are actually secreted to the outside of the host cells. The present inventors completed the present invention on the basis of a series of these findings.

In particular, a gene encoding a luciferase protein from *M. pacifica* according to the first embodiment of the present invention is a gene encoding a luciferase protein: luciferase 1 from *M. pacifica*, characterized in that the gene is a DNA molecule having a nucleotide sequence comprising a nucleotide sequence encoding the following full-length amino acid sequence (SEQ ID NO: 1) of the luciferase protein: luciferase 1 from *M. pacifica*.

```
Met Met Glu Ile Gln Val Leu Phe Ala Leu Ile Cys
 1               5                      10
Phe Ala Leu Val Gln Ala Asn Pro Thr Glu Asn Lys
            15                  20
Asp Asp Ile Asp Ile Val Gly Val Glu Gly Lys Phe
 25              30                      35
Gly Thr Thr Asp Leu Glu Thr Asp Leu Phe Thr Ile
            40                  45
Val Glu Asp Met Asn Val Ile Ser Arg Asp Thr Asn
 50              55                      60
Leu Ala Asn Ser Asp Ala Asp Arg Gly Lys Met Pro
            65                  70
Gly Lys Lys Leu Pro Leu Glu Val Leu Ile Glu Met
         75                      80
Glu Ala Asn Ala Arg Lys Ala Gly Cys Thr Arg Gly
 85              90                      95
Cys Leu Ile Cys Leu Ser Lys Ile Lys Cys Thr Ala
            100                 105
Lys Met Lys Val Tyr Ile Pro Gly Arg Cys His Asp
       110                  115             120
Tyr Gly Gly Asp Lys Lys Thr Gly Gln Ala Gly Ile
                125                 130
Val Gly Ala Ile Val Asp Ile Pro Glu Ile Ser Gly
            135                 140
Phe Lys Glu Leu Gly Pro Met Glu Gln Phe Ile Ala
 145                 150                     155
Gln Val Asp Leu Cys Ala Asp Cys Thr Thr Gly Cys
            160                 165
Leu Lys Gly Leu Ala Asn Val Lys Cys Ser Ala Leu
       170                  175              180
Leu Lys Lys Trp Leu Pro Asp Arg Cys Ala Ser Phe
            185                 190
Ala Asp Lys Ile Gln Ser Glu Val Asp Asn Ile Lys
       195                  200
Gly Leu Ala Gly Asp Arg
 205                 210
```

In this context, it is preferred that the nucleotide sequence encoding the full-length amino acid sequence (SEQ ID NO: 1) of the luciferase protein: luciferase 1 from *M. pacifica* be the following nucleotide sequence (SEQ ID NO: 2).

```
ATG ATG GAA ATA CAA GTT CTT TTT GCT CTC ATT TGC    36
Met Met Glu Ile Gln Val Leu Phe Ala Leu Ile Cys
 1               5                      10

TTT GCA TTG GTG CAG GCC AAT CCA ACT GAA AAC AAA    72
Phe Ala Leu Val Gln Ala Asn Pro Thr Glu Asn Lys
            15                  20

GAT GAC ATT GAC ATT GTT GGT GTA GAA GGA AAA TTT   108
Asp Asp Ile Asp Ile Val Gly Val Glu Gly Lys Phe
 25              30                      35

GGT ACA ACA GAC CTT GAG ACA GAC TTA TTC ACC ATC   144
Gly Thr Thr Asp Leu Glu Thr Asp Leu Phe Thr Ile
            40                  45

GTG GAG GAT ATG AAT GTC ATC AGT AGA GAC ACC AAT   180
Val Glu Asp Met Asn Val Ile Ser Arg Asp Thr Asn
 50              55                      60

CTA GCC AAC AGT GAT GCT GAC CGC GGT AAA ATG CCT   216
Leu Ala Asn Ser Asp Ala Asp Arg Gly Lys Met Pro
            65                  70

GGT AAA AAA CTG CCA CTG GAG GTA CTC ATA GAG ATG   252
Gly Lys Lys Leu Pro Leu Glu Val Leu Ile Glu Met
         75                      80

GAA GCC AAT GCT CGT AAA GCT GGC TGC ACC AGG GGA   288
Glu Ala Asn Ala Arg Lys Ala Gly Cys Thr Arg Gly
 85              90                      95

TGT CTC ATC TGT CTT TCA AAG ATC AAG TGT ACA GCA   324
Cys Leu Ile Cys Leu Ser Lys Ile Lys Cys Thr Ala
            100                 105

AAA ATG AAG GTG TAC ATT CCA GGA AGA TGT CAT GAT   360
Lys Met Lys Val Tyr Ile Pro Gly Arg Cys His Asp
       110                  115             120

TAT GGC GGT GAC AAG AAA ACT GGA CAG GCA GGA ATA   396
Tyr Gly Gly Asp Lys Lys Thr Gly Gln Ala Gly Ile
                125                 130

GTT GGT GCC ATT GTT GAC ATT CCC GAA ATT TCT GGA   432
Val Gly Ala Ile Val Asp Ile Pro Glu Ile Ser Gly
            135                 140

TTC AAG GAG TTG GGA CCC ATG GAG CAG TTT ATT GCT   468
Phe Lys Glu Leu Gly Pro Met Glu Gln Phe Ile Ala
 145                 150                     155

CAA GTT GAT CTT TGC GCT GAC TGC ACA ACT GGC TGC   504
Gln Val Asp Leu Cys Ala Asp Cys Thr Thr Gly Cys
            160                 165

CTC AAA GGT CTT GCC AAT GTC AAG TGC TCC GCA CTC   540
Leu Lys Gly Leu Ala Asn Val Lys Cys Ser Ala Leu
       170                  175              180

CTG AAG AAA TGG CTT CCA GAC AGA TGT GCA AGT TTT   576
Leu Lys Lys Trp Leu Pro Asp Arg Cys Ala Ser Phe
            185                 190

GCT GAC AAA ATC CAG AGT GAA GTA GAC AAC ATC AAG   612
Ala Asp Lys Ile Gln Ser Glu Val Asp Asn Ile Lys
       195                  200

GGC TTG GCT GGA GAT CGT TGA                       633
Gly Leu Ala Gly Asp Arg  *
 205                 210
```

For example, the gene may be a DNA molecule having the following nucleotide sequence (SEQ ID NO: 5) as the nucleotide sequence comprising the nucleotide sequence encoding the full-length amino acid sequence (SEQ ID NO: 1) of the luciferase protein: luciferase 1 from *M. pacifica*.

```
GGAGACAACG GATCCAAAAG GAAAGGAGCT AAATCTACAG TCTAGAAC           48

ATG ATG GAA ATA CAA GTT CTT TTT GCT CTC ATT TGC                84
Met Met Glu Ile Gln Val Leu Phe Ala Leu Ile Cys
 1               5                   10

TTT GCA TTG GTG CAG GCC AAT CCA ACT GAA AAC AAA               120
Phe Ala Leu Val Gln Ala Asn Pro Thr Glu Asn Lys
         15                  20

GAT GAC ATT GAC ATT GTT GGT GTA GAA GGA AAA TTT               156
Asp Asp Ile Asp Ile Val Gly Val Glu Gly Lys Phe
 25                  30                  35

GGT ACA ACA GAC CTT GAG ACA GAC TTA TTC ACC ATC               192
Gly Thr Thr Asp Leu Glu Thr Asp Leu Phe Thr Ile
             40                  45

GTG GAG GAT ATG AAT GTC ATC AGT AGA GAC ACC AAT               228
Val Glu Asp Met Asn Val Ile Ser Arg Asp Thr Asn
     50                  55                  60

CTA GCC AAC AGT GAT GCT GAC CGC GGT AAA ATG CCT               264
Leu Ala Asn Ser Asp Ala Asp Arg Gly Lys Met Pro
                 65                  70

GGT AAA AAA CTG CCA CTG GAG GTA CTC ATA GAG ATG               300
Gly Lys Lys Leu Pro Leu Glu Val Leu Ile Glu Met
         75                  80

GAA GCC AAT GCT CGT AAA GCT GGC TGC ACC AGG GGA               336
Glu Ala Asn Ala Arg Lys Ala Gly Cys Thr Arg Gly
 85                  90                  95

TGT CTC ATC TGT CTT TCA AAG ATC AAG TGT ACA GCA               372
Cys Leu Ile Cys Leu Ser Lys Ile Lys Cys Thr Ala
             100                 105

AAA ATG AAG GTG TAC ATT CCA GGA AGA TGT CAT GAT               408
Lys Met Lys Val Tyr Ile Pro Gly Arg Cys His Asp
     110                 115                 120

TAT GGC GGT GAC AAG AAA ACT GGA CAG GCA GGA ATA               444
Tyr Gly Gly Asp Lys Lys Thr Gly Gln Ala Gly Ile
                 125                 130

GTT GGT GCC ATT GTT GAC ATT CCC GAA ATT TCT GGA               480
Val Gly Ala Ile Val Asp Ile Pro Glu Ile Ser Gly
         135                 140

TTC AAG GAG TTG GGA CCC ATG GAG CAG TTT ATT GCT               516
Phe Lys Glu Leu Gly Pro Met Glu Gln Phe Ile Ala
145                 150                 155

CAA GTT GAT CTT TGC GCT GAC TGC ACA ACT GGC TGC               552
Gln Val Asp Leu Cys Ala Asp Cys Thr Thr Gly Cys
             160                 165

CTC AAA GGT CTT GCC AAT GTC AAG TGC TCC GCA CTC               588
Leu Lys Gly Leu Ala Asn Val Lys Cys Ser Ala Leu
     170                 175                 180

CTG AAG AAA TGG CTT CCA GAC AGA TGT GCA AGT TTT               624
Leu Lys Lys Trp Leu Pro Asp Arg Cys Ala Ser Phe
                 185                 190

GCT GAC AAA ATC CAG AGT GAA GTA GAC AAC ATC AAG               660
Ala Asp Lys Ile Gln Ser Glu Val Asp Asn Ile Lys
         195                 200

GGC TTG GCT GGA GAT CGT TGA                                   681
Gly Leu Ala Gly Asp Arg *
205                 210

ATAAACCTGA CAGAACAGAA CAAGAGATAA CTGGATCATG ATATGCTTGA        731

CTCATGCTAA AAAGTGGCC ATTTTTTTGT CAAACAGAAT GAAATTAAAA         781
```

-continued
TATTGAATTG TTTATTAATA TGAATGGAAT TCCTATAAAT ATATTCTATG    831

TAATCCAAAA AAAAAAAAAA AAAAAAAAAA AAAAAG    867

In addition, the first embodiment of the present invention also provides even a gene encoding a variant of a luciferase protein from *M. pacifica* described below.

That is to said, a gene encoding a variant of a luciferase protein from *M. pacifica* according to the first embodiment of the present invention includes:

a gene encoding a variant of a luciferase protein: luciferase 1 from *M. pacifica*, characterized in that the gene is a DNA molecule having a nucleotide sequence comprising a nucleotide sequence encoding the following full-length amino acid sequence (SEQ ID NO: 7) of the variant of a luciferase protein: luciferase 1 from *M. pacifica*:

```
Met Met Glu Ile Lys Val Leu Phe Ala Leu Ile Cys
 1               5                  10

Phe Ala Leu Val Gln Ala Asn Pro Thr Glu Asn Lys
            15                  20

Asp Asp Ile Asp Ile Val Gly Val Glu Gly Lys Phe
 25              30                  35

Gly Thr Thr Asp Leu Glu Thr Asp Leu Phe Thr Ile
             40                  45

Val Glu Asp Met Asn Val Ile Ser Arg Asp Thr Asn
     50              55                  60

Leu Ala Asn Ser Asp Ala Asp Arg Gly Lys Met Pro
             65                  70

Gly Lys Lys Leu Pro Leu Glu Val Leu Ile Glu Met
             75                  80

Glu Ala Asn Ala Arg Lys Ala Gly Cys Thr Arg Gly
 85              90                  95

Cys Leu Ile Cys Leu Ser Lys Ile Lys Cys Thr Ala
             100                 105

Lys Met Lys Val Tyr Ile Pro Gly Arg Cys His Asp
     110             115                 120

Tyr Gly Gly Asp Lys Lys Thr Gly Gln Ala Gly Ile
             125                 130

Val Gly Ala Ile Val Asp Ile Pro Glu Ile Ser Gly
         135             140

Phe Lys Glu Leu Gly Pro Met Glu Gln Phe Ile Ala
 145             150                 155

Gln Val Asp Leu Cys Ala Asp Cys Thr Thr Gly Cys
             160             165

Leu Lys Gly Leu Ala Asn Val Lys Cys Ser Ala Leu
     170             175                 180

Leu Lys Lys Trp Leu Pro Asp Arg Cys Ala Ser Phe
             185             190

Ala Asp Lys Ile Gln Ser Glu Val Asp Asn Ile Lys
         195             200

Gly Leu Ala Gly Asp Arg
 205                 210;
``` for instance, the gene encoding a variant of a luciferase protein from *M. pacifica*, wherein the nucleotide sequence encoding the full-length amino acid sequence (SEQ ID NO: 7) of the variant of a luciferase protein: luciferase 1 from *M. pacifica* is the following nucleotide sequence (SEQ ID NO: 9):

```
ATG ATG GAA ATA AAA GTT CTT TTT GCT CTC ATT TGC   36
Met Met Glu Ile Lys Val Leu Phe Ala Leu Ile Cys
 1               5                  10

TTT GCA TTG GTG CAG GCC AAT CCA ACT GAA AAC AAA   72
Phe Ala Leu Val Gln Ala Asn Pro Thr Glu Asn Lys
            15                  20

GAT GAC ATT GAC ATT GTT GGT GTA GAA GGA AAA TTT   108
Asp Asp Ile Asp Ile Val Gly Val Glu Gly Lys Phe
 25              30                  35

GGT ACA ACA GAC CTT GAG ACA GAC TTA TTC ACC ATC   144
Gly Thr Thr Asp Leu Glu Thr Asp Leu Phe Thr Ile
             40                  45

GTG GAG GAT ATG AAT GTC ATC AGT AGA GAC ACC AAT   180
Val Glu Asp Met Asn Val Ile Ser Arg Asp Thr Asn
     50              55                  60

CTA GCC AAC AGT GAT GCT GAC CGC GGT AAA ATG CCT   216
Leu Ala Asn Ser Asp Ala Asp Arg Gly Lys Met Pro
             65                  70

GGT AAA AAA CTG CCA CTG GAG GTA CTC ATA GAG ATG   252
Gly Lys Lys Leu Pro Leu Glu Val Leu Ile Glu Met
             75                  80

GAA GCC AAT GCT CGT AAA GCT GGC TGC ACC AGG GGA   288
Glu Ala Asn Ala Arg Lys Ala Gly Cys Thr Arg Gly
 85              90                  95

TGT CTC ATC TGT CTT TCA AAG ATC AAG TGT ACA GCA   324
Cys Leu Ile Cys Leu Ser Lys Ile Lys Cys Thr Ala
             100                 105

AAA ATG AAG GTG TAC ATT CCA GGA AGA TGT CAT GAT   360
Lys Met Lys Val Tyr Ile Pro Gly Arg Cys His Asp
     110             115                 120

TAT GGC GGT GAC AAG AAA ACT GGA CAG GCA GGA ATA   396
Tyr Gly Gly Asp Lys Lys Thr Gly Gln Ala Gly Ile
             125             130

GTT GGT GCC ATT GTT GAC ATT CCC GAA ATT TCT GGA   432
Val Gly Ala Ile Val Asp Ile Pro Glu Ile Ser Gly
         135             140

TTC AAG GAG TTG GGA CCC ATG GAG CAG TTT ATT GCT   468
Phe Lys Glu Leu Gly Pro Met Glu Gln Phe Ile Ala
 145             150                 155

CAA GTT GAT CTT TGC GCT GAC TGC ACA ACT GGC TGC   504
Gln Val Asp Leu Cys Ala Asp Cys Thr Thr Gly Cys
             160             165

CTC AAA GGT CTT GCC AAT GTC AAG TGC TCC GCA CTC   540
Leu Lys Gly Leu Ala Asn Val Lys Cys Ser Ala Leu
     170             175                 180

CTG AAG AAA TGG CTT CCA GAC AGA TGT GCA AGT TTT   576
Leu Lys Lys Trp Leu Pro Asp Arg Cys Ala Ser Phe
             185             190

GCT GAC AAA ATC CAG AGT GAA GTA GAC AAC ATC AAG   612
Ala Asp Lys Ile Gln Ser Glu Val Asp Asn Ile Lys
         195             200
```

```
                                    -continued
GGC TTG GCT GGA GAT CGT TGA                         633
Gly Leu Ala Gly Asp Arg  *
205                210;
``` or alternatively, a gene encoding a variant of a luciferase protein: luciferase 1 from *M. pacifica*, characterized in that the gene is a DNA molecule having a nucleotide sequence comprising a nucleotide sequence encoding the following full-length amino acid sequence (SEQ ID NO: 8) of the variant of a luciferase protein: luciferase 1 from *M. pacifica*:

```
Met Met Glu Val Lys Val Val Phe Ala Leu Ile Cys
 1               5                       10

Phe Ala Leu Val Gln Ala Asn Pro Thr Glu Asn Lys
         15                  20

Asp Asp Ile Asp Ile Val Gly Val Glu Gly Lys Phe
 25              30                       35

Gly Thr Thr Asp Leu Glu Thr Asp Leu Phe Thr Ile
             40                  45

Val Glu Asp Met Asn Val Ile Ser Arg Asp Thr Asn
     50                  55                  60

Leu Ala Asn Ser Asp Ala Asp Arg Gly Lys Met Pro
                 65                  70

Gly Lys Lys Leu Pro Leu Glu Val Leu Ile Glu Met
             75                  80

Glu Ala Asn Ala Arg Lys Ala Gly Cys Thr Arg Gly
 85              90                       95

Cys Leu Ile Cys Leu Ser Lys Ile Lys Cys Thr Ala
            100                 105

Lys Met Lys Val Tyr Ile Pro Gly Arg Cys His Asp
        110                 115                 120

Tyr Gly Gly Asp Lys Lys Thr Gly Gln Ala Gly Ile
                125                 130

Val Gly Ala Ile Val Asp Ile Pro Glu Ile Ser Gly
        135                 140

Phe Lys Glu Leu Gly Pro Met Glu Gln Phe Ile Ala
145                 150                 155

Gln Val Asp Leu Cys Ala Asp Cys Thr Thr Gly Cys
            160                 165

Leu Lys Gly Leu Ala Asn Val Lys Cys Ser Ala Leu
    170                 175                 180

Leu Lys Lys Trp Leu Pro Asp Arg Cys Ala Ser Phe
            185                 190

Ala Asp Lys Ile Gln Ser Glu Val Asp Asn Ile Lys
        195                 200

Gly Leu Ala Gly Asp Arg
205                210;
``` for example, the gene encoding a variant of a luciferase protein from *M. pacifica*, wherein the nucleotide sequence encoding the full-length amino acid sequence (SEQ ID NO: 8) of the variant of a luciferase protein: luciferase 1 from *M. pacifica* is the following nucleotide sequence (SEQ ID NO: 10).

```
ATG ATG GAA GTA AAA GTT GTT TTT GCT CTC ATT TGC   36
Met Met Glu Val Lys Val Val Phe Ala Leu Ile Cys
 1               5                       10

TTT GCA TTG GTG CAG GCC AAT CCA ACT GAA AAC AAA   72
Phe Ala Leu Val Gln Ala Asn Pro Thr Glu Asn Lys
         15                  20

GAT GAC ATT GAC ATT GTT GGT GTA GAA GGA AAA TTT  108
Asp Asp Ile Asp Ile Val Gly Val Glu Gly Lys Phe
 25              30                       35

GGT ACA ACA GAC CTT GAG ACA GAC TTA TTC ACC ATC  144
Gly Thr Thr Asp Leu Glu Thr Asp Leu Phe Thr Ile
             40                  45

GTG GAG GAT ATG AAT GTC ATC AGT AGA GAC ACC AAT  180
Val Glu Asp Met Asn Val Ile Ser Arg Asp Thr Asn
     50                  55                  60

CTA GCC AAC AGT GAT GCT GAC CGC GGT AAA ATG CCT  216
Leu Ala Asn Ser Asp Ala Asp Arg Gly Lys Met Pro
                 65                  70

GGT AAA AAA CTG CCA CTG GAG GTA CTC ATA GAG ATG  252
Gly Lys Lys Leu Pro Leu Glu Val Leu Ile Glu Met
             75                  80

GAA GCC AAT GCT CGT AAA GCT GGC TGC ACC AGG GGA  288
Glu Ala Asn Ala Arg Lys Ala Gly Cys Thr Arg Gly
 85              90                       95

TGT CTC ATC TGT CTT TCA AAG ATC AAG TGT ACA GCA  324
Cys Leu Ile Cys Leu Ser Lys Ile Lys Cys Thr Ala
            100                 105

AAA ATG AAG GTG TAC ATT CCA GGA AGA TGT CAT GAT  360
Lys Met Lys Val Tyr Ile Pro Gly Arg Cys His Asp
        110                 115                 120

TAT GGC GGT GAC AAG AAA ACT GGA CAG GCA GGA ATA  396
Tyr Gly Gly Asp Lys Lys Thr Gly Gln Ala Gly Ile
                125                 130

GTT GGT GCC ATT GTT GAC ATT CCC GAA ATT TCT GGA  432
Val Gly Ala Ile Val Asp Ile Pro Glu Ile Ser Gly
        135                 140

TTC AAG GAG TTG GGA CCC ATG GAG CAG TTT ATT GCT  468
Phe Lys Glu Leu Gly Pro Met Glu Gln Phe Ile Ala
145                 150                 155

CAA GTT GAT CTT TGC GCT GAC TGC ACA ACT GGC TGC  504
Gln Val Asp Leu Cys Ala Asp Cys Thr Thr Gly Cys
            160                 165

CTC AAA GGT CTT GCC AAT GTC AAG TGC TCC GCA CTC  540
Leu Lys Gly Leu Ala Asn Val Lys Cys Ser Ala Leu
    170                 175                 180

CTG AAG AAA TGG CTT CCA GAC AGA TGT GCA AGT TTT  576
Leu Lys Lys Trp Leu Pro Asp Arg Cys Ala Ser Phe
            185                 190

GCT GAC AAA ATC CAG AGT GAA GTA GAC AAC ATC AAG  612
Ala Asp Lys Ile Gln Ser Glu Val Asp Asn Ile Lys
        195                 200

GGC TTG GCT GGA GAT CGT TGA                       633
Gly Leu Ala Gly Asp Arg  *
205                210
```

On the other hand, a gene encoding a luciferase protein from *M. pacifica* according to the second embodiment of the present invention is a gene encoding a luciferase protein: luciferase 2 from *M. pacifica*, characterized in that the gene is a DNA molecule having a nucleotide sequence comprising a nucleotide sequence encoding the following full-length amino acid sequence (SEQ ID NO: 3) of the luciferase protein: luciferase 2 from *M. pacifica*.

```
Met Gly Val Lys Leu Ile Phe Ala Val Val Cys Val
 1               5                          10

Ala Ala Ala Gln Ala Ala Thr Ile Asn Glu Asn Phe
            15                  20

Glu Asp Ile Asp Leu Val Ala Ile Gly Gly Ser Phe
 25                  30                  35

Ala Leu Asp Val Asp Ala Asn Arg Gly Gly His Gly
            40                  45

Gly His Pro Gly Lys Lys Met Pro Lys Glu Val Leu
 50                  55                      60

Val Glu Met Glu Ala Asn Ala Lys Arg Ala Gly Cys
            65                  70

His Arg Gly Cys Leu Ile Cys Leu Ser His Ile Lys
        75                  80

Cys Thr Lys Lys Met Lys Lys Phe Ile Pro Gly Arg
 85                  90                  95

Cys His Ser Tyr Glu Gly Asp Lys Asp Ser Ala Gln
            100                 105

Gly Gly Ile Gly Glu Glu Ile Val Asp Met Pro Glu
    110                 115                 120

Ile Pro Gly Phe Lys Asp Lys Glu Pro Met Asp Gln
                125                 130

Phe Ile Ala Gln Val Asp Leu Cys Val Asp Cys Thr
        135                 140

Thr Gly Cys Leu Lys Gly Leu Ala Asn Val His Cys
145                 150                     155

Ser Asp Leu Leu Lys Lys Trp Leu Pro Ser Arg Cys
            160                 165

Lys Thr Phe Ala Ser Lys Ile Gln Ser Gln Val Asp
    170                 175                 180

Thr Ile Lys Gly Leu Ala Gly Asp Arg
            185
```

In this context, it is preferred that the nucleotide sequence encoding the full-length amino acid sequence (SEQ ID NO: 3) of the luciferase protein: luciferase 2 from *M. pacifica* be the following nucleotide sequence (SEQ ID NO: 4).

```
ATG GGA GTC AAA CTT ATC TTT GCT GTT GTT TGT GTT    36
Met Gly Val Lys Leu Ile Phe Ala Val Val Cys Val
 1               5                          10

GCC GCG GCC CAG GCT GCC ACA ATC AAT GAA AAC TTT    72
Ala Ala Ala Gln Ala Ala Thr Ile Asn Glu Asn Phe
            15                  20

GAA GAC ATT GAT CTT GTA GCT ATA GGT GGC AGC TTT   108
Glu Asp Ile Asp Leu Val Ala Ile Gly Gly Ser Phe
 25                  30                  35

GCT CTG GAT GTT GAT GCT AAC AGA GGT GGA CAT GGT   144
Ala Leu Asp Val Asp Ala Asn Arg Gly Gly His Gly
            40                  45

GGA CAT CCT GGC AAG AAG ATG CCA AAA GAA GTA CCT   180
Gly His Pro Gly Lys Lys Met Pro Lys Glu Val Leu
 50                  55                      60

GTT GAA ATG GAA GCT AAT GCT AAA AGG GCT GGG TGC   216
Val Glu Met Glu Ala Asn Ala Lys Arg Ala Gly Cys
            65                  70

CAC AGA GGA TGT CTG ATT TGT CTT TCC CAC ATC AAG   252
His Arg Gly Cys Leu Ile Cys Leu Ser His Ile Lys
        75                  80

TGC ACC AAG AAA ATG AAG AAG TTT ATC CCA GGA AGA   288
Cys Thr Lys Lys Met Lys Lys Phe Ile Pro Gly Arg
 85                  90                  95

TGC CAC AGT TAT GAA GGA GAC AAG GAT TCT GCA CAG   324
Cys His Ser Tyr Glu Gly Asp Lys Asp Ser Ala Gln
            100                 105

GGA GGC ATT GGA GAA GAA ATT GTT GAC ATG CCT GAA   360
Gly Gly Ile Gly Glu Glu Ile Val Asp Met Pro Glu
    110                 115                 120

ATT CCC GGA TTC AAA GAC AAG GAA CCA ATG GAC CAA   396
Ile Pro Gly Phe Lys Asp Lys Glu Pro Met Asp Gln
                125                 130

TTC ATC GCT CAA GTT GAT CTC TGC GTA GAT TGC ACA   432
Phe Ile Ala Gln Val Asp Leu Cys Val Asp Cys Thr
        135                 140

ACT GGA TGC CTC AAG GGT CTT GCC AAT GTC CAT TGC   468
Thr Gly Cys Leu Lys Gly Leu Ala Asn Val His Cys
145                 150                     155

TCT GAT CTC CTG AAG AAA TGG CTT CCT TCA AGA TGC   504
Ser Asp Leu Leu Lys Lys Trp Leu Pro Ser Arg Cys
            160                 165

AAG ACA TTT GCT TCC AAA ATT CAA TCT CAA GTG GAT   540
Lys Thr Phe Ala Ser Lys Ile Gln Ser Gln Val Asp
    170                 175                 180

ACC ATC AAG GGA TTA GCT GGA GAT CGT TGA           570
Thr Ile Lys Gly Leu Ala Gly Asp Arg  *
            185
```

For example, the gene may be a DNA molecule having the following nucleotide sequence (SEQ ID NO: 6) as the nucleotide sequence comprising the nucleotide sequence encoding the full-length amino acid sequence (SEQ ID NO: 2) of the luciferase protein: luciferase 2 from *M. pacifica*.

```
GAGTCCAAAC TGAAAGGTAC TCAAAA                       26

ATG GGA GTC AAA CTT ATC TTT GCT GTT GTT TGT GTT    62
Met Gly Val Lys Leu Ile Phe Ala Val Val Cys Val
 1               5                          10

GCC GCG GCC CAG GCT GCC ACA ATC AAT GAA AAC TTT    98
Ala Ala Ala Gln Ala Ala Thr Ile Asn Glu Asn Phe
            15                  20

GAA GAC ATT GAT CTT GTA GCT ATA GGT GGC AGC TTT   134
```

-continued

```
                Glu Asp Ile Asp Leu Val Ala Ile Gly Gly Ser Phe
                 25                  30                  35

GCT CTG GAT GTT GAT GCT AAC AGA GGT GGA CAT GGT                 170
Ala Leu Asp Val Asp Ala Asn Arg Gly Gly His Gly
             40                  45

GGA CAT CCT GGC AAG AAG ATG CCA AAA GAA GTA CCT                 206
Gly His Pro Gly Lys Lys Met Pro Lys Glu Val Leu
     50                  55                  60

GTT GAA ATG GAA GCT AAT GCT AAA AGG GCT GGG TGC                 242
Val Glu Met Glu Ala Asn Ala Lys Arg Ala Gly Cys
                 65                  70

CAC AGA GGA TGT CTG ATT TGT CTT TCC CAC ATC AAG                 278
His Arg Gly Cys Leu Ile Cys Leu Ser His Ile Lys
         75                  80

TGC ACC AAG AAA ATG AAG AAG TTT ATC CCA GGA AGA                 314
Cys Thr Lys Lys Met Lys Lys Phe Ile Pro Gly Arg
 85                  90                  95

TGC CAC AGT TAT GAA GGA GAC AAG GAT TCT GCA CAG                 350
Cys His Ser Tyr Glu Gly Asp Lys Asp Ser Ala Gln
             100                 105

GGA GGC ATT GGA GAA GAA ATT GTT GAC ATG CCT GAA                 386
Gly Gly Ile Gly Glu Glu Ile Val Asp Met Pro Glu
     110                 115                 120

ATT CCC GGA TTC AAA GAC AAG GAA CCA ATG GAC CAA                 422
Ile Pro Gly Phe Lys Asp Lys Glu Pro Met Asp Gln
                 125                 130

TTC ATC GCT CAA GTT GAT CTC TGC GTA GAT TGC ACA                 458
Phe Ile Ala Gln Val Asp Leu Cys Val Asp Cys Thr
         135                 140

ACT GGA TGC CTC AAG GGT CTT GCC AAT GTC CAT TGC                 494
Thr Gly Cys Leu Lys Gly Leu Ala Asn Val His Cys
145                 150                 155

TCT GAT CTC CTG AAG AAA TGG CTT CCT TCA AGA TGC                 530
Ser Asp Leu Leu Lys Lys Trp Leu Pro Ser Arg Cys
             160                 165

AAG ACA TTT GCT TCC AAA ATT CAA TCT CAA GTG GAT                 566
Lys Thr Phe Ala Ser Lys Ile Gln Ser Gln Val Asp
     170                 175                 180

ACC ATC AAG GGA TTA GCT GGA GAT CGT TGA                         596
Thr Ile Lys Gly Leu Ala Gly Asp Arg  *
                 185

GGGATAAAAA AATGGATAAT TTGATGATGA TACTTTAGCC CAATGATGTT          646

AAAAATGGCC ATTTTCGTAT TAAACCATAA CTATGTAAAA ATGTAATGTA          696

TGCAAATAAA AAAACCTTA ACGGTTTAAA AAAAAAAAAA AAAAAAAAAA           746

AAAAAAA                                                         753
```

The present invention further provides even the invention of use of the genes encoding aforementioned novel luciferase proteins.

That is to say, the invention of use of the genes encoding luciferase proteins from *M. pacifica* according to the present invention is Use of DNA having a nucleotide sequence represented by any of SEQ ID NOs: 2, 4, 9, and 10 as a nucleotide sequence encoding a peptide chain having an amino acid sequence represented by any of SEQ ID NOs: 1, 3, 7, and 8, wherein the use of DNA is aimed at allowing a mammal cell in an in-vitro culture system thereof to recombinantly express therein a luciferase protein whose full-length amino acid sequence is the amino acid sequence represented by any of SEQ ID NOs: 1, 3, 7, and 8 in order to utilize the luciferase protein as a reporter protein which is produced in a secreted luciferase form to be secreted to the outside of the mammal cell. Particularly preferable is such the use of DNA in which said mammal cell is a cell line from human that is culturable in vitro.

BRIEF DESCRIPTION OF THE DRAWINGS

FIG. 1 shows a result of microscopically observing, under ultraviolet irradiation, the outer shape of marine plankton *Metridia pacifica* serving as an origin of novel luciferase proteins according to the present invention.

FIG. 4 shows increases in the luminescent activity of mature *M. pacifica* luciferase 1 that was secreted to a medium by procedures wherein a HeLa cell, which has undergone recovery treatment for cell injury after the introduction of an expression vector White luc1-10/pcDNA3.2 thereinto, was cultured in the medium to induce recombinant expression thereof.

FIG. 5 shows the comparison in amino acid sequence between the luciferase protein from *Metridia pacifica* according to the present invention and luciferase from *Metridia longa* or from *Gaussia princeps*, and shows the comparison between the *Metridia pacifica* luciferase 1 and the luciferase from *Metridia longa* in the upper column and the comparison between the *Metridia pacifica* luciferase 2 and the luciferase from *Gaussia princeps* in the lower column.

FIG. 6 shows the comparison between the amino acid sequences of luciferases from *Metridia longa* and from *Gaussia princeps* and the comparison between nucleotide sequences encoding the amino acid sequences, and also shows 4 types of regions that were selected based on partial amino acid sequences identical between them and coding nucleotide sequences thereof and serve as a basis for mixed primer design.

BEST MODE FOR CARRYING OUT THE INVENTION

Figure 2:
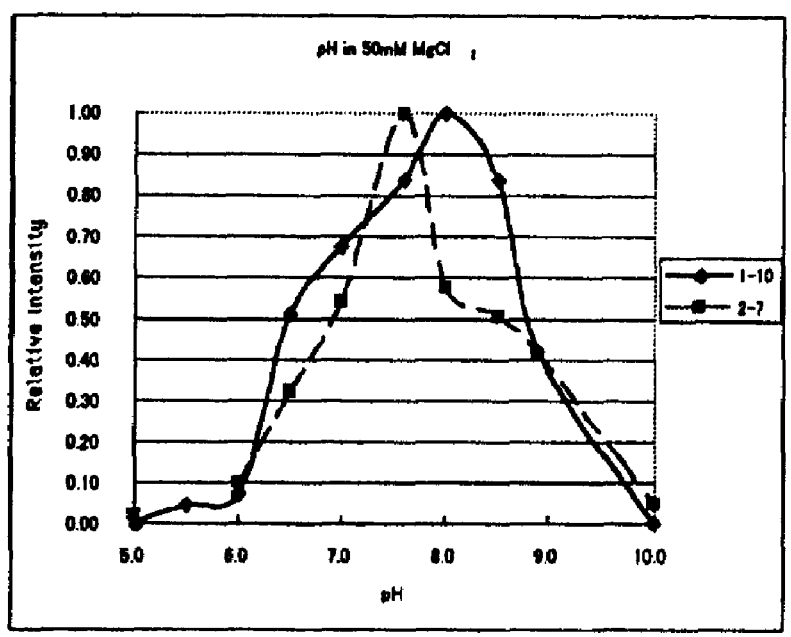
FIG. 2 shows the pH dependency of the luminescent activities of recombinantly expressed proteins of *Metridia pacifica* luciferase 1 and *Metridia pacifica* luciferase 2, which are both recombinantly expressed from the genes encoding luciferase proteins from *Metridia pacifica* according to the present invention, and shows a result of plotting, against pH values adjusted with a variety of buffer solutions, blue luminescences (luminescence intensity measured at a wavelength of 480 nm) emitted from a luminescent substrate coelenterazine by the actions of the recombinantly expressed luciferase proteins at the pHs adjusted with a variety of buffer solutions.

The use of genes encoding luciferase proteins from *Metridia pacifica* of the present invention enables the recombinant expression of the luciferase proteins as proteins having natural luminescent properties and having proper three-dimensional structures in a variety of host cells. Moreover, the recombinantly expressed luciferases from *Metridia pacifica* can emit blue luminescence with the maximum wavelength λmax=480 nm through the oxidation of a luminescent substrate coelenterazine using molecular oxygen in the presence of metal cations, for example, alkali metal cations ($K^+$ and $Na^+$) and alkaline earth metal cations ($Ca^{2+}$ and $Mg^{2+}$), necessary for exerting their luminescent properties. Particularly, the genes encoding luciferase proteins from *Metridia pacifica*, when recombinantly expressed in in-vitro cell culture systems using mammal cells, for example, human cells, have the advantage of being produced as secreted luciferases to the outside of the host mammal cells by use of signal peptides located at the N-terminal portions of the full-length amino acid sequences thereof. That is to say, the luciferase proteins from *Metridia pacifica* can be utilized as reporter proteins that will be secreted to the outside of host cells by constructing recombinant expression systems of mammal cells using the genes encoding luciferase proteins from *Metridia pacifica* of the present invention.

Hereinafter, the genes encoding luciferase proteins from *Metridia pacifica* of the present invention and novel luciferase proteins encoded by the genes will be explained more specifically.

First, zooplankton serving as an origin of two types of novel secreted luciferase proteins according to the present invention is crustacean plankton that has been found in deep ocean water collected from the sea near Japan. The plankton is one species of White Copepoda (red copepods) having a form microscopically observed to be white under white light irradiation. On the other hand, the plankton exhibits an outer shape shown in FIG. 1, when microscopically observed under ultraviolet irradiation. Furthermore, the crustacean plankton was found to produce luciferase that uses coelenterazine as a luminescent substrate, particularly, to produce externally secreted luciferase that is secreted from shell glands present in the exoskeleton (carapace) of the surface of the plankton body to the outside of the plankton body.

The White Copepoda having the ability to produce the externally secreted luciferase was identified in terms of detailed taxonomy and, in conclusion, is *Metridia pacifica* belonging to the genus *Metridia*, family Metridimidae, order Calanoida, superorder Gymnoplea, infraclass Neocopepoda, subclass Copepoda, class Maxillopoda, subphylum Crustacea, phylum Arthropoda, and kingdom Metazoa.

After that, prior to the cloning of genes encoding luciferase proteins from *Metridia pacifica*, mixed primers used in the cloning process were designed.

Since *M. pacifica* was confirmed to produce externally secreted luciferase, a search was conducted on known externally secreted luciferases reported about marine plankton also belonging to *Metridia*. As a result, luciferase from *Metridia longa* (GenBank™/EBI accession number AY364164; J. Biol. Chem. Vol. 279, No. 5 pp. 3212-3217 (2004)) was found. Furthermore, reported cases of luciferases from crustacean plankton belonging to Metridimidae were seeked for. As a result, luciferase from *Gaussia princeps* belonging to the genus *Gaussia* (GenBank™/EBI accession number AY015993) and luciferase from *Pleuromamma* sp. CSG-2001 belonging to the genus *Pleuromamma* (GenBank™/EBI accession number AY015993) were hit.

The three types of searched luciferases from the crustacean planktons belonging to Metridimidae were compared in their amino acid sequences. However, a highly conserved "consensus sequence" was not found among the three types of luciferases. Next, the luciferase from *Metridia longa* and each of the other two types of luciferases were compared in their amino acid sequences. As a result, the presence of regions highly homologous between the luciferase from *Metridia longa* and the luciferase from *Gaussia princeps* was found.

This result suggests that the luciferase from *Metridia longa* and the luciferase from *Gaussia princeps* may evolutionarily have the same origins. There were found no confirmatory basis to ascertain whether or not the luciferase from *M. pacifica* evolutionarily has the same origin as the other two types of luciferases, but such possibility was hypothetically assumed without any grounds. Designing of mixed primers that provide for PCR products by using, as templates, at least genes of the luciferases from *Metridia longa* and from *Gaussia princeps* were attempted on the assumption.

Figure 6:
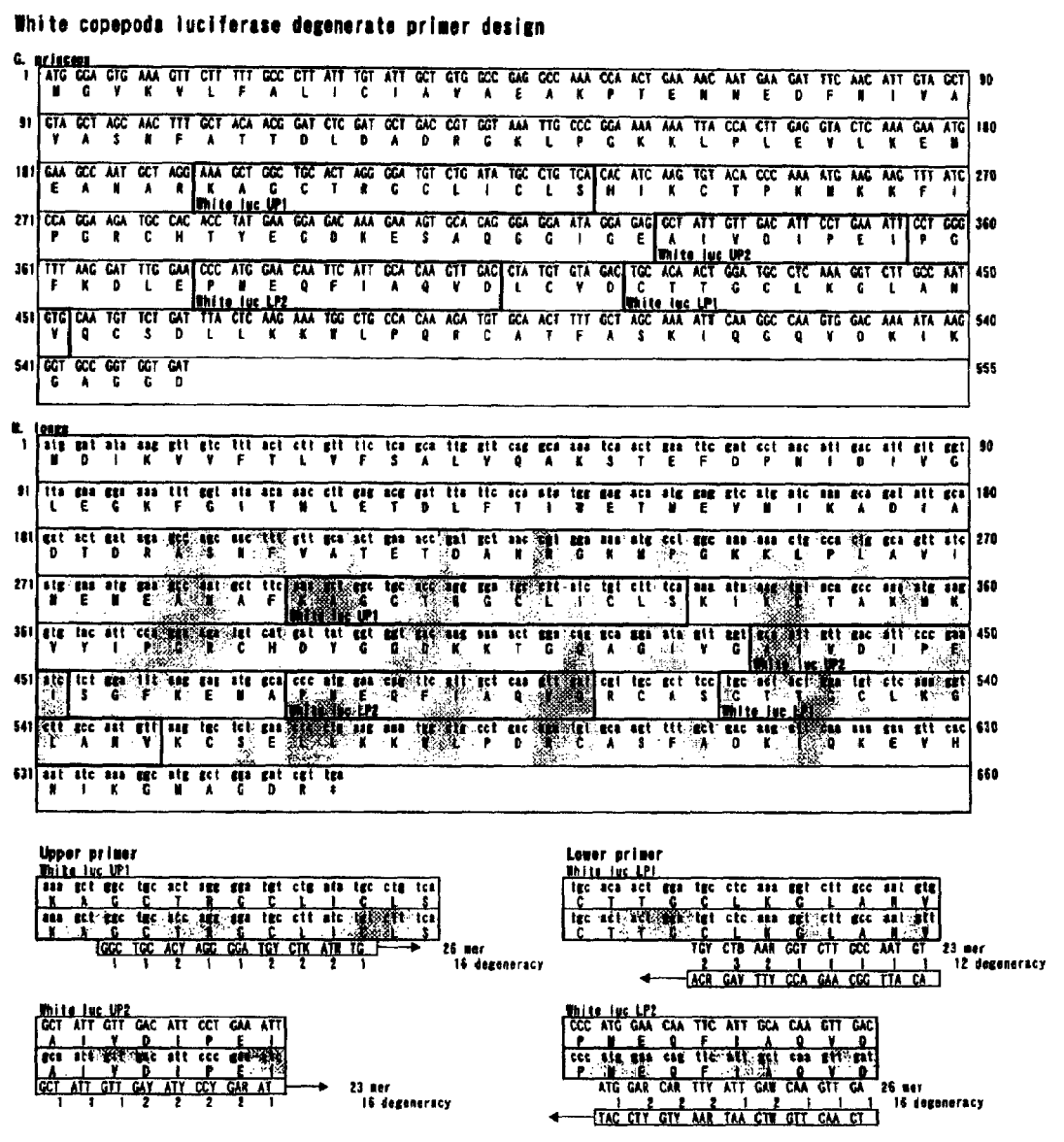

When a search was conducted for regions having partial amino acid sequences identical over 8 or more amino acid residues in the mutual alignment between the amino acid sequences of the luciferases from *Metridia longa* and from *Gaussia princeps*, 4 partial amino acid sequences in total were found, as shown in FIG. 6. With reference to nucleotide sequences encoding these 4 partial amino acid sequences, two types of upstream mixed primers and two types of downstream mixed primers were designed so that cDNAs prepared form mRNAs encoding the luciferases from *Metridia longa* and from *Gaussia princeps* were used as templates to obtain one type of corresponding PCR amplification product for each of them. That is to say, the nucleotide sequence of each mixed primer was selected so that the mixed primer was capable of hybridizing to the region serving as a basis for its design on the cDNA nucleotide sequence but, when misfittingly hybridizing to the other regions, did not permit for DNA strand extension from the 3' terminus of the mixed primer.

In particular, the nucleotide sequences of two types of upstream mixed primers and two types of downstream mixed primers shown below were selected.

Upstream Mixed Primers:

```
White luc UP1 (26 mer: mixed primer of 16
degeneracy)
5'-GGC TGC ACY AGG GGA TGY CTK ATM TC-3'

(Y = T, C; K = G, T; M = A, C)

White luc UP2 (23 mer: mixed primer of 16
degeneracy)
5'-GCT ATT GTT GAY ATY CCY GAR AT-3'

(Y = T, C; R = G, A)
```

Downstream Mixed Primers:

```
White luc LP2 (26 mer: mixed primer of 16
degeneracy)
5'-TC AAG TTG WTC AAT RAA YTG YTC CAT-3'

(W = A, T; R = G, A; Y = T, C)

White luc LP1 (23 mer: mixed primer of 12
degeneracy)
5'-AC ATT GGC AAG ACC YTT VAG RCA-3'

(Y = T, C; V = A, G, C; R = G, A)
```

In the cloning process of genes encoding luciferases from *Metridia pacifica* described below, selected genes offer PCR amplification products for all primer pairs in PCR reaction using, as templates, cDNAs prepared from mRNAs and 4 types in total of PCR primer pairs combined from the two types of upstream mixed primers and the two types of downstream mixed primers. Specifically, the selected genes encoding proteins from *Metridia pacifica* have nucleotide sequences exceedingly highly homologous at least at 4 areas with genes encoding the luciferases from *Metridia longa* and from *Gaussia princeps*. Furthermore, as a result of attempt of cloning in new cDNA preparation from the mRNAs, two types of genes encoding proteins from *Metridia pacifica* were selected which have nucleotide sequences exceedingly highly homologous at least at 4 areas with genes encoding the luciferases from *Metridia longa* and from *Gaussia princeps*. It was demonstrated that these two types of genes encode the two types of luciferases from *Metridia pacifica* and that two types of proteins recombinantly expressed from the genes in animal cells are both secreted luciferases.

Specifically, two types of genes described below were cloned as genes encoding luciferases expressed from the genes encoding luciferases from *Metridia pacifica*.

Nucleotide Sequence of cDNA Corresponding to mRNA of Luciferase 1 from *Metridia pacifica*:

```
GGAGACAACG GATCCAAAAG GAAAGGAGCT AAATCTACAG TCTAGAAC          48

ATG ATG GAA ATA CAA GTT CTT TTT GCT CTC ATT TGC              84
 M   M   E   I   Q   V   L   F   A   L   I   C

TTT GCA TTG GTG CAG GCC AAT CCA ACT GAA AAC AAA             120
 F   A   L   V   Q   A   N   P   T   E   N   K

GAT GAC ATT GAC ATT GTT GGT GTA GAA GGA AAA TTT             156
 D   D   I   D   I   V   G   V   E   G   K   F

GGT ACA ACA GAC CTT GAG ACA GAC TTA TTC ACC ATC             192
 G   T   T   D   L   E   T   D   L   F   T   I

GTG GAG GAT ATG AAT GTC ATC AGT AGA GAC ACC AAT             228
 V   E   D   M   N   V   I   S   R   D   T   N

CTA GCC AAC AGT GAT GCT GAC CGC GGT AAA ATG CCT             264
 L   A   N   S   D   A   D   R   G   K   M   P

GGT AAA AAA CTG CCA CTG GAG GTA CTC ATA GAG ATG             300
 G   K   K   L   P   L   E   V   L   I   E   M

GAA GCC AAT GCT CGT AAA GCT GGC TGC ACC AGG GGA             336
 E   A   N   A   R   K   A   G   C   T   R   G

TGT CTC ATC TGT CTT TCA AAG ATC AAG TGT ACA GCA             372
 C   L   I   C   L   S   K   I   K   C   T   A

AAA ATG AAG GTG TAC ATT CCA GGA AGA TGT CAT GAT             408
 K   M   K   V   Y   I   P   G   R   C   H   D
```

```
-continued

TAT GGC GGT GAC AAG AAA ACT GGA CAG GCA GGA ATA          444
 Y   G   G   D   K   K   T   G   Q   A   G   I

GTT GGT GCC ATT GTT GAC ATT CCC GAA ATT TCT GGA          480
 V   G   A   I   V   D   I   P   E   I   S   G

TTC AAG GAG TTG GGA CCC ATG GAG CAG TTT ATT GCT          516
 F   K   E   L   G   P   M   E   Q   F   I   A

CAA GTT GAT CTT TGC GCT GAC TGC ACA ACT GGC TGC          552
 Q   V   D   L   C   A   D   C   T   T   G   C

CTC AAA GGT CTT GCC AAT GTC AAG TGC TCC GCA CTC          588
 L   K   G   L   A   N   V   K   C   S   A   L

CTG AAG AAA TGG CTT CCA GAC AGA TGT GCA AGT TTT          624
 L   K   K   W   L   P   D   R   C   A   S   F

GCT GAC AAA ATC CAG AGT GAA GTA GAC AAC ATC AAG          660
 A   D   K   I   Q   S   E   V   D   N   I   K

GGC TTG GCT GGA GAT CGT TGA                              681
 G   L   A   G   D   R   *

ATAAACCTGA CAGAACAGAA CAAGAGATAA CTGGATCATG ATATGCTTGA   731

CTCATGCTAA AAAAGTGGCC ATTTTTTGT CAAACAGAAT GAAATTAAAA    781

TATTGAATTG TTTATTAATA TGAATGGAAT TCCTATAAAT ATATTCTATG   831

TAATCCAAAA AAAAAAAAAA AAAAAAAAAA AAAAAG                  867
```

Nucleotide Sequence of cDNA Corresponding to mRNA of Luciferase 2 from *Metridia pacifica*:

```
GAGTCCAAAC TGAAAGGTAC TCAAAA                             26

ATG GGA GTC AAA CTT ATC TTT GCT GTT GTT TGT GTT          62
 M   G   V   K   L   I   F   A   V   V   C   V

GCC GCG GCC CAG GCT GCC ACA ATC AAT GAA AAC TTT          98
 A   A   A   Q   A   A   T   I   N   E   N   F

GAA GAC ATT GAT CTT GTA GCT ATA GGT GGC AGC TTT          134
 E   D   I   D   L   V   A   I   G   G   S   F

GCT CTG GAT GTT GAT GCT AAC AGA GGT GGA CAT GGT          170
 A   L   D   V   D   A   N   R   G   G   H   G

GGA CAT CCT GGC AAG AAG ATG CCA AAA GAA GTA CCT          206
 G   H   P   G   K   K   M   P   K   E   V   L

GTT GAA ATG GAA GCT AAT GCT AAA AGG GCT GGG TGC          242
 V   E   M   E   A   N   A   K   R   A   G   C

CAC AGA GGA TGT CTG ATT TGT CTT TCC CAC ATC AAG          278
 H   R   G   C   L   I   C   L   S   H   I   K

TGC ACC AAG AAA ATG AAG AAG TTT ATC CCA GGA AGA          314
 C   T   K   K   M   K   K   F   I   P   G   R

TGC CAC AGT TAT GAA GGA GAC AAG GAT TCT GCA CAG          350
 C   H   S   Y   E   G   D   K   D   S   A   Q

GGA GGC ATT GGA GAA GAA ATT GTT GAC ATG CCT GAA          386
 G   G   I   G   E   E   I   V   D   M   P   E

ATT CCC GGA TTC AAA GAC AAG GAA CCA ATG GAC CAA          422
 I   P   G   F   K   D   K   E   P   M   D   Q

TTC ATC GCT CAA GTT GAT CTC TGC GTA GAT TGC ACA          458
 F   I   A   Q   V   D   L   C   V   D   C   T

ACT GGA TGC CTC AAG GGT CTT GCC AAT GTC CAT TGC          494
 T   G   C   L   K   G   L   A   N   V   H   C
```

```
-continued
TCT GAT CTC CTG AAG AAA TGG CTT CCT TCA AGA TGC           530
 S   D   L   L   K   K   W   L   P   S   R   C AAG ACA TTT GCT TCC AAA ATT CAA TCT CAA GTG GAT           566
 K   T   F   A   S   K   I   Q   S   Q   V   D ACC ATC AAG GGA TTA GCT GGA GAT CGT TGA                   596
 T   I   K   G   L   A   G   D   R   *

GGGATAAAAA AATGGATAAT TTGATGATGA TACTTTAGCC CAATGATGTT    646

AAAAATGGCC ATTTTCGTAT TAAACCATAA CTATGTAAAA ATGTAATGTA    696

TGCAAATAAA AAAAACCTTA ACGGTTTAAA AAAAAAAAAA AAAAAAAAAA    746

AAAAAAA                                                   753
```

In the nucleotide sequences shown above, sites are underlined which are respectively hybridized by the upstream mixed primers White luc UP1 and White luc UP2 and the downstream mixed primers White luc LP2 and White luc LP1 utilized in primary screening.

When the full-length amino acid sequences encoded by the genes are compared between the two types of luciferase proteins, i.e. luciferase 1 and luciferase 2, from *Metridia pacifica* according to the present invention and the luciferases from *Metridia longa* and *Gaussia princeps* belonging to Metridimidae, considerably high homology was found as shown in FIG. 5, which includes amino acid residues showing identity or homologous between the luciferase 1 and the luciferase from *Metridia longa* and between the luciferase 2 and the luciferase from *Gaussia princeps*. Particularly, extremely high homology is shown between the sequence subsequent from the $65^{th}$ amino acid of Asp downward of the luciferase 1 and the sequence subsequent from the $74^{th}$ amino acid of Asp downward of the luciferase from *Metridia longa* and between the sequence subsequent to the $40^{th}$ amino acid of Asp downward of the luciferase 2 and the sequence subsequent from the $40^{th}$ amino acid of Asp downward of the luciferase from *Gaussia princeps*. Hence, It is deduced from this result that the two types of luciferases from *Metridia pacifica* according to the present invention have an origin of the same species as the luciferases from *Metridia longa* and from *Gaussia princeps*, and however, two lines of luciferases having partial difference in amino acid sequence, which are divided with evolution, are coexistently expressed in *Metridia pacifica*. In addition, high homology is shown between the sequence on the N-terminal side from the $22^{nd}$ amino acid of Glu of the luciferase 1 and the sequence on the N-terminal side from the $21^{st}$ amino acid of Glu of the luciferase from *Metridia longa* and between the sequence on the N-terminal side from the $23^{rd}$ amino acid of Asn of the luciferase 2 and the sequence on the N-terminal side from the $23^{rd}$ amino acid of Asn of the luciferase from *Gaussia princeps*. These sequences on the N-terminal side are regions containing signal peptides used for secretion. A predicted cleavage site for signal peptidase is VQA-KS in the luciferase from *Metridia longa*, while a site corresponding thereto is VQA-NP in the luciferase 1. This site may correspond to AEA-KP in the luciferase from *Gaussia princeps* and AQA-AT in the luciferase 1. Taking the homology into consideration, the two types of luciferases from *Metridia pacifica* according to the present invention, when recombinantly expressed in mammal cells, are also secreted to the outside of the host cells with high efficiency by use of the N-terminal signal peptides rich in hydrophobic amino acids.

Besides, two types of recombinant expression vectors in which each of the genes (cDNAs) encoding the two types of luciferases, luciferase 1 and luciferase 2, from *Metridia pacifica* according to the present invention was inserted into the multicloning site of a plasmid vector pcDNA3.2/V5-GW/D-TOPO have been deposited internationally (December 6, Heisei 16 (2004)) as deposition No. FERM BP-10179 for the recombinant expression vector pMpLuc1-10 for the luciferase 1 and as deposition No. FERM BP-10178 for the recombinant expression vector pMpLuc2-7 for the luciferase 2 with International Patent Organism Depositary, National Institute of Advanced Industrial Science and Technology (AIST Tsukuba Central 6, 1-1, Higashi 1-chome, Tsukuba-shi, Ibaraki-ken, 305-8566, Japan) under the Budapest treaty.

For the recombinant expression of the luciferases from *M. pacifica* according to the present invention as reporter proteins in mammal cells, expression systems that have been applied to luciferases from *Cypridina* (*Vargula*) *hilgendorfii* belonging to Ostracoda and from *Oplophorus grachlorostris* belonging to Decapoda are utilized, and approaches comprising replacing the coding regions thereof with that of the gene in questions are available. Alternatively, the luciferases from *M. pacifica* can also be expressed recombinantly in hosts other than the mammal cells that allow for the recombinant expression of conventional luciferase, such as bacteria, yeast, fungi, and insect cells. It is preferred that the genes encoding luciferases from *M. pacifica*, when used in these recombinant expressions, be subjected to codon-conversion to a codon with high usage in hosts as appropriate and then inserted into an expression vector. Of course, any mutations are not introduced in amino acid sequences themselves encoded by the genes resulting from the codon-conversion. For the insertion to an expression vector, the coding genes that have undergone codon-conversion in advance are digested in their both terminal uncoding regions with restriction enzymes to obtain fragments thereof. When there exist no restriction enzyme sites appropriate for this restriction enzyme digestion, a mutation can be introduced in the nucleotide sequence in the uncoding region by site-specific mutagenesis to thereby introduce the desired restriction enzyme site therein.

Examples

Hereinafter, the present invention will be explained specifically with reference to Examples. Although the specific examples shown here are one example of the best modes of the present invention, the scope of the present invention is not limited to these specific examples.

(Picking-Out of Novel Luciferase from Crustacean Plankton)

The present inventors searched crustacean plankton producing luciferases that use coelenterazine as their luminescent substrates, among many species of zooplankton collected from the sea near Japan. The present inventors particularly searched crustacean plankton producing externally secreted luciferase that is secreted from shell glands present in the exoskeleton (carapace) of the surface of the plankton body to the outside of the plankton body.

In the search process, the present inventors conducted the detailed examination of many species of zooplankton present in deep ocean water collected from a depth of 321 m (321 m below the sea surface, approximately 5 m above the sea bottom), approximately 2,600 m off the coast of Toyama Bay, the Sea of Japan, and consequently found that one species of Copepoda microscopically observed to be white under white light irradiation exhibits an outer shape shown in FIG. 1, when microscopically observed under ultraviolet irradiation, and produces externally secreted luciferase that is secreted from its shell glands to the outside of the body. The Copepoda having the ability to produce the externally secreted luciferase was identified in terms of detailed taxonomy and, in conclusion, is *Metridia pacifica* belonging to the genus *Metridia*, family Metridimidae, order Calanoida, superorder Gymnoplea, infraclass Neocopepoda, subclass Copepoda, class Maxillopoda, subphylum Crustacea, phylum Arthropoda, and kingdom Metazoa.

(Mixed Primer Design for Cloning of Gene Encoding Luciferase Protein from *Metridia pacifica*)

Prior to the cloning of genes encoding luciferase proteins from *Metridia pacifica*, mixed primers used in the cloning process were designed.

Since *M. pacifica* was confirmed to produce externally secreted luciferase, a search was conducted on known externally secreted luciferases reported about marine plankton also belonging to *Metridia*. As a result, luciferase from *Metridia longa* (GenBank™/EBI accession number AY364164; J. Biol. Chem. Vol. 279, No. 5 pp. 3212-3217 (2004)) was found. Furthermore, reported cases of luciferases from crustacean plankton belonging to Metridimidae were seeked for. As a result, luciferase from *Gaussia princeps* belonging to the genus *Gaussia* (GenBank™/EBI accession number AY015993) and luciferase from *Pleuromamma* sp. CSG-2001 belonging to the genus *Pleuromamma* (GenBank™/EBI accession number AY015993) were hit.

The three types of searched luciferases from the crustacean planktons belonging to Metridimidae were compared in their amino acid sequences. However, a highly conserved "consensus sequence" was not found among the three types of luciferases. Next, the luciferase from *Metridia longa* and each of the other two types of luciferases were compared in their amino acid sequences. As a result, the presence of regions highly homologous between the luciferase from *Metridia longa* and the luciferase from *Gaussia princeps* was found.

This result suggests that the luciferase from *Metridia longa* and the luciferase from *Gaussia princeps* may evolutionarily have the same origins. There was found no confirmatory evidence to ascertain whether or not the luciferase from *M. pacifica* evolutionarily has the same origin as the other two types of luciferases, but such possibility was hypothetically assumed without any grounds. Designing of mixed primers that provide for PCR products by using, as templates, at least genes of the luciferases from *Metridia longa* and from *Gaussia princeps* were attempted on the assumption.

When a search was conducted for regions having partial amino acid sequences identical over 8 or more amino acid residues in the mutual alignment between the amino acid sequences of the luciferases from *Metridia longa* and from *Gaussia princeps,* 4 partial amino acid sequences in total were found, as shown in FIG. 6. With reference to nucleotide sequences encoding these 4 partial amino acid sequences, two types of upstream mixed primers and two types of downstream mixed primers were designed so that cDNAs prepared form mRNAs encoding the luciferases from *Metridia longa* and from *Gaussia princeps* were used as templates to obtain one type of corresponding PCR amplification product for each of them. Specifically, the nucleotide sequence of each mixed primer was selected so that the mixed primer was capable of hybridizing to the region serving as a basis for its design on the cDNA nucleotide sequence but, when misfittingly hybridizing to the other regions, did not permit for DNA strand extension from the 3' terminus of the mixed primer.

Specifically, the nucleotide sequences of two types of upstream mixed primers and two types of downstream mixed primers shown below were selected.

Upstream Mixed Primers:

```
White luc UP1 (26 mer: mixed primer of 16
degeneracy)
5'-GGC TGC ACY AGG GGA TGY CTK ATM TC-3'

(Y = T, C; K = G, T; M = A, C)

White luc UP2 (23 mer: mixed primer of 16
degeneracy)
5'-GCT ATT GTT GAY ATY CCY GAR AT-3'

(Y = T, C; R = G, A)
```

Downstream Mixed Primers:

```
White luc LP2 (26 mer: mixed primer of 16
degeneracy)
5'-TC AAG TTG WTC AAT RAA YTG YTC CAT-3'

(W = A, T; R = G, A; Y = T, C)

White luc LP1 (23 mer: mixed primer of 12
degeneracy)
5'-AC ATT GGC AAG ACC YTT VAG RCA-3'

(Y = T, C; V = A, G, C; R = G, A)
```

In the cloning process of genes encoding luciferases from *Metridia pacifica* described below, selected genes offer PCR amplification products for all primer pairs in PCR reaction using, as templates, cDNAs prepared from mRNAs and 4 types in total of PCR primer pairs combined from the two types of upstream mixed primers and the two types of downstream mixed primers. Specifically, the selected genes encoding proteins from *Metridia pacifica* have nucleotide sequences extremely highly homologous at least at 4 areas with genes encoding the luciferases from *Metridia longa* and from *Gaussia princeps*.

(Cloning of Gene Encoding Luciferase from *Metridia pacifica*)

Collection of Total RNA

Four hundred individuals of Copepoda (*M. pacifica*) collected from the sampled ocean water were dewatered, then suspended in 4 mL in total of TRIZOL reagent, and frozen to storage at −80° C.

The Copepoda individuals preserved by refrigeration were thawed at room temperature. This suspension was transferred to a 15-mL Teflon homogenizer container and loaded to a homogenizer 10 times to thereby homogenize the outer shells and the cells within the bodies. Subsequently, the cell homogenates were made uniform by 10 treatments using a 5-mL syringe and a 22 G needle, in which they were sent under pressure and thereby passed through the needle.

The obtained uniform homogenates were transferred to a 15-mL Falcon tube and were well shaken for 15 seconds after the addition of 0.8 mL of chloroform per 4 mL of TRIZOL reagent. Then, the solution was left standing at room temperature for 2 to 3 minutes to perform phase separation. The solution was further centrifuged (12,000×g) at 2 to 8° C. for 15 minutes. Approximately 4 mL of the supernatant (aqueous phase) was collected into another 15-mL Falcon tube.

The collected aqueous phase was well mixed after the addition of 2 mL of isopropanol per 4 mL of TRIZOL reagent. The solution was kept at room temperature for 10 minutes to perform alcohol precipitation. Then, the solution was centrifuged (12,000×g) at 2 to 8° C. for 10 minutes. The supernatant was removed, and the pellet (alcohol-precipitated fraction) was collected.

After the addition of 4 mL of 75% ethanol per 4 mL of TRIZOL reagent to the pellet (alcohol-precipitated fraction), the mixture was subjected to vortex so to be well-dispersed and mixed. The dispersed mixture solution was centrifuged (11,000 rpm) at 2 to 8° C. for 10 minutes. The supernatant was removed, and the pellet (alcohol-precipitated fraction) was collected. This washing was repeated twice.

Following the washings, the pellet of precipitated RNA was left at 37° C. for 10 minutes and thereby dried by the evaporation of the residual solvent. The dried pellet of precipitated RNA was left standing for 10 to 20 minutes after the addition of 210 μL of RNase-free water and thereby redissolved to prepare a total RNA sample solution.

An aliquot (5 μL) of the lysate was sampled from 210 μL of the prepared total RNA sample solution, and absorbances at wavelengths of 260 nm, 280 nm, and 320 nm: $OD_{260}$, $OD_{280}$, and $OD_{320}$ (background absorption) were measured for the sample. Based on the results, an RNA concentration contained therein was calculated from the absorbance $OD_{260}$ according to a standard method.

Table 1 shows the evaluation results of the RNA concentration contained in the obtained total RNA samples.

[Table 1]

TABLE 1

| SAMPLE | $OD_{260}$ | $OD_{280}$ | $OD_{320}$ | RNA concentration μg/μL | RNA concentration ng/μL | Gross volume μL | RNA amount μg | $OD_{260}/OD_{280}$ |
|---|---|---|---|---|---|---|---|---|
| *M. pacifica* | | | | 0.872 | 872 | 210 | 183.12 | |

Purification of Poly(a)+RNA (mRNA)

Poly(A)+RNA (mRNA) contained was separated and purified by use of a commercially available purification kit Oligotex-dT30 <SUPER> mRNA Purification Kit (produced by TAKARA) from 205 μL of the thus-prepared purified total RNA solution (RNA concentration: 0.872 μg/μL).

To 200 μL of the total RNA solution, 200 μL of hybridization buffer 2× Binding buffer included in the kit was added, and then total 400 μL of solution was homogenized. This RNA solution was well mixed after the addition of 20 μL of Oligotex-dT30 dispersion. The solution in the tube was heated up to 70° C. and kept for 3 minutes. Subsequently, the solution was allowed to cool down at room temperature for 10 minutes to perform the hybridization of the poly(A) terminal of the poly(A)+RNA (mRNA) with the oligo-dT probe portion of the Oligotex-dT30. The Oligotex-dT30 was separated as a precipitated fraction by centrifugation (15,000 rpm) for 5 minutes. The supernatant was removed which contained RNA components unhybridized with the Oligotex-dT30.

The precipitated fraction was dispersed into 350 μL of washing buffer included in the kit and transferred to a tube for a centrifugation column. The solution was centrifuged (15,000 rpm) for 30 seconds, and the supernatant was removed. The same washing procedure was further performed by use of the same amount of washing buffer.

After twice washings, the precipitated fraction was supplemented with 50 μL of DEPC-water (aqueous solution) included in the kit, which was heated in advance to 70° C. This mixture was transferred to another tube for a centrifugation column. Following centrifugation (15,000 rpm) for 30 seconds, the supernatant was collected which contained poly (A)+RNA (mRNA) released from the Oligotex-dT30 probe. The precipitated fraction was supplemented again with 50 μL of DEPC-water (aqueous solution) heated in advance to 70° C. The releasing procedure from the probe was performed, and the supernatant was collected. The collected supernatants were pooled to prepare 100 μL in total of a solution containing purified mRNA.

To this solution containing purified mRNA, 10 μL of 3 M sodium acetate aqueous solution and 100 μL of 100% isopropanol was added, and then the mixture was well mixed. Then, the mixture was left at −20° C. for 10 minutes to alcohol-precipitate the contained mRNA. The precipitated mRNA was collected into a precipitated fraction by centrifugation (14,000 rpm) for 30 minutes, and the supernatant was removed. To the precipitated fraction containing the separated mRNA, 1 mL of 75% ethanol was again added, and then the mixture was well mixed. The precipitated fraction containing the deposited mRNA was separated by centrifugation (14,000 rpm) for 5 minutes, and the supernatant was removed. The obtained purified mRNA deposit was redissolved in 11 μL of DEPC-water (aqueous solution).

An aliquot (0.5 μL) of an evaluation sample was collected from 11 μL of the purified mRNA sample solution and evaluated for an RNA concentration contained therein. Table 2 shows the evaluation results of the RNA concentration contained in the obtained purified mRNA sample.

[Table 2]

TABLE 2

| SAMPLE | OD$_{260}$ | OD$_{280}$ | OD$_{320}$ | Dilution ratio | RNA concentration μg/μL | Gross volume μL | RNA amount μg | OD$_{260}$/ OD$_{280}$ |
|---|---|---|---|---|---|---|---|---|
| *M. pacifica* | | | | ×200 | 0.525 | 11 | 5.76 | | cDNA Synthesis with Use of mRNA as Template

A commercially available cDNA synthesis kit was used to synthesize cDNA through reverse transcriptase reaction using the purified mRNA as a template.

First, a 5'CDS primer-supplemented mRNA solution (RNA/5'-Ready Primer mix) containing the purified mRNA sample solution, a 5'CDS (cDNA synthesis) primer and SMART II oligo included in the kit as well as a 3'CDS primer-supplemented mRNA solution (RNA/3'-Ready Primer mix) containing the purified mRNA sample solution and a 3'CDS (cDNA synthesis) primer included in the kit was prepared in advance according to composition shown in Table 3 below.

[Table 3]

TABLE 3

| Component | Concentration of undiluted solution | Formulated amount μL | Final concentration | Content |
|---|---|---|---|---|
| Composition of RNA/5'-Ready Primer mix | | | | |
| mRNA solution | 0.525 μg/μL | 1.91 | 0.050 μg/μL | 100 ng |
| SMART II oligo | 10 μM | 0.5 | 0.5 μM | |
| 5'CDS primer | 10 μM | 0.5 | 0.5 μM | 5 ng |
| DEPC-water | | 2.6 | | |
| Total | | 5.5 | | |
| Composition of RNA/3'-Ready Primer mix | | | | |
| mRNA solution | 0.525 μg/μL | 1.91 | 0.050 μg/μL | 100 ng |
| 3'CDS primer | 500 ng/μL | 0.5 | 25.0 ng/μL | 250 ng |
| DEPC-water | | 3.1 | | |
| Total | | 5.5 | | |

The components were mixed and kept at 65° C. for 5 minutes. Then, the obtained mixture solution was cooled on ice for 1 minute. All the mRNAs contained in the mixture solution were converted by the heating to single-stranded RNA molecules.

The nucleotide sequence of the 3'CDS primer (3'-Ready Primer) is

```
3'-Ready Primer (57 mer)
5'-AAGCAGTGGT AACAACGCAG AGTACTTTTT TTTTTTTTTT

TTTTTTTTTT TTTTTVN-3
```

(wherein V means A, G, C; and N means A, C, G, T in said sequence), and it hybridizes at the dT30 portion to the poly (A) terminal of the mRNA.

5' Ready cDNA synthesis and 3' Ready cDNA synthesis were performed by preparing a reverse transcription reaction solution according to composition shown in Table 4 below by use of the 5'CDS primer-supplemented mRNA solution (RNA/5'-Ready Primer mix) or 3'CDS primer-supplemented mRNA solution (RNA/3'-Ready Primer mix) prepared in advance, respectively.

[Table 4]

TABLE 4

Composition of reverse transcription reaction solution

| Component | Concentration of undiluted solution | Formulated amount μL | Final concentration |
|---|---|---|---|
| RNA/primer mix | | 5.5 | |
| 5× RT Buffer | 5× | 2.0 | 1× |
| DTT | 100 mM | 0.5 | 5 mM |
| RNase inhibitor | 40 U/μL | 0.5 | 2 U/μL |
| dNTP mix | 10 mM | 0.5 | 0.5 mM |
| Super Script III | | 1.0 | |
| Total | | 10.0 | |

In the cDNA syntheses, a reverse transcriptase SuperScript III included in the kit was utilized. This reaction solution was subjected to incubation at 50° C. for 1 hour and subsequent incubation at 70° C. for 15 minutes to thereby perform DNA strand extension reaction from the primers hybridized with the template mRNA strands. After the completion of reaction, the reaction solution containing the synthesized cDNA was stored at −20° C.

Acquisition of cDNA Fragment Through RT-PCR Reaction

Four sets of primer pairs shown in Table 5 below were used to prepare PCR amplification products from the 3' Ready cDNA prepared with the mRNA from *M. pacifica* as a template.

[Table 5]

TABLE 5

Primer pair used for RT-PCR reaction

| Primer pair | Upstream primer | Downstream primer | Predicted ranking of product size |
|---|---|---|---|
| Set1 UP1-LP1 | White Luc UP1 (16 degeneracy) | White Luc LP1 (12 degeneracy) | 1 |
| Set2 UP1-LP2 | White Luc UP1 (16 degeneracy) | White Luc LP2 (16 degeneracy) | 2 |
| Set3 UP2-LP1 | White Luc UP2 (16 degeneracy) | White Luc LP1 (12 degeneracy) | 3 |
| Set4 UP2-LP2 | White Luc UP2 (16 degeneracy) | White Luc LP2 (16 degeneracy) | 4 |

Table 6 shows the composition of the reaction solution and the conditions used for PCR amplification reaction.

[Table 6]

TABLE 6

Temperature conditions of PCR reaction:
Apparatus used: Mastercycler Gradient (eppendorf)

| Operation Cycle | Temperature °C. | Time | |
|---|---|---|---|
| denature | 96 | 1 min. | |
| anneal | 55 | 10 sec. | |
| extention | 68 | 30 sec. | 35 times |
| denature | 96 | 5 sec. | |
| extention | 68 | 30 sec. | |
| store | 10 | Overnight (14 hours) | |

Composition of PCR reaction solution
DNA polymerase: Advantage 2

| Composition | Concentration of undiluted solution | Formulated amount μL | Final concentration |
|---|---|---|---|
| H₂O | | 9.6 | |
| 10 × Advan 2 Buffer | 10× | 2.0 | 1× |
| dNTP | 2 mM | 2.0 | 0.2 mM |
| Advan 2 Pol | 50 U/μL | 0.4 | 1 U/μL |
| Upstream Primer | 10 μM | 2.0 | 1 μM |
| Downstream Primer | 10 μM | 2.0 | 1 μM |
| cDNA | 10 dil | 2.0 | 1 dil |
| Total | | 20.0 | |

After PCR reaction performed at each reaction solution amount of 20 μL, 5 μL aliquots of the reaction solutions were sampled and electrophoresed on 1% agarose gel to confirm the presence or absence of PCR amplification products and their molecular weights. Table 7 shows the confirmed base number of the PCR amplification product obtained when each primer pair was used.

[Table 7]

TABLE 7

Primer pair used for RT-PCR reaction and
PCR amplification product obtained therewith

| Primer pair | Upstream primer | Downstream primer | Amplified product |
|---|---|---|---|
| Set1 UP1-LP1 | White Luc UP1 (16 degeneracy) | White Luc LP1 (12 degeneracy) | 258 bp |
| Set2 UP1-LP2 | White Luc UP1 (16 degeneracy) | White Luc LP2 (16 degeneracy) | 159 bp |
| Set3 UP2-LP1 | White Luc UP2 (16 degeneracy) | White Luc LP1 (12 degeneracy) | 123 bp |
| Set4 UP2-LP2 | White Luc UP2 (16 degeneracy) | White Luc LP2 (16 degeneracy) | 75 bp |

Based on these results, it was confirmed that the mRNAs from *M. pacifica* include mRNA having a partial nucleotide sequence encoding a partial amino acid sequence similar to those of the luciferases from *M. longa* and from *G. princeps*.

Acquisition of 3' RACE and 5' RACE Reaction Products

The 3' Ready cDNA and 5' Ready cDNA prepared based on the mRNA from *M. pacifica* were used as templates to respectively prepare 3' RACE and 5' RACE reaction products by use of two sets of primer pairs shown in Table 8 below for each of them.

[Table 8]

TABLE 8

| Primer pair | Upstream primer (GS primer) | Downstream primer |
|---|---|---|
| Primer pair used for 3' RACE reaction Template cDNA: 3' Ready cDNA | | |
| Set1 UP1-3' Ready | White Luc UP1 (16 degeneracy) | 3' Ready primer |
| Set2 UP2-3' Ready | White Luc UP2 (16 degeneracy) | 3' Ready primer |
| Primer pair for 5' RACE reaction Template cDNA: 5' Ready cDNA | | |
| Set3 LP1-5' Ready | White Luc LP1 (12 degeneracy) | 5' Ready primer |
| Set4 LP2-5' Ready | White Luc LP2 (16 degeneracy) | 5' Ready primer |

Table 9 shows the composition of the reaction solution and the conditions used for PCR amplification reaction.

[Table 9]

TABLE 9

Temperature conditions used for PCR reaction:
Apparatus used: Mastercycler Gradient (eppendorf)

| Operation cycle | Temperature °C. | Time | |
|---|---|---|---|
| denature | 96 | 1 min. | |
| anneal | 55 | 10 sec. | |
| extention | 68 | 40 sec. | 30 times |
| denature | 96 | 5 sec. | |
| extention | 68 | 40 min. | |
| store | 10 | Overnight (14 hours) | |

Composition of PCR reaction solution
DNA polymerase: Advantage 2

| Composition | Concentration of undiluted solution | Formulated amount μL | Final concentration |
|---|---|---|---|
| H₂O | | 9.6 | |
| 10× Advan 2 Buffer | 10× | 2.0 | 1× |
| dNTP | 2 mM | 2.0 | 0.2 mM |
| Advan 2 Pol | 50 U/μL | 0.4 | 1 U/μL |
| GS Primer | 10 μM | 2.0 | 1 μM |
| Upstream Primer | 10 μM | 2.0 | 1 μM |
| cDNA | 10 dil | 2.0 | 1 dil |
| Total | | 20.0 | |

After PCR reaction performed at each reaction solution amount of 20 μL, 5 μL aliquots of the reaction solutions were sampled and electrophoresed on 1% agarose gel to confirm the presence or absence of PCR amplification products and their molecular weights. Table 10 shows the confirmed base number of the PCR amplification product obtained when each primer pair was used.

[Table 10]

TABLE 10

Primer pair for PCR reaction and
3' RACE and 5' RACE reaction products obtained therewith

| Primer pair | Upstream primer | Downstream primer | Amplified product |
|---|---|---|---|
| Set1 UP1-3' Ready | White Luc UP1 mix | 3' Ready primer | 360 bp |
| Set2 UP2-3' Ready | White Luc UP2 mix | 3' Ready primer | 230 bp |

TABLE 10-continued

Primer pair for PCR reaction and
3' RACE and 5' RACE reaction products obtained
therewith

| Primer pair | Upstream primer | Downstream primer | Amplified product |
|---|---|---|---|
| Set3 LP1-5' Ready | White Luc LP1 mix | 5' Ready primer | 582 bp |
| Set4 LP2-5' Ready | White Luc LP2 mix | 5' Ready primer | 560 bp |

Acquisition of Nested PCR Product Using 3' RACE and 5'-RACE Reaction Products as Templates The 3' RACE and 5' RACE reaction products were used as templates to respectively prepare Nested PCR products by use of each primer pair shown in Table 11 below.

[Table 11]

TABLE 11

| Primer pair | Upstream primer (GS primer) | Downstream primer |
|---|---|---|
| Primer pair used for Nested PCR reaction for 3' RACE reaction product Template cDNA: 3' RACE reaction product (product obtained with use of primer pair Set1 UP1-3' Ready) | | |
| Set1 UP2-3' Ready | White Luc UP2 (16 degeneracy) | 3' Ready primer |
| Primer pair used for Nested PCR reaction for 5' RACE reaction product Template cDNA: 5' RACE reaction product (product obtained with use of primer pair Set3 UP1-5' Ready) | | |
| Set4 LP2-5' Ready | White Luc LP2 (16 degeneracy) | 5' Ready primer |

Table 12 shows the composition of the reaction solution and the conditions of PCR amplification reaction.

[Table 12]

TABLE 12

Temperature conditions of PCR reaction:
Apparatus used: Mastercycler Gradient (eppendorf)

| Operation cycle | Temperature °C. | Time | |
|---|---|---|---|
| denature | 96 | 1 min. | |
| anneal | 60 | 10 sec. | |
| extention | 68 | 30 sec. | 20 times |
| denature | 96 | 5 sec. | |
| extention | 68 | 30 min. | |
| store | 10 | Overnight (14 hours) | |

Composition of PCR reaction solution
DNA polymerase: Advantage 2

| Composition | Concentration of undiluted solution | Formulated amount μL | Final concentration |
|---|---|---|---|
| H$_2$O | | 10.0 | |
| 10× Advan 2 Buffer | 10× | 2.0 | 1× |
| dNTP | 2 mM | 2.0 | 0.2 mM |
| Advan 2 Pol | 50 U/μL | 0.4 | 1 U/μL |
| GS Primer | 10 μM | 1.6 | 0.8 μM |
| Upstream Primer | 10 μM | 2.0 | 1 μM |
| cDNA | 10 dil | 2.0 | 1 dil |
| Total | | 20.0 | |

After PCR reaction performed at each reaction solution amount of 20 μL, 5 μL aliquots of the reaction solutions were collected and electrophoresed on 1% agarose gel to confirm the presence or absence of PCR amplification products and their molecular weights.

The Nested PCR product prepared with use of the 3' RACE reaction product as a template was temporarily inserted into a cloning vector pCR2.1 TOPO, which was then introduced into Chemical competent cell TOP10 strains, and then transformed strains were selected therefrom. The plasmid vector introduction into the host E. coli was performed by procedures described below.

Cryopreserved Competent cells of TOP10 strains used as host E. coli are thawed at an ice temperature. 3 μL of a solution of the plasmid vector with the cDNA insert is added to a 50 μL aliquot of the suspension of the thawed host E. coli Competent cells. Subsequently, the mixture is kept on ice for 10 minutes, then heated at 42° C. for 30 seconds, and returned onto ice again. After the vector injection treatment, 100 μL of SOC medium is added to 53 μL of the host E. coli suspension to be cultured by shaking at 37° C. for 10 minutes.

Then, transformed strains contained in the culture solution are selected with use of the selection marker from the cloning vector pCR2.1 TOPO. From among the selected transformed strains, those carrying the plasmid vector with the cDNA insert are chosen.

Replication and Purification of Plasmid Vector Introduced in Screened Clone

The introduced plasmid vectors are replicated and purified from 4 screened clones by procedures described below.

Each of the four colonies (clones), which were screened from the cDNA-introduced strains using the host E. coli TOP10 strains, was suspended in 10 mL of LB/Carbenicillin medium to be cultured at 37° C. for 16 hours, respectively. The culture solutions were each centrifuged (5000×g) for 10 minutes to fractionate cells therefrom.

The plasmids are separated and purified from the collected cells by use of a commercially available plasmid purification kit QIAGEN plasmid purification kit (produced by QIAGEN). Specifically, 0.25 mL of P1 solution included in the purification kit is added to the collected cells, and then the mixture is subjected to vortex to be well dispersed. To this cell dispersion, 0.25 mL of P2 solution included in the kit is added, and mixed together. The mixture is left standing at room temperature (20° C.) for 5 minutes. Subsequently, to the mixture, 0.35 mL of N3 solution included in the kit is added, and mixed up. Following lysis treatment, centrifugation (11,000 rpm) at 4° C. for 15 minutes is carried out to separate and collect a soluble fraction containing the plasmid DNA (supernatant).

The soluble fraction containing the plasmid DNA (supernatant) is applied to a QIAprep column included in the purification kit. The column is subjected to centrifugation (15,000 rpm) at 4° C. to remove the liquid layer therefrom. The column is washed by the addition of 0.5 mL of buffer PB and subsequently washed by the addition of 0.75 mL of buffer PE. Finally, the washing solution is removed therefrom by centrifugation (15,000 rpm) at 4° C. for 1 minute. The plasmids adsorbed onto the QIAprep of the purification kit are eluted with 30 μL of buffer EB, and then collected therein. Of 30 μL of this solution containing the purified plasmids, a 1 μL aliquot is sampled and added with 99 μL of distilled water to prepare a solution diluted 100-fold thereof.

Table 13 shows results of evaluation of each clone for a DNA concentration contained in the solution containing the purified plasmid.

[Table 13]

TABLE 13

| SAMPLE | OD$_{260}$ | OD$_{280}$ | OD$_{320}$ | Dilution rate | DNA concentration µg/µL | Gross volume µL | DNA amount µg | OD$_{260}$/OD$_{280}$ |
|---|---|---|---|---|---|---|---|---|
| No. 1 | 0.063 | 0.036 | <0.001 | ×100 | 0.340 | 29 | 9.86 | 1.89 |
| No. 3 | 0.050 | 0.025 | <0.001 | ×100 | 0.250 | 29 | 7.25 | 2.00 |
| No. 4 | 0.075 | 0.039 | <0.001 | ×100 | 0.375 | 29 | 10.88 | 1.92 |
| No. 6 | 0.047 | 0.023 | <0.001 | ×100 | 0.240 | 29 | 6.96 | 2.00 |

Nucleotide Sequence Analysis of cDNA Fragment (Nested PCR Product) Contained in Screened Clone From the cDNA portions (Nested PCR products) inserted in the plasmid vectors that are carried by the 4 clones, products of nucleic acid strand extension reaction are prepared for nucleotide sequence analysis thereof according to procedures described below.

The solutions containing the plasmid vectors collected and purified from the screened clones are subjected to concentration adjustment so as to set their DNA concentrations at 250 ng/µL. Subsequently, the purified plasmid vector is used as a template to prepare a sample for nucleotide sequence analysis with use of two types of primers; M13 sense M4 and M13 RV, which are corresponding to the site from the cloning vector pCR2.1 TOPO, as sequencing primers by means of a commercially available sequencing DNA sample preparation kit BigDye Terminator Cycle Sequencing Ready Reaction Kit with AmpliTaq polymerase. Table 14 shows the temperature conditions used for the DNA strand extension reaction and the composition of the reaction solution thereof.

[Table 14]

TABLE 14

| Composition of reaction solution | | |
|---|---|---|
| Component | Concentration of undiluted solution | Ratio of formulated amount µL |
| Terminator Reaction Mix | | 1.0 |
| Template DNA | 250 ng/µL | 2.0 |
| primer | 1 µM | 0.8 |
| DDW | | 1.2 |
| Total | | 5.0 |

| Temperature conditions of DNA strand extension reaction: Apparatus used: Mastercycler Gradient | | | |
|---|---|---|---|
| Operation for temperature cycle | Temperature ° C. | Time | |
| denature | 96 | 1 min. | |
| denature | 96 | 10 sec. | 25 times |
| anneal | 50 | 5 sec. | Ramp. Rate 1° C./s |
| extention | 60 | 4 min. | Ramp. Rate 1° C./s |
| store | 4 | Overnight (14 hours) | |

The prepared samples for nucleotide sequence analysis are purified by procedures described below.

The prepared sample solution is transferred from each reaction tube to another 0.5-mL tube. An additional solution is prepared in advance in a 1.5-mL tube, in such a ratio that 0.5 µL of 3 M sodium acetate aqueous solution and 12.5 µL of 95% ethanol are to be mixed with 5 µL of the sample solution. The sample solution collected in advance is added into this 1.5-mL tube. The solution is uniformly mixed and then left standing under ice cooling for 10 minutes to ethanol-precipitate (deposit) the DNA fragments contained therein. The deposited DNA fragments are sedimented by centrifugation (14,000 rpm) for 20 minutes, and the supernatant is removed therefrom. Subsequently, the deposited DNA fragments are rinsed by the addition of 125 µL of 70% ethanol. The deposited DNA fragments are sedimented again by centrifugation (14,000 rpm) for 5 minutes, and the supernatant is removed by aspiration. The remaining pellets of deposited DNA fragments are dried up.

The purified DNA fragments of sample for analysis are redispersed in Template suppressor Reagent (TSR). The solution is well mixed by vortex and then is subjected to centrifugation to collect a solution therefrom. The solution is heated up at 95° C. for 2 minutes to split the DNA fragments to single-stranded DNA, and cooled on ice. The solution is subjected to vortex once again, and then is centrifugated again to collect the solution containing the extended single-stranded DNA therefrom. Then, the DNA fragments of sample for analysis (extended single-stranded DNA) is loaded to a commercially available sequencing apparatus ABI PRISM 3100 Genetic Analyzer to analyze the nucleotide sequence thereof.

The nucleotide sequence of the inserted cDNA fragment (Nested PCR product) is determined by combining the results of sequencing from the 5' terminus and the results of sequencing from the 3' terminus with each another.

Two types of downstream primers: White luc LP3 and White luc LP4 having nucleotide sequences described below were designed based on the analyzed nucleotide sequence of said Nested PCR product that were prepared with the 3' RACE reaction product as a template:

```
White luc LP3: (30 mer)
5'-AACGATCTCCAGCCAAGCCCTTGATGTTGT-3'

White luc LP4: (30 mer)
5'-TCAGCGCAAAGATCAACTTGAGCAATGAAC-3'
```

Reacquisition of 5' RACE Reaction Product

3' Ready cDNA and 5' Ready cDNA are prepared again based on the mRNA from *M. pacifica*. Then, 5' RACE reaction products are newly prepared by using the 5' Ready cDNA as a template with use of the two types of downstream primers: White luc LP3 and White luc LP4.

First, according to the procedures described in the paragraphs "Collection of total RNA" and "Purification of poly (A)+RNA (mRNA)", total RNAs are separately collected from 900 individuals of *M. Pacifica*, and purified mRNA samples are prepared therefrom. Table 15 shows results of quantifying RNA amounts contained in the collected total RNAs and in the purified mRNA samples.

[Table 15]

TABLE 15

| Total RNA sample | | | | | | | | |
|---|---|---|---|---|---|---|---|---|
| SAMPLE | $OD_{260}$ | $OD_{280}$ | $OD_{320}$ | RNA concentration µg/µL | RNA concentration ng/µL | Gross volume µL | RNA amount µg | $OD_{260}/OD_{280}$ |
| White Copepoda | 0.266 | 0.158 | 0.001 | 1.060 | 1060 | 399 | 422.94 | 1.69 |

| Purified mRNA sample | | | | | | | |
|---|---|---|---|---|---|---|---|
| SAMPLE | $OD_{260}$ | $OD_{280}$ | $OD_{320}$ | Dilution rate | RNA concentration µg/µL | Gross volume µL | RNA amount µg | $OD_{260}/OD_{280}$ |
| White Copepoda | | | | ×200 | 0.728 | 10.5 | 7.64 | |

Subsequently, according to the procedures described in the paragraph "cDNA synthesis with use of mRNA as template", cDNAs are synthesized from the purified mRNA samples through reverse transcriptase reaction using the contained purified mRNAs as templates.

A 5'CDS primer-supplemented mRNA solution (RNA/5'-Ready Primer mix) as well as a 3'CDS primer-supplemented mRNA solution (RNA/3'-Ready Primer mix) is prepared in advance according to composition shown in Table 16 below.

[Table 16]

TABLE 16

| Component | Concentration of undiluted solution | Formulated amount µL | Final concentration | Content |
|---|---|---|---|---|
| Composition of RNA/5'-Ready Primer mix | | | | |
| mRNA solution | 0.728 µg/µL | 1.37 | 0.050 µg/µL | 100 ng |
| SMART II oligo | 10 µM | 0.5 | 0.5 µM | |
| 5'CDS primer | 10 µM | 0.5 | 0.5 µM | 5 ng |
| DEPC-water | | 3.1 | | |
| Total | | 5.5 | | |
| Composition of RNA/3'-Ready Primer mix | | | | |
| mRNA solution | 0.728 µg/µL | 1.37 | 0.050 µg/µL | 100 ng |
| 3'CDS primer | 500 ng/µL | 0.5 | 25.0 ng/µL | 250 ng |
| DEPC-water | | 3.6 | | |
| Total | | 5.5 | | |

The components are mixed and kept at 65° C. for 5 minutes. Then, the obtained mixture solution is cooled on ice for 1 minute. All the mRNAs contained in the mixture solution are converted by the heating to single-stranded RNA molecules.

The synthesis of 5' Ready cDNA and the synthesis 3' Ready cDNA are performed by preparing a reverse transcription reaction solution according to composition shown in Table 17 below with use of the 5'CDS primer-supplemented mRNA solution (RNA/5'-Ready Primer mix) or 3'CDS primer-supplemented mRNA solution (RNA/3'-Ready Primer mix) prepared in advance.

[Table 17]

TABLE 17

| Composition of reverse transcription reaction solution | | | |
|---|---|---|---|
| Component | Concentration of undiluted solution | Formulated amount µL | Final concentration |
| RNA/primer mix | | 5.5 | |
| 5× RT Buffer | 5× | 2.0 | 1× |
| DTT | 100 mM | 0.5 | 5 mM |
| RNase inhibitor | 40 U/µL | 0.5 | 2 U/µL |
| dNTP mix | 10 mM | 0.5 | 0.5 mM |
| Super Script III | | 1.0 | |
| Total | | 10.0 | |

In the cDNA syntheses, this reaction solution is subjected to treatment involving incubation at 50° C. for 1 hour and subsequent incubation at 70° C. for 15 minutes, and thereby DNA strand extension reaction from the primers hybridized with the template mRNA strands is carried out by using a reverse transcriptase SuperScript III included in the kit. After the completion of reaction, the reaction solution containing the synthesized cDNA is stored at −20° C.

The 5' Ready cDNAs newly prepared based on the mRNAs from *M. pacifica* are used as templates to respectively prepare 5' RACE reaction products with use of two sets of primers shown in Table 18 below.

[Table 18]

TABLE 18

| Primer pair for 5' RACE reaction Template cDNA: 5' Ready cDNA | | |
|---|---|---|
| Primer pair | Upstream primer | Downstream primer (GS primer) |
| Set1 LP4-5' Ready | White Luc LP4 | 5' Ready primer |
| Set2 LP3-5' Ready | White Luc LP3 | 5' Ready primer |

Table 19 shows the composition of the reaction solution and the conditions of PCR amplification reaction.

[Table 19]

TABLE 19

Temperature conditions of PCR reaction:
Apparatus used: Mastercycler Gradient (eppendorf)

| Operation Cycle | Temperature ° C. | Time | |
|---|---|---|---|
| denature | 96 | 1 min. | |
| anneal | 60 | 10 sec. | |
| extention | 68 | 50 sec. | 50 times |
| denature | 96 | 5 sec. | |
| extention | 68 | 50 sec. | |
| store | 10 | Overnight (14 hours) | |

Composition of PCR reaction solution
DNA polymerase: Pyrobest DNA polymerase

| Composition | Concentration of undiluted solution | Formulated amount μL | Final concentration |
|---|---|---|---|
| H$_2$O | | 13.75 | |
| 10× Pyro Buffer | 10× | 2.5 | 1× |
| dNTP | 2 mM | 2.5 | 0.2 mM |
| Pyrobest DNA Pol | 5 U/μL | 0.25 | 0.050 U/μL |
| GS Primer | 10 μM | 1.0 | 0.4 μM |
| Upstream Primer | 10 μM | 2.5 | 1 μM |
| cDNA | 10 dil | 2.5 | 1 dil |
| Total | | 25.0 | |

After PCR reaction performed at each reaction solution amount of 25 μL, 5 μL aliquots of the reaction solutions are collected and electrophoresed on 1% agarose gel to confirm the presence or absence of PCR amplification products and their molecular weights. Table 20 shows the base number of the confirmed amplification product obtained with each primer pair.

[Table 20]

TABLE 20

Primer pair used for 5' RACE reaction and 5' RACE reaction product prepared therewith

| Primer pair | Upstream primer | Downstream primer | Amplified product |
|---|---|---|---|
| Set1 UP4-5' Ready | White Luc LP4 | 5' Ready primer | bp |
| Set2 UP3-5' Ready | White Luc UP3 | 5' Ready primer | bp |

The 5' RACE reaction product is temporarily inserted into a cloning vector pCR4Blunt-TOPO (produced by Invitrogen), and then the obtained vector is introduced into Chemical competent cell TOP10 strains to select the transformed strains therefrom. The plasmid vector introduction into the host *E. coli* was performed according to the procedures described above.

After that, transformed strains contained in the culture solution are selected on a drug-supplemented medium with use of the selection marker (drug resistance gene) from the cloning vector pCR4Blunt-TOPO. From among the selected transformed strains, those carrying the plasmid vector with the cDNA insert are selected by means of a colony PCR method.

Screening of Clone Carrying Plasmid Vector with cDNA Insert by Colony PCR Method The presence or absence of cDNA fragment insertion in the plasmid vectors collected from the transformed strains forming each colony is confirmed by means of the colony PCR method according to procedures described below.

In the colony PCR, PCR amplification is performed by using the vector DNA contained in the clone as a template, with use of White luc UP1 (mixed primer) and White luc LP2 (mixed primer) as a forward primer and as a reverse primer, by means of commercially available DNA synthetase KOD Dash DNA polymerase. In this case, selected are such clones that provide a 159-bp DNA fragment as the PCR product obtained with the primer pair; White luc UP1 and White luc LP2, as described above. Table 21 shows the temperature conditions of the PCR reaction used and the composition of the reaction solution thereof.

[Table 21]

TABLE 21

Temperature conditions of PCR reaction:
Apparatus used: Mastercycler (eppendorf)

| Operation cycle | Temperature ° C. | Time | |
|---|---|---|---|
| denature | 96 | 1 min. | |
| anneal | 55 | 5 sec. | |
| extention | 74 | 15 sec. | 25 times |
| denature | 96 | 5 sec. | |
| extention | 74 | 15 sec. | |
| store | 10 | Overnight (14 hours) | |

Composition of reaction solution
DNA polymerase: KOD Dash

| Component | Concentration of undiluted solution | Formulated amount μL | Final concentration |
|---|---|---|---|
| H$_2$O | | 5.8 | |
| Dash Buffer | 10× | 1.0 | 1× |
| dNTP | 2 mM | 1.0 | 0.2 mM |
| KOD Dash | 2.5 U/μL | 0.2 | 0.050 U/μL |
| UP1 primer | 10 μM | 0.5 | 0.5 μM |
| LP2 primer | 10 μM | 0.5 | 0.5 μM |
| Colony soln. | | 1.0 | |
| Total | | 10.0 | |

Forty-eight colonies were randomly selected from the colonies on the Petri dish. The bacterial cells in each colony were suspended in 70 μL of water (DDW). This bacterial cell suspension was treated at 95° C. for 5 minutes. The solution containing the vector collected from the bacterial cells was utilized as a colony solution for the reaction solution.

After the completion of PCR reaction, a 3 μL aliquot is collected from 10 μL of the reaction solution containing the amplified product and electrophoresed on 2% gel to examine the presence or absence of a PCR amplification product corresponding to the cDNA fragment and a size range thereof. The primary screening found out 189-bp expected PCR amplification products in 16 colonies of Nos. 4-7, 10, 18, 22, 24, 25, 27, 29, 31, 33, 35, 36, and 38 among the 48 randomly selected colonies.

Subsequently, secondary screening is carried for the 16 colonies screened in the primary screening by means of colony PCR under conditions shown in Table 22 below.

[Table 22]

TABLE 22

Temperature conditions of PCR reaction:
Apparatus used: Mastercycler (eppendorf)

| Operation cycle | Temperature °C. | Time | |
|---|---|---|---|
| denature | 96 | 1 min. | |
| anneal | 55 | 5 sec. | |
| extention | 74 | 40 sec. | 25 times |
| denature | 96 | 5 sec. | |
| extention | 74 | 40 sec. | |
| store | 10 | Overnight (14 hours) | |

Composition of reaction solution
DNA polymerase: KOD Dash

| Component | Concentration of undiluted solution | Formulated amount μL | Final concentration |
|---|---|---|---|
| $H_2O$ | | 6.4 | |
| Dash Buffer | 10× | 1.0 | 1× |
| dNTP | 2 mM | 1.0 | 0.2 mM |
| KOD Dash | 2.5 U/μL | 0.2 | 0.050 U/μL |
| UP1 primer | 10 μM | 0.2 | 0.2 μM |
| LP2 primer | 10 μM | 0.2 | 0.2 μM |
| Colony soln. | | 1.0 | |
| Total | | 10.0 | |

After the completion of PCR reaction, a 3 μL aliquot is collected from 10 μL of the reaction solution containing the amplified product and electrophoresed on 2% gel to examine the presence or absence of a PCR amplification product corresponding to the cDNA fragment and a size range thereof. This screening found out PCR amplification products having a size corresponding to the cloning site with the cDNA fragment insert in 8 colonies of Nos. 4, 5, 7, 10, 27, 29, 31, and 33 among the 16 colonies screened in the primary screening.

Replication and Purification of Plasmid Vector with 5' RACE Reaction Product Insert Carried by Screened Clone The plasmid vector with the 5' RACE reaction product insert was replicated and purified from the 8 screened clones by procedures described below.

The 8 screened colonies (clones) were separately suspended in 10 mL of LB/Carbenicillin medium and cultured at 37° C. for 15.6 hours. The culture solutions were centrifuged (5000×g) for 10 minutes to collect cells therefrom.

The plasmids were separated and purified from the collected cells by means of a commercially available plasmid purification kit QIAGEN plasmid purification kit (produced by QIAGEN). Specifically, 0.25 mL of P1 solution included in the purification kit was added to the collected cells, and then the mixture was subjected to vortex so as to be well dispersed. To this cell dispersion, 0.25 mL of P2 solution included in the kit was added, and mixed together. The mixture was left standing at room temperature (20° C.) for 5 minutes. Subsequently, to the mixture, 0.35 mL of N3 solution included in the kit was added, and mixed up. Following lysis treatment, centrifugation (11,000 rpm) at 4° C. for 15 minutes was carried out to separate and collect a soluble fraction containing the plasmid DNA (supernatant).

The soluble fraction containing the plasmid DNA (supernatant) was applied to a QIAprep column included in the purification kit. The column was subjected to centrifugation (15,000 rpm) at 4° C. to remove the liquid layer therefrom. The column was washed by the addition of 0.5 mL of buffer PB and subsequently washed by the addition of 0.75 mL of buffer PE. Finally, the washing solution was removed therefrom by centrifugation (15,000 rpm) at 4° C. for 1 minute. The plasmids adsorbed onto the QIAprep of the purification kit were eluted with 30 μL of buffer EB, and then collected therein. Of 30 μL of this solution containing the purified plasmids, a 1 μL aliquot was sampled and added with 99 μL of distilled water to prepare a solution diluted 100-fold thereof.

Table 23 shows results of evaluation of each clone for a DNA concentration contained in the solution containing the purified plasmid.

[Table 23]

TABLE 23

| Sample | $OD_{260}$ | $OD_{280}$ | $OD_{320}$ | Dilution ratio | DNA concentration μg/μl | Gross volume μL | DNA amount μg | $OD_{260}/OD_{280}$ |
|---|---|---|---|---|---|---|---|---|
| No. 4 | 0.042 | 0.023 | <0.001 | ×100 | 0.210 | 29 | 6.09 | 1.83 |
| No. 5 | 0.047 | 0.024 | <0.001 | ×100 | 0.235 | 29 | 6.82 | 1.96 |
| No. 7 | 0.077 | 0.041 | <0.001 | ×100 | 0.385 | 29 | 11.17 | 1.88 |
| No. 10 | 0.064 | 0.034 | <0.001 | ×100 | 0.320 | 29 | 9.28 | 1.88 |
| No. 27 | 0.066 | 0.034 | <0.001 | ×100 | 0.330 | 29 | 9.57 | 1.94 |
| No. 29 | 0.054 | 0.027 | <0.001 | ×100 | 0.270 | 29 | 7.93 | 2.00 |
| No. 31 | 0.050 | 0.026 | <0.001 | ×100 | 0.260 | 29 | 7.54 | 1.86 |
| No. 33 | 0.060 | 0.031 | <0.001 | ×100 | 0.310 | 29 | 8.99 | 1.88 |

Nucleotide Sequence Analysis of cDNA Fragment (5' RACE Reaction Product) in Screened Clone From the cDNA portions (5' RACE reaction products) inserted in the plasmid vectors carried by said 8 clones, products of nucleic acid strand extension reaction were prepared for nucleotide sequence analysis thereof according to procedures described below.

The solutions containing the plasmid vectors collected and purified from the screened clones were subjected to concentration adjustment so as to set their DNA concentrations at 250 ng/μL. Subsequently, the purified plasmid vector was used as a template to prepare a sample for nucleotide sequence analysis with use of two types of primers; M13 sense M4 and M13 RV, which are corresponding to the site from the cloning vector pCR4Blunt-TOPO, as sequencing primers by means of a commercially available sequencing DNA sample preparation kit BigDye Terminator Cycle Sequencing Ready Reaction Kit with AmpliTaq polymerase. Table 24 shows the temperature conditions used for the DNA strand extension reaction and the composition of the reaction solution thereof.

[Table 24]

TABLE 24

| Composition of reaction solution | | |
|---|---|---|
| Component | Concentration of undiluted solution | Ratio of formulated amount μL |
| Terminator Reaction Mix | | 1.0 |
| Template DNA | 250 ng/μL | 2.0 |
| primer | 1 μM | 0.8 |
| DDW | | 1.2 |
| Total | | 5.0 |

| Temperature conditions of DNA strand extension reaction: Apparatus used: Mastercycler Gradient | | | |
|---|---|---|---|
| Operation for temperature cycle | Temperature °C. | Time | |
| denature | 96 | 1 min. | |
| denature | 96 | 10 sec. | 25 times |
| anneal | 50 | 5 sec. | Ramp. Rate 1° C./s |
| extention | 60 | 4 min. | Ramp. Rate 1° C./s |
| store | 4 | Overnight (14 hours) | |

The prepared samples for nucleotide sequence analysis were purified by procedures described below.

The prepared sample solution was transferred from each reaction tube to another 0.5-mL tube. An additional solution was prepared in advance in a 1.5-mL tube, in such a ratio that 0.5 μL of 3 M sodium acetate aqueous solution and 12.5 μL of 95% ethanol are to be mixed with 5 μL of the sample solution. The sample solution collected in advance was added into this 1.5-mL tube. The solution was uniformly mixed and then left standing under ice cooling for 10 minutes to ethanol-precipitate (deposit) the DNA fragments contained therein. The deposited DNA fragments were sedimented by centrifugation (14,000 rpm) for 20 minutes, and the supernatant was removed therefrom. Subsequently, the deposited DNA fragments were rinsed by the addition of 125 μL of 70% ethanol. The deposited DNA fragments were sedimented again by centrifugation (14,000 rpm) for 5 minutes, and the supernatant was removed by aspiration. The remaining pellets of deposited DNA fragments were dried up.

The purified DNA fragments of sample for analysis were redispersed in Template suppressor Reagent (TSR). The solution was well mixed by vortex and then was subjected to centrifugation to collect a solution therefrom. The solution was heated up at 95° C. for 2 minutes to split the DNA fragments to single-stranded DNA, and cooled on ice. The solution was subjected to vortex once again, and then was centrifugated again to collect the solution containing the extended single-stranded DNA therefrom. Then, the DNA fragments of sample for analysis (extended single-stranded DNA) was loaded to a commercially available sequencing apparatus ABI PRISM 3100 Genetic Analyzer to analyze the nucleotide sequence thereof.

The nucleotide sequence of the inserted cDNA fragment (5' RACE reaction product) was determined by combining the results of sequencing from the 5' terminus and the results of sequencing from the 3' terminus with each another.

When the determined nucleotide sequences of the 5' RACE reaction products were mutually compared among the 8 clones, two types of 5' RACE reaction products were found which differed in their N-terminal amino acid sequences encoded by the ORF portions. Based on the nucleotide sequences of these two types of 5' RACE reaction products, the following three types of upstream primers White luc1 5'-UP1, White luc1 5'-UP2 and White luc2 5'-UP1 were designed from their respective 5'-uncoding regions:

```
White luc1 5'-UP1: (39 mer)
5'-GGAGACAACTGGATCCAAAAGGAAAGGAGCTAAATCTAC-3'

White luc1 5'-UP2: (29 mer)
5'-AAAAGGAAAGGAGCTAAATCTACAGTCTA-3'

White luc2 5'UP1: (37 iner)
5'-GAGTCCAAACTGAAAGGTACTCAAAAATGGGAGTCAA-3'
```

Reacquisition of 3' RACE Reaction Product

3' Ready cDNA prepared again based on the mRNA from M. pacifica was used as a template to newly prepare 3' RACE reaction products having a nucleic acid strand extended from each upstream primer with use of the three types of upstream primers White luc1 5'-UP1, White luc1 5'-UP2, and White luc2 5'-UP1.

3' RACE reaction products were prepared by using 3' Ready cDNA, which was newly prepared based on the mRNA from M. pacifica, as a template with use of three sets of primer pairs shown in Table 25 below.

[Table 25]

TABLE 25

| Primer pair for 5' RACE reaction Template cDNA: 5' Ready cDNA | | |
|---|---|---|
| Primer pair | Upstream primer | Downstream primer (GS primer) |
| Set luc1 5'-UP1 | White Luc1 5'-UP1 | 3' Ready primer |
| Set luc1 5'-UP2 | White Luc1 5'-UP2 | 3' Ready primer |
| Set luc2 5'-UP1 | White Luc2 5'-UP1 | 3' Ready primer |

Table 26 shows the composition of the reaction solution and the conditions of PCR amplification reaction.

[Table 26]

TABLE 26

| Temperature conditions of PCR reaction: Apparatus used: Mastercycler Gradient (eppendorf) | | | |
|---|---|---|---|
| Operation cycle | Temperature ° C. | Time | |
| denature | 96 | 1 min. | |
| anneal | 60 | 10 sec. | |
| extention | 68 | 60 sec. | 40 times |
| denature | 96 | 5 sec. | |
| extention | 68 | 60 sec. | |
| store | 10 | Overnight (14 hours) | |

| Composition of PCR reaction solution DNA polymerase: Pyrobest DNA polymerase | | | |
|---|---|---|---|
| Composition | Concentration of undiluted solution | Formulated amount μL | Final concentration |
| H₂O | | 13.75 | |
| 10× Pyro Buffer | 10× | 2.5 | 1× |
| dNTP | 2 mM | 2.5 | 0.2 mM |
| Pyrobest DNA Pol | 5 U/μL | 0.25 | 0.050 U/μL |
| GS Primer | 10 μM | 1.0 | 0.4 μM |
| Upstream Primer | 10 μM | 2.5 | 1 μM |
| cDNA | 10 dil | 2.5 | 1 dil |
| Total | | 25.0 | |

After PCR reaction performed at each reaction solution amount of 25 µL, 5 µL aliquots of the reaction solutions were sampled and electrophoresed on 1% agarose gel to confirm the molecular weights of the PCR amplification products (3' RACE reaction products).

The reacquired 3' RACE reaction product was temporarily inserted into a cloning vector pCR4Blunt-TOPO. The obtained vector was introduced into Chemical competent cell TOP10 strains, and then transformed strains were selected therefrom. The introduction of the plasmid vector in which the reacquired 3' RACE reaction product was subcloned, into the host E. coli was performed by use of the Chemical competent cell according to the aforementioned procedures for the preparation of the transformed strain in which the 5' RACE reaction product was subcloned.

Nucleotide Sequence Analysis of cDNA Fragment (3' RACE Reaction Product) in Screened Clone The reacquired 3' RACE reaction product-containing portion inserted in the plasmid vector carried by each of the screened clones was used as a template to prepare nucleic acid strand extension reaction products for nucleotide sequence analysis according to procedures described below.

The solutions containing the plasmid vectors collected and purified from the screened clones were subjected to concentration adjustment so as to set their DNA concentrations at 70 to 100 ng/µL. Subsequently, the purified plasmid vector was used as a template, and only M13 RV that was selected from two types of primers M13 sense M4 and M13 RV, which are corresponding to the site from the cloning vector pCR4Blunt-TOPO, was used as sequencing primer to prepare a sample for nucleotide sequence analysis from the region containing the 3' RACE reaction product inserted in the plasmid vector, by means of a commercially available sequencing DNA sample preparation kit BigDye Terminator Cycle Sequencing Ready Reaction Kit with AmpliTaq polymerase. Table 27 shows the temperature conditions used for the DNA strand extension reaction and the composition of the reaction solution thereof.

[Table 27]

TABLE 27

Composition of reaction solution

| Component | Concentration of undiluted solution | Ratio of formulated amount µL |
|---|---|---|
| Terminator Reaction Mix | | 1.0 |
| Template DNA | 70~100 ng/µL | 3.2 |
| primer | 1 µM | 0.8 |
| DDW | | 0.8 |
| Total | | 5.0 |

TABLE 27-continued

Temperature conditions of DNA strand extension reaction:
Apparatus used: Mastercycler Gradient

| Operation for temperature cycle | Temperature °C. | Time | |
|---|---|---|---|
| denature | 96 | 1 min. | |
| denature | 96 | 10 sec. | 25 times |
| anneal | 50 | 5 sec. | Ramp. Rate 1° C./s |
| extention | 60 | 4 min. | Ramp. Rate 1° C./s |
| store | 4 | Overnight (14 hours) | |

The prepared samples for nucleotide sequence analysis were purified by procedures described below.

The prepared sample solution was transferred from each reaction tube to another 0.5-mL tube. An additional solution was prepared in advance in a 1.5-mL tube, in such a ratio that 0.5 µL of 3 M sodium acetate aqueous solution and 12.5 µL of 95% ethanol are to be mixed with 5 µL of the sample solution. The sample solution collected in advance was added into this 1.5-mL tube. The solution was uniformly mixed and then left standing under ice cooling for 10 minutes to ethanol-precipitate (deposit) the DNA fragments contained therein. The deposited DNA fragments were sedimented by centrifugation (14,000 rpm) for 20 minutes, and the supernatant was removed therefrom.

Subsequently, the deposited DNA fragments were rinsed by the addition of 125 µL of 70% ethanol. The deposited DNA fragments were sedimented again by centrifugation (14,000 rpm) for 5 minutes, and the supernatant was removed by aspiration. The remaining pellets of deposited DNA fragments were dried up.

The purified DNA fragments of sample for analysis were redispersed in Template suppressor Reagent (TSR). The solution was well mixed by vortex and then was subjected to centrifugation to collect a solution therefrom. The solution was heated up at 95° C. for 2 minutes to split the DNA fragments to single-stranded DNA, and cooled on ice. The solution was subjected to vortex once again, and then was centrifugated again to collect the solution containing the extended single-stranded DNA therefrom. Then, the DNA fragments of sample for analysis (extended single-stranded DNA) was loaded to a commercially available sequencing apparatus ABI PRISM 3100 Genetic Analyzer to analyze the nucleotide sequence thereof.

Ten colonies were selected for each transformed strain, and newly analyzed nucleotide sequences were compared among the 3' RACE reaction products of which the nucleic acid strand was extended from each upstream primer with use of the three types of upstream primers White luc1 5'-UP1, White luc1 5'-UP2 and White luc2 5'-UP1. As a result, it was revealed that the nucleotide sequence of the 3' RACE reaction product that was extended from the upstream primer White luc1 5'-UP1, which was carried in one clone White luc1 3'RACE UP1-UPM/pCR4Blunt No. 10, is that presented below.

```
Nucleotide sequence of White luc1 3'RACE No. 10
GGAGACAACG GATCCAAAAG GAAAGGAGCT AAATCTACAG TCTAGAAC        48

ATG ATG GAA ATA CAA GTT CTT TTT GCT CTC ATT TGC              84
 M   M   E   I   Q   V   L   F   A   L   I   C
```

```
                    -continued
TTT GCA TTG GTG CAG GCC AAT CCA ACT GAA AAC AAA       120
 F   A   L   V   Q   A   N   P   T   E   N   K GAT GAC ATT GAC ATT GTT GGT GTA GAA GGA AAA TTT       156
 D   D   I   D   I   V   G   V   E   G   K   F GGT ACA ACA GAC CTT GAG ACA GAC TTA TTC ACC ATC       192
 G   T   T   D   L   E   T   D   L   F   T   I GTG GAG GAT ATG AAT GTC ATC AGT AGA GAC ACC AAT       228
 V   E   D   M   N   V   I   S   R   D   T   N CTA GCC AAC AGT GAT GCT GAC CGC GGT AAA ATG CCT       264
 L   A   N   S   D   A   D   R   G   K   M   P GGT AAA AAA CTG CCA CTG GAG GTA CTC ATA GAG ATG       300
 G   K   K   L   P   L   E   V   L   I   E   M GAA GCC AAT GCT CGT AAA GCT GGC TGC ACC AGG GGA       336
 E   A   N   A   R   K   A   G   C   T   R   G TGT CTC ATC TGT CTT TCA AAG ATC AAG TGT ACA GCA       372
 C   L   I   C   L   S   K   I   K   C   T   A AAA ATG AAG GTG TAC ATT CCA GGA AGA TGT CAT GAT       408
 K   M   K   V   Y   I   P   G   R   C   H   D TAT GGC GGT GAC AAG AAA ACT GGA CAG GCA GGA ATA       444
 Y   G   G   D   K   K   T   G   Q   A   G   I GTT GGT GCC ATT GTT GAC ATT CCC GAA ATT TCT GGA       480
 V   G   A   I   V   D   I   P   E   I   S   G TTC AAG GAG TTG GGA CCC ATG GAG CAG TTT ATT GCT       516
 F   K   E   L   G   P   M   E   Q   F   I   A CAA GTT GAT CTT TGC GCT GAC TGC ACA ACT GGC TGC       552
 Q   V   D   L   C   A   D   C   T   T   G   C CTC AAA GGT CTT GCC AAT GTC AAG TGC TCC GCA CTC       588
 L   K   G   L   A   N   V   K   C   S   A   L CTG AAG AAA TGG CTT CCA GAC AGA TGT GCA AGT TTT       624
 L   K   K   W   L   P   D   R   C   A   S   F GCT GAC AAA ATC CAG AGT GAA GTA GAC AAC ATC AAG       660
 A   D   K   I   Q   S   E   V   D   N   I   K GGC TTG GCT GGA GAT CGT TGA                           681
 G   L   A   G   D   R   *

ATAAACCTGA CAGAACAGAA CAAGAGATAA CTGGATCATG ATATGCTTGA 731

CTCATGCTAA AAAAGTGGCC ATTTTTTTGT CAAACAGAAT GAAATTAAAA  781

TATTGAATTG TTTATTAATA TGAATGGAAT TCCTATAAAT ATATTCTATG  831

TAATCCAAAA AAAAAAAAA AAAAAAAAA AAAAAG                 867
```

It was also revealed that the nucleotide sequence of the 3′ RACE reaction product that was extended from the upstream primer White luc2 5′-UP1, which was carried in one clone White luc2 3′RACE UP1-UPM/pCR4Blunt No. 7, is that presented below:

```
Nucleoticle sequence of White luc2 3'RACE No. 7
GAGTCCAAAC TGAAAGGTAC TCAAAA                           26

ATG GGA GTC AAA CTT ATC TTT GCT GTT GTT TGT GTT       62
 M   G   V   K   L   I   F   A   V   V   C   V

GCC GCG GCC CAG GCT GCC ACA ATC AAT GAA AAC TTT       98
 A   A   A   Q   A   A   T   I   N   E   N   F

GAA GAC ATT GAT CTT GTA GCT ATA GGT GGC AGC TTT       134
```

```
                         -continued
    E   D   I   D   L   V   A   I   G   G   S   F GCT CTG GAT GTT GAT GCT AAC AGA GGT GGA CAT GGT          170
 A   L   D   V   D   A   N   R   G   G   H   G GGA CAT CCT GGC AAG AAG ATG CCA AAA GAA GTA CCT          206
 G   H   P   G   K   K   M   P   K   E   V   L GTT GAA ATG GAA GCT AAT GCT AAA AGG GCT GGG TGC          242
 V   E   M   E   A   N   A   K   R   A   G   C CAC AGA GGA TGT CTG ATT TGT CTT TCC CAC ATC AAG          278
 H   R   G   C   L   I   C   L   S   H   I   K TGC ACC AAG AAA ATG AAG AAG TTT ATC CCA GGA AGA          314
 C   T   K   K   M   K   K   F   I   P   G   R TGC CAC AGT TAT GAA GGA GAC AAG GAT TCT GCA CAG          350
 C   H   S   Y   E   G   D   K   D   S   A   Q GGA GGC ATT GGA GAA GAA ATT GTT GAC ATG CCT GAA          386
 G   G   I   G   E   E   I   V   D   M   P   E ATT CCC GGA TTC AAA GAC AAG GAA CCA ATG GAC CAA          422
 I   P   G   F   K   D   K   E   P   M   D   Q TTC ATC GCT CAA GTT GAT CTC TGC GTA GAT TGC ACA          458
 F   I   A   Q   V   D   L   C   V   D   C   T ACT GGA TGC CTC AAG GGT CTT GCC AAT GTC CAT TGC          494
 T   G   C   L   K   G   L   A   N   V   H   C TCT GAT CTC CTG AAG AAA TGG CTT CCT TCA AGA TGC          530
 S   D   L   L   K   W   L   P   S   R   C AAG ACA TTT GCT TCC AAA ATT CAA TCT CAA GTG GAT          566
 K   T   F   A   S   K   I   Q   S   Q   V   D ACC ATC AAG GGA TTA GCT GGA GAT CGT TGA                  596
 T   I   K   G   L   A   G   D   R   *

GGGATAAAAA AATGGATAAT TGATGATGA TACTTTAGCC CAATGATGTT    646

AAAAATGGCC ATTTTCGTAT TAAACCATAA CTATGTAAAA ATGTAATGTA   696

TGCAAATAAA AAAAACCTTA ACGGTTTAAA AAAAAAAAAA AAAAAAAAA    746

AAAAAAA                                                  753
```

In the comparison between these two types of nucleotide sequences, the former contains ORF encoding 210 amino acid residues, while the latter contains ORF encoding 189 amino acid residues. A protein encoded by the former gene was designated as *M. pacifica* luciferase 1, while a protein encoded by the latter gene was designated as *M. pacifica* luciferase 2.

From the nucleotide sequence portion encoding this *M. pacifica* luciferase 1, the following downstream primer White luc1B LP1 was designed:

```
White luc1B LP1: (37 mer)
5'-ACTGTTGACTAGATTGGTGTCTCTACTGATGACATTC-3'
```

The White luc1B LP1 is a nucleotide sequence complementary to the following portion in ORF:

```
G AAT GTC ATC AGT AGA GAC ACC AAT CTA GTC AAC ACT
  N   V   I   S   R   D   T   N   L   V   N   S
```

In addition, two types of downstream primers White luc1 3'-LP1 and White luc1 3'-LP2 described below were designed based on the nucleotide sequence of the 3'-uncoding region in the nucleotide sequence of the 3' RACE reaction product that was extended from the upstream primer White luc1 5'-UP1. Moreover, two types of downstream primers White luc2 3'-LP1 and White luc2 3'-LP2 described below were designed based on the nucleotide sequence of the 3'-uncoding region in the nucleotide sequence of the 3' RACE reaction product that was extended from the upstream primer White luc2 5'-UP1.

```
White luc1 3'-LP1: (27 mer)
5'-GGATTACATAGAATATATTTATAGGAA-3'

White luc1 3'-LP2: (29 mer)
5'-CATGATCCAGTTATCTCTTGTTCTGTTCT-3'

White luc2 3'-LP1: (28 mer)
5'-ATTTTTACATAGTTATGGTTTAATACGA-3'

White luc2 3'-LP2: (29 mer)
5'-TAACATCATTGGGCTAAAGTATCATCATC-3'
```

Reacquisition of 5' RACE Reaction Product

The aforementioned downstream primer White luc1B LP1 was used to newly prepare 5' RACE reaction products of which a nucleic acid strand was extended from the downstream primer, based on the mRNA from *M. pacifica*.

The reacquired 5' RACE reaction product was temporarily inserted into a cloning vector pCR4Blunt-TOPO, which was then introduced into TOP10 strains. Transformed strains were selected therefrom. The nucleotide sequence of a portion corresponding to the 5'-uncoding region of the gene encoding the *M. pacifica* luciferase 1 was analyzed again by the use of the 5' RACE reaction product portion subcloned therein.

Specifically, the transformed strains screened with use of the selection marker from the cloning vector pCR4Blunt-TOPO were analyzed for the nucleotide sequences of the 5' RACE reaction products that were carried by subclone groups of White luc1 5'RACE LP1B-UPM/pCR4Blunt-TOPO, which contained the 5' RACE reaction product of which a nucleic acid strand was extended from the 3' terminus of the downstream primer White luc1B LP1 to the 5'-uncoding region of the gene encoding the *M. pacifica* luciferase 1. The nucleotide sequence of the 5'-uncoding region and the portion encoding the N-terminal portion of ORF thereof was reconfirmed thereby.

The reacquired 5' RACE reaction product-containing portion inserted in the plasmid vector, which was carried by each of the screened clones, was used as a template to prepare nucleic acid strand extension reaction products for nucleotide sequence analysis according to procedures described below.

The solutions containing the plasmid vectors collected and purified from the screened clones were subjected to concentration adjustment so as to set their DNA concentrations at 70 to 100 ng/μL. Subsequently, the purified plasmid vector was used as a template, and only M13 sense M4 that was selected from two types of primers M13 sense M4 and M13 RV, which are corresponding to the site from the cloning vector pCR4Blunt-TOPO, was used as sequencing primer to prepare a sample for nucleotide sequence analysis from the region containing the 5' RACE reaction product inserted in the plasmid vector, by means of a commercially available sequencing DNA sample preparation kit BigDye Terminator Cycle Sequencing Ready Reaction Kit with AmpliTaq polymerase.

At the same time, as for the subclone groups White luc1 3'RACE UP1-UPM/pCR4Blunt Nos. 1, 4, 5, 6, 7, 9, and 10 and White luc1 3'RACE UP2-UPM/pCR4Blunt Nos. 2, 3, 4, 5, 6, 7, 8, 9, and 10 carrying the 3' RACE reaction products, which were selected in the above screening, the nucleotide sequence of the 5'-uncoding region and the portion encoding the N-terminal portion of ORF thereof was analyzed.

Table 28 shows the sequencing primers used therefor, the temperature conditions of the DNA strand extension reaction, and the composition of the reaction solution thereof.

[Table 28]

TABLE 28

| Sequencing primer | |
|---|---|
| Template | Sequencing primer |
| White luc1 3' RACE UP1-UPM/pCR4Blunt | M13 sense M4 |
| White luc1 3' RACE UP2-UPM/pCR4Blunt | M13 sense M4 |
| White luc1 5' RACE LP1B-UPM/pCR4Blunt | M13 sense M4 |

| Composition of reaction solution | | |
|---|---|---|
| Component | Concentration of undiluted solution | Ratio of formulated amount μL |
| Terminator Reaction Mix | | 1.0 |
| Template DNA | 70~100 ng/μL | 3.2 |
| primer | 1 μM | 0.8 |
| DDW | | 0.8 |
| Total | | 5.0 |

TABLE 28-continued

Temperature conditions of DNA strand extension reaction:
Apparatus used: Mastercycler Gradient

| Operation for Temperature cycle | Temperature °C. | Time | |
|---|---|---|---|
| denature | 96 | 1 min. | |
| denature | 96 | 10 sec. | 25 times |
| anneal | 50 | 5 sec. | Ramp. Rate 1° C./s |
| extention | 60 | 4 min. | Ramp. Rate 1° C./s |
| store | 4 | Overnight (14 hours) | |

The prepared sample solution was transferred from each reaction tube to another 0.5-mL tube. An additional solution was prepared in advance in a 1.5-mL tube, in such a ratio that 0.5 μL of 3 M sodium acetate aqueous solution and 12.5 μL of 95% ethanol are to be mixed with 5 μL of the sample solution. The sample solution collected in advance was added into this 1.5-mL tube. The solution was uniformly mixed and then left standing under ice cooling for 10 minutes to ethanol-precipitate (deposit) the DNA fragments contained therein. The deposited DNA fragments were sedimented by centrifugation (14,000 rpm) for 20 minutes, and the supernatant was removed therefrom. Subsequently, the deposited DNA fragments were rinsed by the addition of 125 μL of 70% ethanol. The deposited DNA fragments were sedimented again by centrifugation (14,000 rpm) for 5 minutes, and the supernatant was removed by aspiration. The remaining pellets of deposited DNA fragments were dried up.

The purified DNA fragments of sample for analysis were redispersed in Template suppressor Reagent (TSR). The solution was well mixed by vortex and then was subjected to centrifugation to collect a solution therefrom. The solution was heated up at 95° C. for 2 minutes to split the DNA fragments to single-stranded DNA, and cooled on ice. The solution was subjected to vortex once again, and then was centrifugated again to collect the solution containing the extended single-stranded DNA therefrom. Then, the DNA fragments of sample for analysis (extended single-stranded DNA) was loaded to a commercially available sequencing apparatus ABI PRISM 3100 Genetic Analyzer to analyze the nucleotide sequence thereof.

Based on the analysis results of each subclone for the nucleotide sequences of the 5'-uncoding region and the portion encoding the N-terminal portion of ORF, upstream and downstream primers were designed as described below for the PCR amplification of the coding region from an initiation codon (ATG) located at the 5' terminus of ORF to a stop codon (TGA) at the 31 terminus. In this case, PCR amplification prepared by the use of the pair of these upstream and downstream primers was allowed to have a form capable of being incorporated into an expression vector pET101-TOPO.

For Amplification of Coding Sequence (ORF) of *M. pacifica* Luciferase 1:

```
White luc1-4 pETUP: (34 mer)
CACC ATG ATG GAA ATA AAA GTT CTT TTT GCT CTC
      M   M   E   I   K   V   L   F   A   L White luc1-9 pETUP: (34 mer)
CACC ATG ATG GAA GTA AAA GTT GTT TTT GCT CTC
      M   M   E   V   K   V   V   F   A   L
```

-continued
White luc1-10 pETUP: (34 mer)
CACC ATG ATG GAA ATA CAA GTT CTT TTT GCT CTC
     M   M   E   I   Q   V   L   F   A   L White luc1 pET-LP: (29 mer)
TCA ACG ATC TCC AGC CAA GCC CTT GAT GT This primer is a nucleotide sequence complementary to the following sequence coding for the C-terminal portion of *M. pacifica* luciferase 1:

AC ATC AAG GGC TTG GCT GGA GAT CGT TGA
       I   K   G   L   A   G   D   R   *

For Amplification of Coding Sequence (ORF) of *M. pacifica* Luciferase 2:

White luc2 pETUP: (30 mer)
CACC ATG GGA GTC AAA CTT ATC TTT GCT GT
     M   G   V   K   L   I   F   A White luc2 pETLP: (28 mer)
TCA ACG ATC TCC AGC TAA GCC CTT GAT G This primer is a nucleotide sequence complementary to the following sequence coding for C-terminal portion of *M. pacifica* luciferase 2:

C ATC AAG GGA TTA GCT GGA GAT CGT TGA
      I   K   G   L   A   G   D   R   *

(Recombinant Expression of Luciferase Protein from *M. pacifica*)

Insertion of Gene Encoding Luciferase Protein from *M. pacifica* into Plasmid pET101/D-TOPO First, the vector that was collected from the isolated clone carrying the plasmid vector White luc1 3'RACE UP1-UPM/pCR4Blunt incorporating therein the coding sequence of *M. pacifica* luciferase 1 or from the isolated clone carrying the plasmid vector White luc2 3'RACE UP1-UPM/pCR4Blunt incorporating therein the coding sequence of *M. pacifica* luciferase 1 was used as a template to prepare PCR amplification products under conditions described below by use of the aforementioned PCR forward and reverse primers. Table 29 shows the combinations of the templates and the PCR primer pairs, the temperature conditions of DNA strand extension reaction, and the composition of the reaction solution used therefor.

[Table 29]

TABLE 29

| | PCR primers | |
|---|---|---|
| Template plasmid clone | Upstream primer | Downstream primer |
| White luc1 3' RACE UP1-UPM/pCR4Blunt No. 4 | White luc1-4 pET-UP | White luc1 pET-LP |
| White luc1 3' RACE UP1-UPM/pCR4Blunt No. 9 | White luc1-9 pET-UP | White luc1 pET-LP |
| White luc1 3' RACE UP1-UPM/pCR4Blunt No. 10 | White luc1-10 pET-UP | White luc1 pET-LP |
| White luc2 3' RACE UP1-UPM/pCR4Blunt No. 6 | White luc2 pET-UP | White luc2 pET-LP |
| White luc2 3' RACE UP1-UPM/pCR4Blunt No. 7 | White luc2 pET-UP | White luc2 pET-LP |
| White luc2 3' RACE UP1-UPM/pCR4Blunt No. 8 | White luc2 pET-UP | White luc2 pET-LP |

TABLE 29-continued

Temperature conditions of PCR reaction:
Apparatus used: Mastercycler Gradient (eppendorf)

| Operation cycle | Temperature ° C. | Time | |
|---|---|---|---|
| denature | 96 | 1 min. | |
| anneal | 60: Ramp. Rate 1° C./s | 5 sec. | |
| extention | 68 | 50 sec. | 30 times |
| denature | 96 | 5 sec. | |
| extention | 68 | 50 sec. | |
| store | 10 | Overnight (14 hours) | |

Composition of PCR reaction solution
DNA polymerase: Pyrobest DNA polymerase

| Composition | Concentration of undiluted solution | Formulated amount μL | Final concentration |
|---|---|---|---|
| H$_2$O | | 16.25 | |
| 10× Pyro Buffer | 10× | 2.5 | 1× |
| dNTP | 2 mM | 2.5 | 0.2 mM |
| Pyrobest DNA Pol | 5 U/μL | 0.25 | 0.050 U/μL |
| Upstream Primer | 10 μM | 0.5 | 0.2 μM |
| Downstream Primer | 10 μM | 0.5 | 0.2 μM |
| Template plasmid | 10 ng/μL | 2.5 | 1 ng/μL |
| Total | | 25.0 | |

The prepared PCR amplification products were purified by procedures described below.

After PCR reaction performed at each reaction solution amount of 25 μL, the reaction solutions from three reactions in total were combined, and a 2 μL aliquot of the reaction solution was sampled and electrophoresed on 1.6% agarose gel to confirm PCR amplification products with the molecular weights of interest.

Subsequently, the DNA product from the reaction solution was concentrated with MinElute (produced by QIAGEN). Five volumes of buffer PB was added per volume (73 μL) of the reaction solution, and after mixing them was made by vortex, the mixture was transferred to the MinElute column. The DNA-adsorbed column was separated by centrifugation for 30 seconds, and the supernatant was removed therefrom. The DNA-adsorbed column was washed with 0.7 mL of buffer PE and separated by centrifugation (15,000 rpm) for additional 1 minute, and thereby the buffer PE was completely removed therefrom. Then, 10 μL of elution buffer EB was added to the column, and then the column was left standing at room temperature for 1 minute. Following this elution treatment, the supernatant containing DNA eluted from the column was separated by centrifugation (15,000 rpm) for 1 minute, and collected into a 1.5-mL Eppendorf tube.

After 2 μL of 10× loading dye solution was added to the collected DNA solution, 12 μL/lane of the DNA solution was electrophoresed on 1.0% TAE agarose gel. The band with the molecular weight of interest was cut out from the gel. The gel piece cut off was added into a 1.5-mL Eppendorf tube, and the DNA was isolated and collected therefrom.

The purified double-stranded DNA was inserted into a commercially available pET101-TOPO (produced by Invitrogen) to clone the gene (coding sequence portion) encoding the luciferase protein from *M. pacifica* into the vector. The constructed vector was introduced into Chemical competent cell TOP10 strains, and transformed strains were selected therefrom. The plasmid vector introduction into the host *E.*

*coli* was performed with use of the Chemical competent cell according to the procedures described above.

Screening of Clone Carrying Plasmid Vector with Luciferase Protein-Encoding Gene (Coding Sequence Portion) Insert by Colony PCR Method The presence or absence of cDNA fragment insertion in the plasmid-vectors collected from the transformed strains forming each colony was confirmed by means of the colony PCR method according to procedures described below.

In the colony PCR, a T7 primer from the plasmid pET101-TOPO was used as a forward primer, while White luc1 pET-LP or White luc2 pET-LP was used as a reverse primer. The vector DNA contained in the clone was used as a template to perform PCR amplification by using commercially available DNA synthetase KOD Dash DNA polymerase. In this case, such clones were selected that provide DNA fragments with molecular weights described below as the PCR products amplified with the primer pairs used. Table 30 shows the temperature conditions of the PCR reaction used and the composition of the reaction solution thereof.

[Table 30]

TABLE 30

Primers used for colony PCR

| Colony (upstream primer) | Forward primer | Reverse primer |
|---|---|---|
| White luc1-4/pET101/TOP10 (White luc1-4 pET-UP) | T7 primer | White luc1 pET-LP |
| White luc1-9/pET101/TOP10 (White luc1-9 pET-UP) | T7 primer | White luc1 pET-LP |
| White luc1-10/pET101/TOP10 (White luc1-10 pET-UP) | T7 primer | White luc1 pET-LP |
| White luc2-6/pET101/TOP10 (White luc2 pET-UP) | T7 primer | White luc2 pET-LP |
| White luc2-7/pET101/TOP10 (White luc2 pET-UP) | T7 primer | White luc2 pET-LP |
| White luc2-8/pET101/TOP10 (White luc2 pET-UP) | T7 primer | White luc2 pET-LP |

Temperature conditions of PCR reaction:
Apparatus used: Mastercycler Gradient (eppendorf)

| Operation cycle | Temperature ° C. | Time | |
|---|---|---|---|
| denature | 96 | 1 min. | |
| anneal | 55 | 5 sec. | |
| extention | 74 | 20 sec. | 25 times |
| denature | 96 | 5 sec. | |
| extention | 74 | 20 sec. | |
| store | 10 | Overnight (14 hours) | |

Composition of reaction solution
DNA polymerase: KOD Dash

| Component | Concentration of undiluted solution | Formulated amount μL | Final concentration |
|---|---|---|---|
| H$_2$O | | 5.8 | |
| Dash Buffer | 10× | 1.0 | 1× |
| dNTP | 2 mM | 1.0 | 0.2 mM |
| KOD Dash | 2.5 U/μL | 0.2 | 0.050 U/μL |
| T7 primer | 10 μM | 0.5 | 0.5 μM |
| pET-LP primer | 10 μM | 0.5 | 0.5 μM |
| Colony soln. | | 1.0 | |
| Total | | 10.0 | |

Colonies were randomly selected from the colonies on the Petri dish. The bacterial cells in each colony were suspended in 70 μL of water (DDW). This bacterial cell suspension was treated at 95° C. for 5 minutes. The solution containing the vector collected from the bacterial cells was utilized as a colony solution for the reaction solution.

After the completion of PCR reaction, a 3 μL aliquot was collected from 10 μL of the reaction solution containing the amplified product and electrophoresed on 2% gel to examine the presence or absence of a PCR amplification product corresponding to the cDNA fragment and a size range thereof.

The screening using the colony PCR method clearly found out the expected PCR amplification products from the following colonies among the primarily screened colonies.

White luc1-4/pET101/TOP10: Nos. 2, 3
White luc1-9/pET101/TOP10: No. 2
White luc1-10/pET101/TOP10: Nos. 3, 5
White luc2-6/pET101/TOP10: No. 1
White luc2-7/pET101/TOP10: Nos. 4, 6
White luc2-8/pET101/TOP10: Nos. 2, 5

The luciferase protein-encoding gene-containing portion inserted in the plasmid vector that was carried by each of the screened clones was used as a template to prepare nucleic acid strand extension reaction products for nucleotide sequence analysis according to procedures described below.

The solutions containing the plasmid vectors collected and purified from the screened clones were subjected to concentration adjustment so as to set their DNA concentrations at 70 to 100 ng/μL.

Subsequently, the purified plasmid vector was used as a template to prepare a sample for nucleotide sequence analysis with use of two types of primers; T7 primer and T7 terminator, which are corresponding to the site from the cloning vector pET101-TOPO, as sequencing primers by means of a commercially available sequencing DNA sample preparation kit BigDye Terminator Cycle Sequencing Ready Reaction Kit with AmpliTaq polymerase.

Table 31 shows the sequencing primers used, the temperature conditions of the DNA strand extension reaction used, and the composition of the reaction solution thereof.

[Table 31]

TABLE 31

Sequencing primer

| Colony | Forward primer | Reverse primer |
|---|---|---|
| White luc1-4/pET101/TOP10 No. 2, 3 | T7 primer | T7 terminal primer |
| White luc1-9/pET101/TOP10 No. 2 | T7 primer | T7 terminal primer |
| White luc1-10/pET101/TOP10 No. 3, 5 | T7 primer | T7 terminal primer |
| White luc2-6/pET101/TOP10 No. 1 | T7 primer | T7 terminal primer |
| White luc2-7/pET101/TOP10 No. 4, 6 | T7 primer | T7 terminal primer |
| White luc2-8/pET101/TOP10 No. 2, 5 | T7 primer | T7 terminal primer |

Composition of reaction solution

| Component | Concentration of undiluted solution | Ratio of formulated amount μL |
|---|---|---|
| Terminator Reaction Mix | | 1.0 |
| Template DNA | 250 ng/μL | 2.0 |
| primer | 1 μM | 0.8 |
| DDW | | 1.2 |
| Total | | 5.0 |

TABLE 31-continued

Temperature conditions of DNA strand extension reaction:
Apparatus used: Mastercycler Gradient

| Operation for Temperature cycle | Temperature ° C. | Time | |
|---|---|---|---|
| denature | 96 | 1 min. | |
| denature | 96 | 10 sec. | 25 times |
| anneal | 50 | 5 sec. | Ramp. Rate 1° C./s |
| extention | 60 | 4 min. | Ramp. Rate 1° C./s |
| store | 4 | Overnight (14 hours) | |

The prepared sample solution was transferred from each reaction tube to another 0.5-mL tube. An additional solution was prepared in advance in a 1.5-mL tube, in such a ratio that 0.5 µL of 3 M sodium acetate aqueous solution and 12.5 µL of 95% ethanol are to be mixed with 5 µL of the sample solution. The sample solution collected in advance was added into this 1.5-mL tube. The solution was uniformly mixed and then left standing under ice cooling for 10 minutes to ethanol-precipitate (deposit) the DNA fragments contained therein. The deposited DNA fragments were sedimented by centrifugation (14,000 rpm) for 20 minutes, and the supernatant was removed therefrom. Subsequently, the deposited DNA fragments were rinsed by the addition of 125 µL of 70% ethanol. The deposited DNA fragments were sedimented again by centrifugation (14,000 rpm) for 5 minutes, and the supernatant was removed by aspiration. The remaining pellets of deposited DNA fragments were dried up.

The purified DNA fragments of sample for analysis were redispersed in Template suppressor Reagent (TSR). The solution was well mixed by vortex and then was subjected to centrifugation to collect a solution therefrom. The solution was heated up at 95° C. for 2 minutes to split the DNA fragments to single-stranded DNA, and cooled on ice. The solution was subjected to vortex once again, and then was centrifugated again to collect the solution containing the extended single-stranded DNA therefrom. Then, the DNA fragments of sample for analysis (extended single-stranded DNA) was loaded to a commercially available sequencing apparatus ABI PRISM 3100 Genetic Analyzer to analyze the nucleotide sequence thereof.

The result of nucleotide sequence analysis demonstrated that the PCR amplification product prepared by the use of the aforementioned PCR forward and reverse primers is inserted in the cloning site of the plasmid pET101-TOPO in each of said screened clones.

Because of difference in the nucleotide sequences of the upstream primers used, the coding sequences of *M. pacifica* luciferase 1 in the PCR amplification products differ in the portions corresponding to the N-terminal regions between the sequences carried by White luc1-4/pET101/TOP10 and White luc1-9/pET101/TOP10 and the sequence carried by White luc1-10/pET101/TOP10. Specifically, the sequences carried by White luc1-4/pET101/TOP10 and White luc1-9/pET101/TOP10 differ from the sequence carried by White luc1-10/pET101/TOP10 and are coding sequences of variant proteins having amino acid replacement in the portions corresponding to the N-terminal region.

(Luminescent Properties of Recombinantly Expressed Luciferase Protein from *M. pacifica*)

For the two types of screened clones White luc1-10/pET101/TOP10 and White luc2-7/pET101/TOP10, the expression of the inserted genes under control of the promoter from the vector pET101-TOPO was induced by using IPTG. At the point in time when 4 hours passed, the cultured bacterial cells were collected. After bacterial cell homogenization, SDS-PAGE analysis was conducted on proteins respectively contained in the soluble fractions (cytoplasm components) and the insoluble fractions (membrane components) separated by centrifugation (15,000 rpm; 18,800×g). As a result, new bands corresponding to the luciferase proteins of interest were found in the soluble fractions (cytoplasm components) of the transformed *E. coli*.

When a luminescent substrate coelenterazine was added to the soluble fractions (cytoplasm components) of the transformed *E. coli* at pH 7.5 in the presence of 100 mM $CaCl_2$, blue luminescence with the maximum wavelength λmax=480 nm was observed therein. Specifically, it was confirmed that the recombinant luciferase proteins are produced by expression from each of the genes encoding *M. pacifica* luciferase 1 and *M. pacifica* luciferase 2 in the host *E. coli*, respectively. This also suggested that divalent metal cations such as Ca are required for exerting their luminescent activities.

(pH Dependency of Luminescent Properties of Recombinantly Expressed Luciferase Protein from *M. pacifica*)

For the two types of screened clones White luc1-10/pET101/TOP10 and White luc2-7/pET101/TOP10, the soluble fractions (cytoplasm components) of the transformed *E. coli* comprising the recombinantly expressed luciferase proteins were used to evaluate the pH dependency of the luminescent properties of each recombinantly expressed luciferase protein.

The pHs of the solutions containing the recombinantly expressed luciferase proteins were changed to various values in the presence of 50 mM $MgCl_2$ to allow a luminescent substrate coelenterazine to emit blue luminescence according to the enzyme activities.

FIG. 2 shows a result of plotting, against pH values adjusted with a variety of buffer solutions described below, blue luminescences (luminescence intensity measured at a wavelength of 480 nm) emitted from a luminescent substrate coelenterazine by the actions of the recombinantly expressed luciferase proteins at the pHs adjusted with a variety of buffer solutions, as for recombinantly expressed luciferase proteins from *M. pacifica* according to the present invention. The result demonstrated that the recombinantly expressed *M. pacifica* luciferase 1 and *M. pacifica* luciferase 2 exhibit the desired level of luminescent properties at least in the pH range from 6.5 to 9.0.

Buffer Solution Used for pH Adjustment:

| | |
|---|---|
| pH 5.0 | Acetate |
| pH 5.5 | Acetate |
| pH 6.0 | Phosphate |
| pH 7.0 | HEPES |
| pH 8.0 | Tris-HCl |
| pH 8.5 | Tris-HCl |
| pH 8.9 | Tris-HCl |
| pH 10.0 | Carbonate |

(Necessity of Metal Cation for Exerting Luminescent Properties of Recombinantly Expressed Luciferase Protein from *M. pacifica*)

For the two types of screened clones White luc1-10/pET101/TOP10 and White luc2-7/pET101/TOP10, the soluble fractions (cytoplasm components) of the transformed *E. Coli* comprising the aforementioned recombinantly expressed luciferase proteins were used to evaluate the necessity of metal cations for exerting the luminescent properties of each recombinantly expressed luciferase protein.

Figure 3:
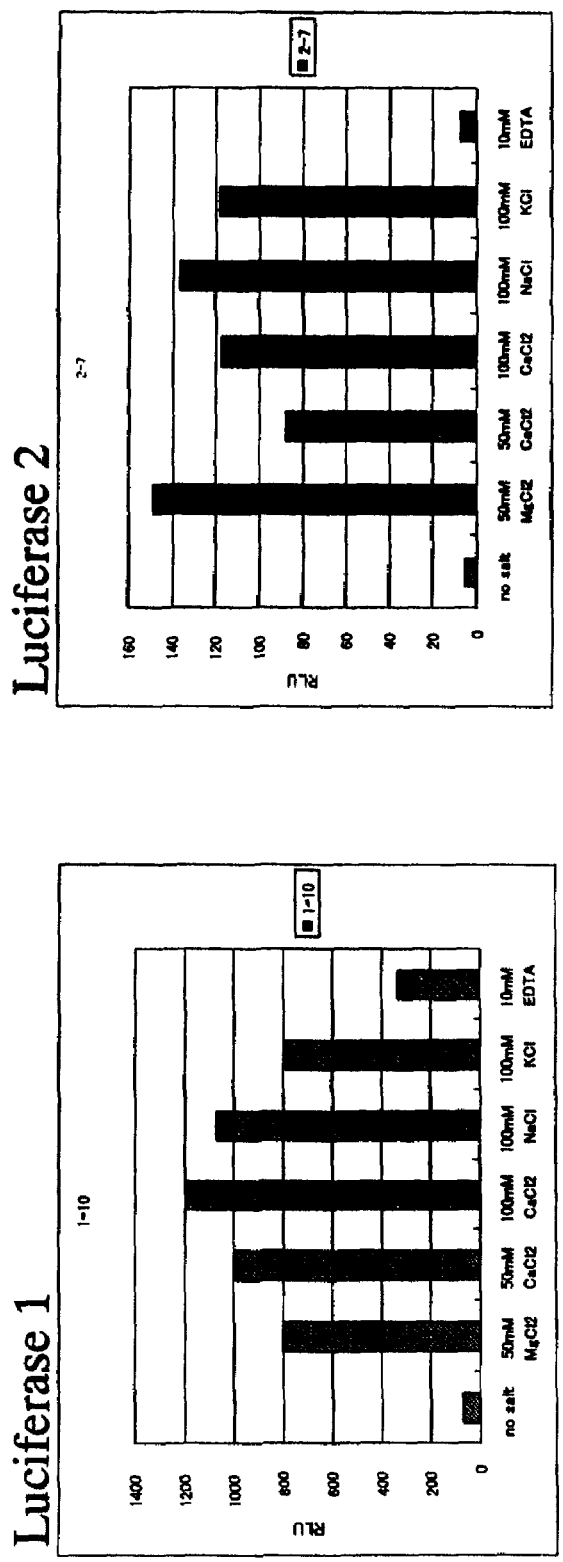
FIG. 3 shows the necessity of a metal cation for exerting the luminescent activities of recombinantly expressed proteins of *Metridia pacifica* luciferase 1 and *Metridia pacifica* luciferase 2, which are both recombinantly expressed from the genes encoding luciferase proteins from *Metridia pacifica* according to the present invention, and shows a result of comparing blue luminescences (luminescence intensity measured at a wavelength of 480 nm) emitted from a luminescent substrate coelenterazine by the actions of the recombinantly expressed luciferase proteins at pH 7.5 in the presence of alkali metal cations ($K^+$ and $Na^+$) and alkaline earth metal cations ($Ca^{2+}$ and $Mg^{2+}$).

FIG. 3 shows a result of comparing blue luminescences (luminescence intensity measured at a wavelength of 480 nm)

emitted from a luminescent substrate coelenterazine by the actions of the recombinantly expressed luciferase proteins at pH 7.5 in the presence of alkali metal cations ($K^+$ and $Na^+$) and alkaline earth metal cations ($Ca^{2+}$ and $Mg^{2+}$), as for the recombinantly expressed luciferase proteins from *M. pacifica* according to the present invention. The result demonstrated that the recombinantly expressed *M. pacifica* luciferase 1 and *M. pacifica* luciferase 2 require the presence of at least approximately 50 mM alkali metal cations ($K^+$ and $Na^+$) and alkaline earth metal cations ($Ca^{2+}$ and $Mg^{2+}$) for exerting the desired level of luminescent properties.

(Recombinant Expression of Luciferase Protein from *M. pacifica* in Human Cell)

Insertion of Gene Encoding *M. pacifica* Luciferase 1 or *M. pacifica* Luciferase 2 into Plasmid pcDNA3.2/V5-GW/D-TOPO Purified double-stranded DNA prepared by a PCR method was inserted into the cloning site of a commercially available plasmid pcDNA3.2/V5-GW/D-TOPO (produced by Invitrogen) to prepare expression vectors for the expression of the luciferase proteins from *M. pacifica* in human cells, according to the preparation procedures of the expression vectors White luc1-10/pET101 and White luc2-7/pET101 for the luciferase proteins from *M. pacifica*, which were utilized in the recombinant expression in *E. Coli* described above.

The double-stranded DNA fragments inserted in the expression vectors for expression in human cells have the same nucleotide sequence as those of the coding genes inserted in the expression vectors White luc1-10/pET101 and White luc2-7/pET101 and do not undergo the conversion of a codon to be best fit to codon selection in humans. In brief, the double-stranded DNA fragments are the same as the double-stranded DNA fragments inserted in the expression vectors White luc1-10/pET101 and White luc2-7/pET101. The prepared expression vectors White luc1-10/pcDNA3.2 and White luc2-7/pcDNA3.2 were temporarily introduced into Chemical competent cell TOP10 strains. Transformed strains were selected therefrom. The plasmid vector introduction into the host *E. coli* was performed by use of the Chemical competent cell according to the procedures described above.

Clones in which a cDNA fragment having the same nucleotide sequence as those of the coding genes inserted in the expression vectors White luc1-10/pET101 or White luc2-7/pET101 was inserted were selected by screening using a colony PCR method. Moreover, nucleotide sequence analysis was actually conducted to confirm the nucleotide sequences of the inserted portions.

The plasmids prepared by the culture of the selected clone strains were collected and purified by the use of a commercially available plasmid purification kit QIAGEN Plasmid Maxi Kit (produced by QIAGEN).

Introduction of Expression Vector for Expression of Luciferase Protein from *M. pacifica* in Human Cell into HeLa Cell The purified expression vectors for the expression of the luciferase proteins from *M. pacifica* in human cells were introduced into HeLa cells by the use of PolyFect Transfection reagent (produced by QIAGEN). The host HeLa cells used were cultured to 70% confluence on a 100-mm dish by using a serum-supplemented medium (DMEM+10% FBS+100 µg/ml Kanamycin). 50.0 µL of PolyFect Transfection Reagent was added to 6.0 µL of the expression vector/plasmid solution (DNA content: 1 µg/µL), and then this mixture solution was stirred for 10 seconds. After that, the solution was incubated at room temperature for 10 minutes for complex formation to use in transfection treatment. After the transfection treatment, the HeLa cells were and incubated for 24 to 48 hours under such condition being kept at 37° C. under 5% $CO_2$. During this step, the recovery of cell damage resulting from the treatment and the expression of the introduced genes in the cultured cells were performed.

The recombinant expression of the luciferase proteins from *M. pacifica* was induced in the HeLa cells into which the expression vector was introduced. As a result, the luciferase proteins expressed in the cultured cells were observed to be secreted to the outside of the cells and accumulated as secreted luciferase proteins in the medium. That is to said, translation into recombinant preprotein forms having the full-length amino acid sequence was also performed in the HeLa cells from human according to the genes encoding the luciferase proteins from *M. pacifica*. This clearly shows that the preproteins were then secreted as mature proteins to the outside of the cells by the help of the N-terminal signal peptide portions.

FIG. 4 shows increases in the luminescent activity of mature *M. pacifica* luciferase 1 or *M. pacifica* luciferase 2 secreted to a medium by procedures wherein a HeLa cell, which has undergone recovery treatment for cell damage after the introduction of an expression vector White luc1-10/pcDNA3.2 or White luc2-7/pcDNA3.2 thereinto, is cultured in the medium, and recombinant expression is induced. The luminescent activity of the luciferase protein in the medium was compared with the luminescent activity of the luciferase protein remaining the cultured cell at the points in time when 24 hours and 48 hours passed in the recombinant expression-induced state during culture. The luminescent activity of the luciferase protein in the medium was confirmed to be significantly increased with the passage of culture time.

Thus, it was demonstrated that the genes encoding luciferase proteins from *M. pacifica* are sufficiently capable of being expressed in host human cells in in vitro culture systems using a variety of cell lines from human even without converting a codon to be fit to codon selection in human cells and can be utilized as genes encoding reporter proteins secreted to the outside of the cells after expression.

INDUSTRIAL APPLICABILITY

In in vitro culture systems using mammal cells, genes encoding two types of luciferase proteins from *M. pacifica* according to the present invention are both capable of being expressed in the host cells. After expression from the genes, recombinantly expressed luciferase proteins can be utilized as reporter proteins secreted to the outside of the cells.

The invention claimed is:

1. An isolated gene encoding a luciferase from *M. pacifica* comprising a nucleotide sequence encoding the full-length amino acid sequence of SEQ ID NO: 1.

2. The isolated gene encoding a luciferase protein from *M. pacifica* as claimed in claim 1, wherein the nucleotide sequence encoding the full-length amino acid sequence of SEQ ID NO: 1 is the nucleotide sequence of SEQ. ID NO: 2.

3. The isolated gene encoding a luciferase protein from *M. pacifica* as claimed in claim 1, wherein the nucleotide sequence encoding the full-length amino acid sequence of SEQ ID NO: 1 is the nucleotide sequence of SEQ ID NO:5.

4. A method for using DNA having a nucleotide sequence of SEQ ID NO: 2 as a nucleotide sequence encoding a peptide chain having an amino acid sequence of SEQ ID NO: 1, wherein the use of DNA is aimed at allowing a mammal cell in an in vitro culture system thereof to recombinantly express therein a luciferase protein whose full-length amino acid sequence is the amino acid sequence of SEQ ID NO: 1 in order to utilize the luciferase protein as a reporter protein which is produced in a secreted luciferase form to be secreted to the outside of the mammal cell, wherein the method comprises steps of
introducing the DNA into the mammal cell to form a transformed mammal cell; and
culturing the transformed mammal cell in the in vitro culture system to recombinantly express therein the luciferase protein whose full-length amino acid sequence is the amino acid sequence of SEQ ID NO: 1.

5. The method according to claim 4, wherein the mammal cell is a cell line from human that is culturable in vitro.

6. An isolated gene encoding a variant of a luciferase from *M. pacifica*, comprising a nucleotide sequence encoding the full-length amino acid sequence of SEQ ID NO: 7.

7. The isolated gene encoding a variant of a luciferase protein from *M. pacifica* as claimed in claim 6, wherein the nucleotide sequence encoding the full-length amino acid sequence of SEQ ID NO: 7 is the nucleotide sequence of SEQ ID NO: 9.

8. A method for using DNA having a nucleotide sequence of SEQ ID NO: 9 as a nucleotide sequence encoding a peptide chain having an amino acid sequence of SEQ ID NO: 7, wherein the use of DNA is aimed at allowing a mammal cell in an in vitro culture system thereof to recombinantly express therein a luciferase protein whose full-length amino acid sequence is the amino acid sequence of SEQ ID NO: 7 in order to utilize the luciferase protein as a reporter protein which is produced in a secreted luciferase form to be secreted to the outside of the mammal cell, wherein the method comprises steps of:
introducing the DNA into the mammal cell to form a transformed mammal cell; and culturing the transformed mammal cell in the in vitro culture system to recombinantly express therein the luciferase protein whose full-length amino acid sequence is the amino acid sequence of SEQ ID NO: 7.

9. The method according to claim 8, wherein the mammal cell is a cell line from human that is culturable in vitro.

10. An isolated gene encoding a variant of a luciferase from *M. pacifica*, comprising a nucleotide sequence encoding the full-length amino acid sequence of SEQ ID NO: 8.

11. The isolated gene encoding a variant of a luciferase protein from *M. pacifica* as claimed in claim 10, wherein the nucleotide sequence encoding the full-length amino acid sequence of SEQ ID NO: 8 is the nucleotide sequence of SEQ ID NO: 10.

12. A method for using DNA having a nucleotide sequence of SEQ ID NO: 10 as a nucleotide sequence encoding a peptide chain having an amino acid sequence of SEQ ID NO: 8, wherein the use of DNA is aimed at allowing a mammal cell in an in vitro culture system thereof to recombinantly express therein a luciferase protein whose full-length amino acid sequence is the amino acid sequence of SEQ ID NO: 8 in order to utilize the luciferase protein as a reporter protein which is produced in a secreted luciferase form to be secreted to the outside of the mammal cell, wherein the method comprises steps of:
introducing the DNA into the mammal cell to form a transformed mammal cell; and
culturing the transformed mammal cell in the in vitro culture system to recombinantly express therein the luciferase protein whose full-length amino acid sequence is the amino acid sequence of SEQ ID NO: 8.

13. The method according to claim 9, wherein the mammal cell is a cell line from human that is culturable in vitro.

\* \* \* \* \*

UNITED STATES PATENT AND TRADEMARK OFFICE
CERTIFICATE OF CORRECTION

PATENT NO. : 7,871,803 B2
APPLICATION NO. : 11/721032
DATED : January 18, 2011
INVENTOR(S) : Hiromi Takenaka It is certified that error appears in the above-identified patent and that said Letters Patent is hereby corrected as shown below:

In the Specifications
Column 16, Line 29: delete "Metridimidae," and insert -- Metridinidae, --
Column 16, Line 44: delete "Metridimidae," and insert -- Metridinidae, --
Column 16, Line 51: delete "Metridimidae," and insert -- Metridinidae, --
Column 21, Line 28: delete "Metridimidae," and insert -- Metridinidae, --
Column 22, Line 37: delete "grachlorostris" and insert -- gracilirostris --
Column 23, Line 27: delete "Metridimidae," and insert -- Metridinidae, --
Column 23, Line 44: delete "Metridimidae," and insert -- Metridinidae, --
Column 23, Line 52: delete "Metridimidae," and insert -- Metridinidae, --
Column 27, Line 59: delete "3" and insert -- 3' --
Column 42, Line 9: delete "iner)" and insert -- mer) --
Column 44, Line 30: delete "Subsequently, the deposited ......................were dried up." and insert the same on Col. 44, Line 29, after "therefrom" as the continuation of the paragraph.
Column 50, Line 52: delete "31" and insert -- 3' --
In the Claims
Column 83, Line 52: In Claim 2, delete "SEQ." and insert -- SEQ --

Signed and Sealed this
Thirtieth Day of July, 2013

Teresa Stanek Rea
*Acting Director of the United States Patent and Trademark Office*

SEQUENCE LISTING

<160> NUMBER OF SEQ ID NOS: 31

<210> SEQ ID NO 1
<211> LENGTH: 210

<212> TYPE: PRT
<213> ORGANISM: Metridia pacifica

<400> SEQUENCE: 1

```
Met Met Glu Ile Gln Val Leu Phe Ala Leu Ile Cys
1               5                   10

Phe Ala Leu Val Gln Ala Asn Pro Thr Glu Asn Lys
            15                  20

Asp Asp Ile Asp Ile Val Gly Val Glu Gly Lys Phe
        25                  30                  35

Gly Thr Thr Asp Leu Glu Thr Asp Leu Phe Thr Ile
            40                  45

Val Glu Asp Met Asn Val Ile Ser Arg Asp Thr Asn
    50                  55                      60

Leu Ala Asn Ser Asp Ala Asp Arg Gly Lys Met Pro
                65                  70

Gly Lys Lys Leu Pro Leu Glu Val Leu Ile Glu Met
        75                  80

Glu Ala Asn Ala Arg Lys Ala Gly Cys Thr Arg Gly
85                  90                  95

Cys Leu Ile Cys Leu Ser Lys Ile Lys Cys Thr Ala
            100                 105

Lys Met Lys Val Tyr Ile Pro Gly Arg Cys His Asp
        110                 115                 120

Tyr Gly Gly Asp Lys Lys Thr Gly Gln Ala Gly Ile
            125                 130

Val Gly Ala Ile Val Asp Ile Pro Glu Ile Ser Gly
        135                 140

Phe Lys Glu Leu Gly Pro Met Glu Gln Phe Ile Ala
145                 150                 155

Gln Val Asp Leu Cys Ala Asp Cys Thr Thr Gly Cys
            160                 165

Leu Lys Gly Leu Ala Asn Val Lys Cys Ser Ala Leu
        170                 175                 180

Leu Lys Lys Trp Leu Pro Asp Arg Cys Ala Ser Phe
            185                 190

Ala Asp Lys Ile Gln Ser Glu Val Asp Asn Ile Lys
        195                 200

Gly Leu Ala Gly Asp Arg
205                 210
```

<210> SEQ ID NO 2
<211> LENGTH: 633
<212> TYPE: DNA
<213> ORGANISM: Metridia pacifica

<400> SEQUENCE: 2

```
atg atg gaa ata caa gtt ctt ttt gct ctc att tgc           36
Met Met Glu Ile Gln Val Leu Phe Ala Leu Ile Cys
1               5                   10 ttt gca ttg gtg cag gcc aat cca act gaa aac aaa           72
Phe Ala Leu Val Gln Ala Asn Pro Thr Glu Asn Lys
            15                  20 gat gac att gac att gtt ggt gta gaa gga aaa ttt          108
Asp Asp Ile Asp Ile Val Gly Val Glu Gly Lys Phe
        25                  30                  35
```

| | | | | | | | | | | |
|---|---|---|---|---|---|---|---|---|---|---|
| ggt | aca | aca | gac | ctt | gag | aca | gac | tta | ttc | acc atc |
| Gly | Thr | Thr | Asp | Leu | Glu | Thr | Asp | Leu | Phe | Thr Ile |
| | | | 40 | | | | | 45 | | |

```
ggt aca aca gac ctt gag aca gac tta ttc acc atc      144
Gly Thr Thr Asp Leu Glu Thr Asp Leu Phe Thr Ile
            40                  45 gtg gag gat atg aat gtc atc agt aga gac acc aat      180
Val Glu Asp Met Asn Val Ile Ser Arg Asp Thr Asn
 50                  55                  60 cta gcc aac agt gat gct gac cgc ggt aaa atg cct      216
Leu Ala Asn Ser Asp Ala Asp Arg Gly Lys Met Pro
                65                  70 ggt aaa aaa ctg cca ctg gag gta ctc ata gag atg      252
Gly Lys Lys Leu Pro Leu Glu Val Leu Ile Glu Met
         75                  80 gaa gcc aat gct cgt aaa gct ggc tgc acc agg gga      288
Glu Ala Asn Ala Arg Lys Ala Gly Cys Thr Arg Gly
 85                  90                  95 tgt ctc atc tgt ctt tca aag atc aag tgt aca gca      324
Cys Leu Ile Cys Leu Ser Lys Ile Lys Cys Thr Ala
                100                 105 aaa atg aag gtg tac att cca gga aga tgt cat gat      360
Lys Met Lys Val Tyr Ile Pro Gly Arg Cys His Asp
        110                 115                 120 tat ggc ggt gac aag aaa act gga cag gca gga ata      396
Tyr Gly Gly Asp Lys Lys Thr Gly Gln Ala Gly Ile
                125                 130 gtt ggt gcc att gtt gac att ccc gaa att tct gga      432
Val Gly Ala Ile Val Asp Ile Pro Glu Ile Ser Gly
        135                 140 ttc aag gag ttg gga ccc atg gag cag ttt att gct      468
Phe Lys Glu Leu Gly Pro Met Glu Gln Phe Ile Ala
145                 150                 155 caa gtt gat ctt tgc gct gac tgc aca act ggc tgc      504
Gln Val Asp Leu Cys Ala Asp Cys Thr Thr Gly Cys
        160                 165 ctc aaa ggt ctt gcc aat gtc aag tgc tcc gca ctc      540
Leu Lys Gly Leu Ala Asn Val Lys Cys Ser Ala Leu
        170                 175                 180 ctg aag aaa tgg ctt cca gac aga tgt gca agt ttt      576
Leu Lys Lys Trp Leu Pro Asp Arg Cys Ala Ser Phe
                185                 190 gct gac aaa atc cag agt gaa gta gac aac atc aag      612
Ala Asp Lys Ile Gln Ser Glu Val Asp Asn Ile Lys
        195                 200 ggc ttg gct gga gat cgt tga                          633
Gly Leu Ala Gly Asp Arg  *
205                 210

<210> SEQ ID NO 3
<211> LENGTH: 189
<212> TYPE: PRT
<213> ORGANISM: Metridia pacifica

<400> SEQUENCE: 3

Met Gly Val Lys Leu Ile Phe Ala Val Val Cys Val
 1               5                   10

Ala Ala Ala Gln Ala Ala Thr Ile Asn Glu Asn Phe
            15                  20

Glu Asp Ile Asp Leu Val Ala Ile Gly Gly Ser Phe
25                  30                  35

Ala Leu Asp Val Asp Ala Asn Arg Gly Gly His Gly
            40                  45
```

```
Gly His Pro Gly Lys Lys Met Pro Lys Glu Val Leu
        50                  55                  60

Val Glu Met Glu Ala Asn Ala Lys Arg Ala Gly Cys
                65                  70

His Arg Gly Cys Leu Ile Cys Leu Ser His Ile Lys
            75                  80

Cys Thr Lys Lys Met Lys Lys Phe Ile Pro Gly Arg
 85                  90                  95

Cys His Ser Tyr Glu Gly Asp Lys Asp Ser Ala Gln
                100                 105

Gly Gly Ile Gly Glu Glu Ile Val Asp Met Pro Glu
            110                 115                 120

Ile Pro Gly Phe Lys Asp Lys Glu Pro Met Asp Gln
                125                 130

Phe Ile Ala Gln Val Asp Leu Cys Val Asp Cys Thr
            135                 140

Thr Gly Cys Leu Lys Gly Leu Ala Asn Val His Cys
145                 150                 155

Ser Asp Leu Leu Lys Lys Trp Leu Pro Ser Arg Cys
                160                 165

Lys Thr Phe Ala Ser Lys Ile Gln Ser Gln Val Asp
        170                 175                 180

Thr Ile Lys Gly Leu Ala Gly Asp Arg
                185

<210> SEQ ID NO 4
<211> LENGTH: 570
<212> TYPE: DNA
<213> ORGANISM: Metridia pacifica

<400> SEQUENCE: 4 atg gga gtc aaa ctt atc ttt gct gtt gtt tgt gtt                36
Met Gly Val Lys Leu Ile Phe Ala Val Val Cys Val
  1               5                  10 gcc gcg gcc cag gct gcc aca atc aat gaa aac ttt                72
Ala Ala Ala Gln Ala Ala Thr Ile Asn Glu Asn Phe
            15                  20 gaa gac att gat ctt gta gct ata ggt ggc agc ttt               108
Glu Asp Ile Asp Leu Val Ala Ile Gly Gly Ser Phe
 25                  30                  35 gct ctg gat gtt gat gct aac aga ggt gga cat ggt               144
Ala Leu Asp Val Asp Ala Asn Arg Gly Gly His Gly
            40                  45 gga cat cct ggc aag aag atg cca aaa gaa gta cct               180
Gly His Pro Gly Lys Lys Met Pro Lys Glu Val Pro
        50                  55                  60 gtt gaa atg gaa gct aat gct aaa agg gct ggg tgc               216
Val Glu Met Glu Ala Asn Ala Lys Arg Ala Gly Cys
                65                  70 cac aga gga tgt ctg att tgt ctt tcc cac atc aag               252
His Arg Gly Cys Leu Ile Cys Leu Ser His Ile Lys
        75                  80 tgc acc aag aaa atg aag aag ttt atc cca gga aga               288
Cys Thr Lys Lys Met Lys Lys Phe Ile Pro Gly Arg
 85                  90                  95 tgc cac agt tat gaa gga gac aag gat tct gca cag               324
Cys His Ser Tyr Glu Gly Asp Lys Asp Ser Ala Gln
```

```
                    100                 105
gga ggc att gga gaa gaa att gtt gac atg cct gaa           360
Gly Gly Ile Gly Glu Glu Ile Val Asp Met Pro Glu
        110                 115                 120 att ccc gga ttc aaa gac aag gaa cca atg gac caa           396
Ile Pro Gly Phe Lys Asp Lys Glu Pro Met Asp Gln
                125                 130 ttc atc gct caa gtt gat ctc tgc gta gat tgc aca           432
Phe Ile Ala Gln Val Asp Leu Cys Val Asp Cys Thr
        135                 140 act gga tgc ctc aag ggt ctt gcc aat gtc cat tgc           468
Thr Gly Cys Leu Lys Gly Leu Ala Asn Val His Cys
145                 150                 155 tct gat ctc ctg aag aaa tgg ctt cct tca aga tgc           504
Ser Asp Leu Leu Lys Lys Trp Leu Pro Ser Arg Cys
                160                 165 aag aca ttt gct tcc aaa att caa tct caa gtg gat           540
Lys Thr Phe Ala Ser Lys Ile Gln Ser Gln Val Asp
        170                 175                 180 acc atc aag gga tta gct gga gat cgt tga                   570
Thr Ile Lys Gly Leu Ala Gly Asp Arg  *
                185

<210> SEQ ID NO 5
<211> LENGTH: 867
<212> TYPE: DNA
<213> ORGANISM: Metridia pacifica

<400> SEQUENCE: 5
ggagacaacg gatccaaaag gaaaggagct aaatctacag tctagaac     48 atg atg gaa ata caa gtt ctt ttt gct ctc att tgc           84
Met Met Glu Ile Gln Val Leu Phe Ala Leu Ile Cys
  1               5                  10 ttt gca ttg gtg cag gcc aat cca act gaa aac aaa          120
Phe Ala Leu Val Gln Ala Asn Pro Thr Glu Asn Lys
         15                 20 gat gac att gac att gtt ggt gta gaa gga aaa ttt          156
Asp Asp Ile Asp Ile Val Gly Val Glu Gly Lys Phe
 25              30                  35 ggt aca aca gac ctt gag aca gac tta ttc acc atc          192
Gly Thr Thr Asp Leu Glu Thr Asp Leu Phe Thr Ile
             40                  45 gtg gag gat atg aat gtc atc agt aga gac acc aat          228
Val Glu Asp Met Asn Val Ile Ser Arg Asp Thr Asn
 50                  55                  60 cta gcc aac agt gat gct gac cgc ggt aaa atg cct          264
Leu Ala Asn Ser Asp Ala Asp Arg Gly Lys Met Pro
                 65                  70 ggt aaa aaa ctg cca ctg gag gta ctc ata gag atg          300
Gly Lys Lys Leu Pro Leu Glu Val Leu Ile Glu Met
         75                  80 gaa gcc aat gct cgt aaa gct ggc tgc acc agg gga          336
Glu Ala Asn Ala Arg Lys Ala Gly Cys Thr Arg Gly
 85                  90                  95 tgt ctc atc tgt ctt tca aag atc aag tgt aca gca          372
Cys Leu Ile Cys Leu Ser Lys Ile Lys Cys Thr Ala
                100                 105 aaa atg aag gtg tac att cca gga aga tgt cat gat          408
Lys Met Lys Val Tyr Ile Pro Gly Arg Cys His Asp
        110                 115                 120
```

```
tat ggc ggt gac aag aaa act gga cag gca gga ata                444
Tyr Gly Gly Asp Lys Lys Thr Gly Gln Ala Gly Ile
                125                 130 gtt ggt gcc att gtt gac att ccc gaa att tct gga                480
Val Gly Ala Ile Val Asp Ile Pro Glu Ile Ser Gly
            135                 140 ttc aag gag ttg gga ccc atg gag cag ttt att gct                516
Phe Lys Glu Leu Gly Pro Met Glu Gln Phe Ile Ala
145                 150                 155 caa gtt gat ctt tgc gct gac tgc aca act ggc tgc                552
Gln Val Asp Leu Cys Ala Asp Cys Thr Thr Gly Cys
                160                 165 ctc aaa ggt ctt gcc aat gtc aag tgc tcc gca ctc                588
Leu Lys Gly Leu Ala Asn Val Lys Cys Ser Ala Leu
        170                 175                 180 ctg aag aaa tgg ctt cca gac aga tgt gca agt ttt                624
Leu Lys Lys Trp Leu Pro Asp Arg Cys Ala Ser Phe
                185                 190 gct gac aaa atc cag agt gaa gta gac aac atc aag                660
Ala Asp Lys Ile Gln Ser Glu Val Asp Asn Ile Lys
                195                 200 ggc ttg gct gga gat cgt tga                                     681
Gly Leu Ala Gly Asp Arg *
205                 210 ataaacctga cagaacagaa caagagataa ctggatcatg atatgcttga          731
ctcatgctaa aaaagtggcc attttttttgt caaacagaat gaaattaaaa          781
tattgaattg tttattaata tgaatggaat tcctataaat atattctatg          831
taatccaaaa aaaaaaaaaa aaaaaaaaaa aaaaag                         867

<210> SEQ ID NO 6
<211> LENGTH: 753
<212> TYPE: DNA
<213> ORGANISM: Metridia pacifica

<400> SEQUENCE: 6
gagtccaaac tgaaaggtac tcaaaa                                    26 atg gga gtc aaa ctt atc ttt gct gtt gtt tgt gtt                 62
Met Gly Val Lys Leu Ile Phe Ala Val Val Cys Val
1                   5                   10 gcc gcg gcc cag gct gcc aca atc aat gaa aac ttt                 98
Ala Ala Ala Gln Ala Ala Thr Ile Asn Glu Asn Phe
            15                  20 gaa gac att gat ctt gta gct ata ggt ggc agc ttt                 134
Glu Asp Ile Asp Leu Val Ala Ile Gly Gly Ser Phe
25                  30                  35 gct ctg gat gtt gat gct aac aga ggt gga cat ggt                 170
Ala Leu Asp Val Asp Ala Asn Arg Gly Gly His Gly
            40                  45 gga cat cct ggc aag aag atg cca aaa gaa gta cct                 206
Gly His Pro Gly Lys Lys Met Pro Lys Glu Val Leu
        50                  55                  60 gtt gaa atg gaa gct aat gct aaa agg gct ggg tgc                 242
Val Glu Met Glu Ala Asn Ala Lys Arg Ala Gly Cys
                65                  70 cac aga gga tgt ctg att tgt ctt tcc cac atc aag                 278
His Arg Gly Cys Leu Ile Cys Leu Ser His Ile Lys
            75                  80
```

```
tgc acc aag aaa atg aag aag ttt atc cca gga aga              314
Cys Thr Lys Lys Met Lys Lys Phe Ile Pro Gly Arg
 85                  90                  95 tgc cac agt tat gaa gga gac aag gat tct gca cag              350
Cys His Ser Tyr Glu Gly Asp Lys Asp Ser Ala Gln
                100                 105 gga ggc att gga gaa gaa att gtt gac atg cct gaa              386
Gly Gly Ile Gly Glu Glu Ile Val Asp Met Pro Glu
    110                 115                 120 att ccc gga ttc aaa gac aag gaa cca atg gac caa              422
Ile Pro Gly Phe Lys Asp Lys Glu Pro Met Asp Gln
                    125                 130 ttc atc gct caa gtt gat ctc tgc gta gat tgc aca              458
Phe Ile Ala Gln Val Asp Leu Cys Val Asp Cys Thr
                135                 140 act gga tgc ctc aag ggt ctt gcc aat gtc cat tgc              494
Thr Gly Cys Leu Lys Gly Leu Ala Asn Val His Cys
145                 150                 155 tct gat ctc ctg aag aaa tgg ctt cct tca aga tgc              530
Ser Asp Leu Leu Lys Lys Trp Leu Pro Ser Arg Cys
                160                 165 aag aca ttt gct tcc aaa att caa tct caa gtg gat              566
Lys Thr Phe Ala Ser Lys Ile Gln Ser Gln Val Asp
    170                 175                 180 acc atc aag gga tta gct gga gat cgt tga                      596
Thr Ile Lys Gly Leu Ala Gly Asp Arg *
                185 gggataaaaa aatggataat tgatgatga tactttagcc caatgatgtt         646 aaaaatggcc attttcgtat taaaccataa ctatgtaaaa atgtaatgta        696 tgcaaataaa aaaaccttta acggtttaaa aaaaaaaaaa aaaaaaaaaa        746 aaaaaaa                                                      753

<210> SEQ ID NO 7
<211> LENGTH: 210
<212> TYPE: PRT
<213> ORGANISM: Artificial sequence
<220> FEATURE:
<223> OTHER INFORMATION: Variant Luciferase 1 from Metridia pacifica

<400> SEQUENCE: 7

Met Met Glu Ile Lys Val Leu Phe Ala Leu Ile Cys
 1               5                  10

Phe Ala Leu Val Gln Ala Asn Pro Thr Glu Asn Lys
            15                  20

Asp Asp Ile Asp Ile Val Gly Val Glu Gly Lys Phe
25                  30                  35

Gly Thr Thr Asp Leu Glu Thr Asp Leu Phe Thr Ile
                40                  45

Val Glu Asp Met Asn Val Ile Ser Arg Asp Thr Asn
    50                  55                  60

Leu Ala Asn Ser Asp Ala Asp Arg Gly Lys Met Pro
                65                  70

Gly Lys Lys Leu Pro Leu Glu Val Leu Ile Glu Met
        75                  80

Glu Ala Asn Ala Arg Lys Ala Gly Cys Thr Arg Gly
85                  90                  95

Cys Leu Ile Cys Leu Ser Lys Ile Lys Cys Thr Ala
```

```
                        100                 105
Lys Met Lys Val Tyr Ile Pro Gly Arg Cys His Asp
    110                 115                 120

Tyr Gly Gly Asp Lys Lys Thr Gly Gln Ala Gly Ile
                125                 130

Val Gly Ala Ile Val Asp Ile Pro Glu Ile Ser Gly
            135                 140

Phe Lys Glu Leu Gly Pro Met Glu Gln Phe Ile Ala
145                 150                 155

Gln Val Asp Leu Cys Ala Asp Cys Thr Thr Gly Cys
            160                 165

Leu Lys Gly Leu Ala Asn Val Lys Cys Ser Ala Leu
    170                 175                 180

Leu Lys Lys Trp Leu Pro Asp Arg Cys Ala Ser Phe
                185                 190

Ala Asp Lys Ile Gln Ser Glu Val Asp Asn Ile Lys
            195                 200

Gly Leu Ala Gly Asp Arg
205                 210

<210> SEQ ID NO 8
<211> LENGTH: 210
<212> TYPE: PRT
<213> ORGANISM: Artificial sequence
<220> FEATURE:
<223> OTHER INFORMATION: Variant Luciferase 1 from Metridia pacifica

<400> SEQUENCE: 8

Met Met Glu Val Lys Val Val Phe Ala Leu Ile Cys
1               5                   10

Phe Ala Leu Val Gln Ala Asn Pro Thr Glu Asn Lys
            15                  20

Asp Asp Ile Asp Ile Val Gly Val Glu Gly Lys Phe
25                  30                  35

Gly Thr Thr Asp Leu Glu Thr Asp Leu Phe Thr Ile
            40                  45

Val Glu Asp Met Asn Val Ile Ser Arg Asp Thr Asn
    50                  55                  60

Leu Ala Asn Ser Asp Ala Asp Arg Gly Lys Met Pro
                65                  70

Gly Lys Lys Leu Pro Leu Glu Val Leu Ile Glu Met
            75                  80

Glu Ala Asn Ala Arg Lys Ala Gly Cys Thr Arg Gly
85                  90                  95

Cys Leu Ile Cys Leu Ser Lys Ile Lys Cys Thr Ala
                100                 105

Lys Met Lys Val Tyr Ile Pro Gly Arg Cys His Asp
    110                 115                 120

Tyr Gly Gly Asp Lys Lys Thr Gly Gln Ala Gly Ile
                125                 130

Val Gly Ala Ile Val Asp Ile Pro Glu Ile Ser Gly
            135                 140

Phe Lys Glu Leu Gly Pro Met Glu Gln Phe Ile Ala
145                 150                 155

Gln Val Asp Leu Cys Ala Asp Cys Thr Thr Gly Cys
```

```
                        160                     165
Leu Lys Gly Leu Ala Asn Val Lys Cys Ser Ala Leu
        170                 175                 180

Leu Lys Lys Trp Leu Pro Asp Arg Cys Ala Ser Phe
                185                 190

Ala Asp Lys Ile Gln Ser Glu Val Asp Asn Ile Lys
        195                 200

Gly Leu Ala Gly Asp Arg
205                 210

<210> SEQ ID NO 9
<211> LENGTH: 633
<212> TYPE: DNA
<213> ORGANISM: Artificial sequence
<220> FEATURE:
<223> OTHER INFORMATION: cDNA encoding variant Luciferase 1 from
      Metridia pacifica

<400> SEQUENCE: 9 atg atg gaa ata aaa gtt ctt ttt gct ctc att tgc                36
Met Met Glu Ile Lys Val Leu Phe Ala Leu Ile Cys
 1               5                  10 ttt gca ttg gtg cag gcc aat cca act gaa aac aaa                72
Phe Ala Leu Val Gln Ala Asn Pro Thr Glu Asn Lys
            15                  20 gat gac att gac att gtt ggt gta gaa gga aaa ttt               108
Asp Asp Ile Asp Ile Val Gly Val Glu Gly Lys Phe
 25                  30                  35 ggt aca aca gac ctt gag aca gac tta ttc acc atc               144
Gly Thr Thr Asp Leu Glu Thr Asp Leu Phe Thr Ile
            40                  45 gtg gag gat atg aat gtc atc agt aga gac acc aat               180
Val Glu Asp Met Asn Val Ile Ser Arg Asp Thr Asn
 50                  55                  60 cta gcc aac agt gat gct gac cgc ggt aaa atg cct               216
Leu Ala Asn Ser Asp Ala Asp Arg Gly Lys Met Pro
            65                  70 ggt aaa aaa ctg cca ctg gag gta ctc ata gag atg               252
Gly Lys Lys Leu Pro Leu Glu Val Leu Ile Glu Met
 75                  80 gaa gcc aat gct cgt aaa gct ggc tgc acc agg gga               288
Glu Ala Asn Ala Arg Lys Ala Gly Cys Thr Arg Gly
 85                  90                  95 tgt ctc atc tgt ctt tca aag atc aag tgt aca gca               324
Cys Leu Ile Cys Leu Ser Lys Ile Lys Cys Thr Ala
            100                 105 aaa atg aag gtg tac att cca gga aga tgt cat gat               360
Lys Met Lys Val Tyr Ile Pro Gly Arg Cys His Asp
 110                 115                 120 tat ggc ggt gac aag aaa act gga cag gca gga ata               396
Tyr Gly Gly Asp Lys Lys Thr Gly Gln Ala Gly Ile
            125                 130 gtt ggt gcc att gtt gac att ccc gaa att tct gga               432
Val Gly Ala Ile Val Asp Ile Pro Glu Ile Ser Gly
            135                 140 ttc aag gag ttg gga ccc atg gag cag ttt att gct               468
Phe Lys Glu Leu Gly Pro Met Glu Gln Phe Ile Ala
 145                 150                 155 caa gtt gat ctt tgc gct gac tgc aca act ggc tgc               504
Gln Val Asp Leu Cys Ala Asp Cys Thr Thr Gly Cys
```

```
                160                 165
ctc aaa ggt ctt gcc aat gtc aag tgc tcc gca ctc           540
Leu Lys Gly Leu Ala Asn Val Lys Cys Ser Ala Leu
        170                 175                 180 ctg aag aaa tgg ctt cca gac aga tgt gca agt ttt           576
Leu Lys Lys Trp Leu Pro Asp Arg Cys Ala Ser Phe
                185                 190 gct gac aaa atc cag agt gaa gta gac aac atc aag           612
Ala Asp Lys Ile Gln Ser Glu Val Asp Asn Ile Lys
        195                 200 ggc ttg gct gga gat cgt tga                               633
Gly Leu Ala Gly Asp Arg  *
205                 210

<210> SEQ ID NO 10
<211> LENGTH: 633
<212> TYPE: DNA
<213> ORGANISM: Artificial sequence
<220> FEATURE:
<223> OTHER INFORMATION: cDNA encoding variant Luciferase 1 from
      Metridia pacifica

<400> SEQUENCE: 10 atg atg gaa gta aaa gtt gtt ttt gct ctc att tgc           36
Met Met Glu Val Lys Val Val Phe Ala Leu Ile Cys
1               5                   10 ttt gca ttg gtg cag gcc aat cca act gaa aac aaa           72
Phe Ala Leu Val Gln Ala Asn Pro Thr Glu Asn Lys
        15                  20 gat gac att gac att gtt ggt gta gaa gga aaa ttt           108
Asp Asp Ile Asp Ile Val Gly Val Glu Gly Lys Phe
25                  30                  35 ggt aca aca gac ctt gag aca gac tta ttc acc atc           144
Gly Thr Thr Asp Leu Glu Thr Asp Leu Phe Thr Ile
                40                  45 gtg gag gat atg aat gtc atc agt aga gac acc aat           180
Val Glu Asp Met Asn Val Ile Ser Arg Asp Thr Asn
        50                  55                  60 cta gcc aac agt gat gct gac cgc ggt aaa atg cct           216
Leu Ala Asn Ser Asp Ala Asp Arg Gly Lys Met Pro
                65                  70 ggt aaa aaa ctg cca ctg gag gta ctc ata gag atg           252
Gly Lys Lys Leu Pro Leu Glu Val Leu Ile Glu Met
        75                  80 gaa gcc aat gct cgt aaa gct ggc tgc acc agg gga           288
Glu Ala Asn Ala Arg Lys Ala Gly Cys Thr Arg Gly
85                  90                  95 tgt ctc atc tgt ctt tca aag atc aag tgt aca gca           324
Cys Leu Ile Cys Leu Ser Lys Ile Lys Cys Thr Ala
                100                 105 aaa atg aag gtg tac att cca gga aga tgt cat gat           360
Lys Met Lys Val Tyr Ile Pro Gly Arg Cys His Asp
        110                 115                 120 tat ggc ggt gac aag aaa act gga cag gca gga ata           396
Tyr Gly Gly Asp Lys Lys Thr Gly Gln Ala Gly Ile
                125                 130 gtt ggt gcc att gtt gac att ccc gaa att tct gga           432
Val Gly Ala Ile Val Asp Ile Pro Glu Ile Ser Gly
        135                 140 ttc aag gag ttg gga ccc atg gag cag ttt att gct           468
Phe Lys Glu Leu Gly Pro Met Glu Gln Phe Ile Ala
```

-continued

```
                       145                 150                 155
caa gtt gat ctt tgc gct gac tgc aca act ggc tgc                        504
Gln Val Asp Leu Cys Ala Asp Cys Thr Thr Gly Cys
            160                 165 ctc aaa ggt ctt gcc aat gtc aag tgc tcc gca ctc                        540
Leu Lys Gly Leu Ala Asn Val Lys Cys Ser Ala Leu
    170                 175                 180 ctg aag aaa tgg ctt cca gac aga tgt gca agt ttt                        576
Leu Lys Lys Trp Leu Pro Asp Arg Cys Ala Ser Phe
                185                 190 gct gac aaa atc cag agt gaa gta gac aac atc aag                        612
Ala Asp Lys Ile Gln Ser Glu Val Asp Asn Ile Lys
        195                 200 ggc ttg gct gga gat cgt tga                                            633
Gly Leu Ala Gly Asp Arg  *
205                 210

<210> SEQ ID NO 11
<211> LENGTH: 57
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (57)..(57)
<223> OTHER INFORMATION: n is a, c, g, or t

<400> SEQUENCE: 11
aagcagtggt aacaacgcag agtactttt ttttttttt tttttttttt ttttttvn         57

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 12
ggctgcacya ggggatgyct katmtc                                          26

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 13
gctattgttg ayatyccyga rat                                             23

<210> SEQ ID NO 14
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 14
tcaagttgwt caatraaytg ytccat                                          26

<210> SEQ ID NO 15
<211> LENGTH: 23
<212> TYPE: DNA
<213> ORGANISM: Artificial Sequence
```

```
<220> FEATURE:
<223> OTHER INFORMATION: Synthetic oligonucleotide primer

<400> SEQUENCE: 15
acattggcaa gaccyttvag rca                                              23

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 16
aacgatctcc agccaagccc ttgatgttgt                                       30

<210> SEQ ID NO 17
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 17
tcagcgcaaa gatcaacttg agcaatgaac                                       30

<210> SEQ ID NO 18
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 18
ggagacaact ggatccaaaa ggaaaggagc taaatctac                             39

<210> SEQ ID NO 19
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 19
aaaaggaaag gagctaaatc tacagtcta                                        29

<210> SEQ ID NO 20
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 20
gagtccaaac tgaaaggtac tcaaaaatgg gagtcaa                               37

<210> SEQ ID NO 21
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 21
actgttgact agattggtgt ctctactgat gacattc                               37
```

<210> SEQ ID NO 22
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 22
ggattacata gaatatattt ataggaa                                27

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 23
catgatccag ttatctcttg ttctgttct                              29

<210> SEQ ID NO 24
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 24
atttttacat agttatggtt taatacga                               28

<210> SEQ ID NO 25
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 25
taacatcatt gggctaaagt atcatcatc                              29

<210> SEQ ID NO 26
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 26 cacc atg atg gaa ata aaa gtt ctt ttt gct ctc                 34
     Met Met Glu Ile Lys Val Leu Phe Ala Leu
     1               5                   10

<210> SEQ ID NO 27
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 27 cacc atg atg gaa gta aaa gtt gtt ttt gct ctc                 34
     Met Met Glu Val Lys Val Val Phe Ala Leu
     1               5                   10

<210> SEQ ID NO 28
<211> LENGTH: 34

-continued

```
<212> TYPE: DNA
<213> ORGANISM: Artificial Sequence
<220> FEATURE:
<223> OTHER INFORMATION: Synthetic oligonucleotide primer

<400> SEQUENCE: 28 cacc atg atg gaa ata caa gtt ctt ttt gct ctc                              34
     Met Met Glu Ile Gln Val Leu Phe Ala Leu
     1               5                  10

<210> SEQ ID NO 29
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 29
tcaacgatct ccagccaagc ccttgatgt                                           29

<210> SEQ ID NO 30
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 30 cacc atg gga gtc aaa ctt atc ttt gct gt                                   30
     Met Gly Val Lys Leu Ile Phe Ala
     1               5

<210> SEQ ID NO 31
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 31
tcaacgatct ccagctaagc ccttgatg                                            28
```